(12) United States Patent
Sheth et al.

(10) Patent No.: US 10,169,607 B1
(45) Date of Patent: Jan. 1, 2019

(54) INDIVIDUAL CENTRIC PERSONAL DATA MANAGEMENT PROCESS AND METHOD

(71) Applicants: Dinesh Sheth, Pensacola Beach, FL (US); Sanjay R. Parikh, Camel, IN (US); Arun Raj, Trivandrum (IN)

(72) Inventors: Dinesh Sheth, Pensacola Beach, FL (US); Sanjay R. Parikh, Camel, IN (US); Arun Raj, Trivandrum (IN)

( * ) Notice: Subject to any disclaimer, the term of this patent is extended or adjusted under 35 U.S.C. 154(b) by 365 days.

(21) Appl. No.: 14/256,247

(22) Filed: Apr. 18, 2014

(51) Int. Cl.
*G06F 19/00* (2018.01)
*G06F 21/62* (2013.01)
*G16H 10/60* (2018.01)
*G06Q 20/08* (2012.01)

(52) U.S. Cl.
CPC ..... *G06F 21/6245* (2013.01); *G06Q 20/0855* (2013.01); *G16H 10/60* (2018.01)

(58) Field of Classification Search
CPC ........ G06Q 10/10; G06Q 50/24; G06Q 50/22; G06Q 20/40145; G06Q 20/3674; G06Q 20/382; G06Q 20/0855; G06F 21/31; G06F 21/36; G06F 19/3418; G06F 21/6245; G06F 19/3462; G16H 10/60
See application file for complete search history.

*Primary Examiner* — Maroun P Kanaan
(74) *Attorney, Agent, or Firm* — J. Nevin Shaffer, Jr.

(57) ABSTRACT

An individual centric personal data management process consisting of utilizing at least one computing device for performing the function of facilitating personal data management by an individual. The process further consisting of an analyzer step, the process sending a message received from a message source to an analyzer means for establishing login security and authentication of an authorized user; a prompt step, the process providing a prompt to the authorized user for entry of data to a data repository; a data entry normalization step, the process inserting previously entered data where a subsequent request for data from the authorized user for entry of the same data is detected; an authorized recipient step; the process identifying an authorized recipient such that the authorized recipient is provided access to authorized user selected data from the data repository; where the data repository contains data authorized to be entered by the authorized user and from which the authorized user selects data to be shared with the authorized recipient.

25 Claims, 69 Drawing Sheets

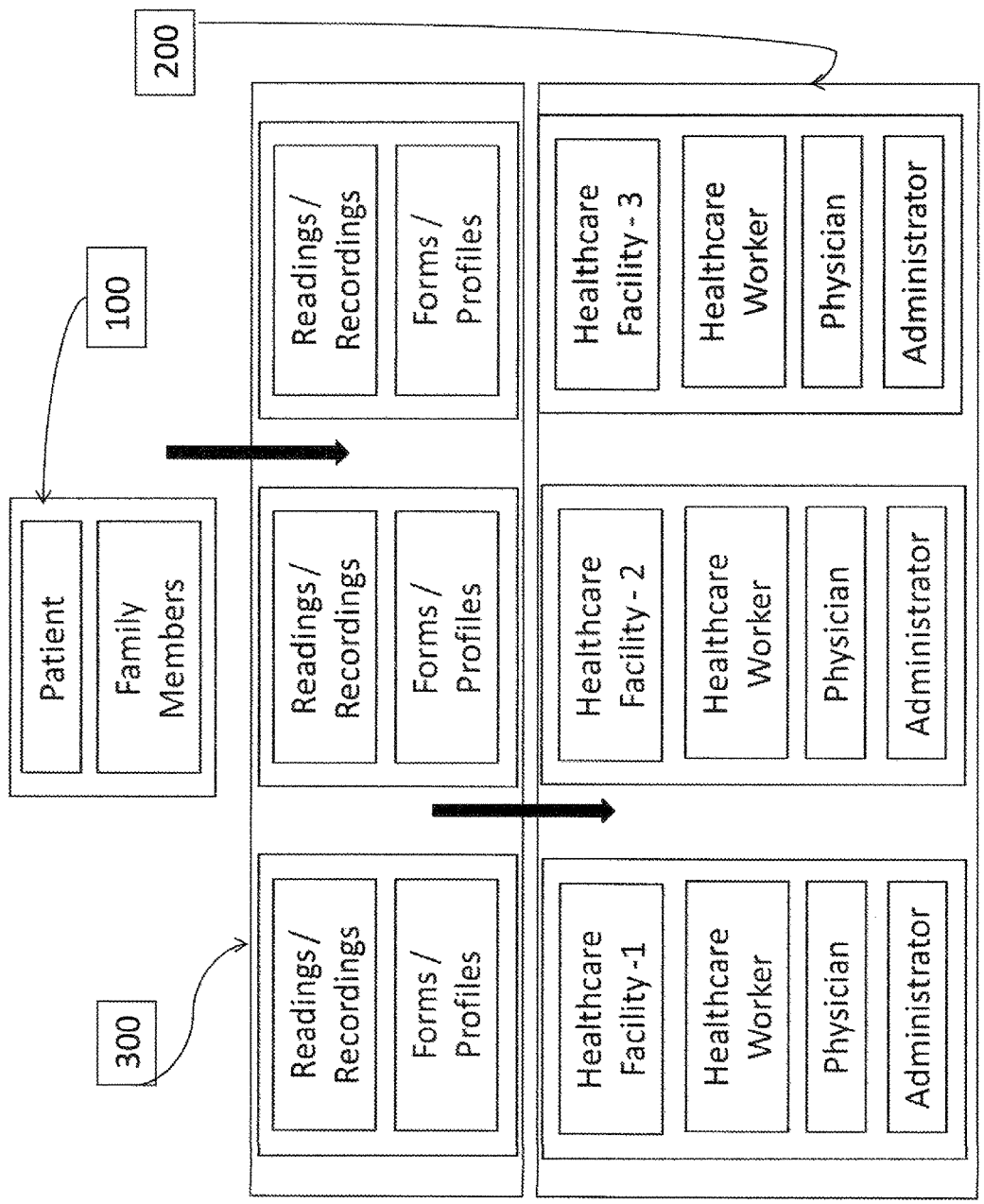
FIG. 2-A

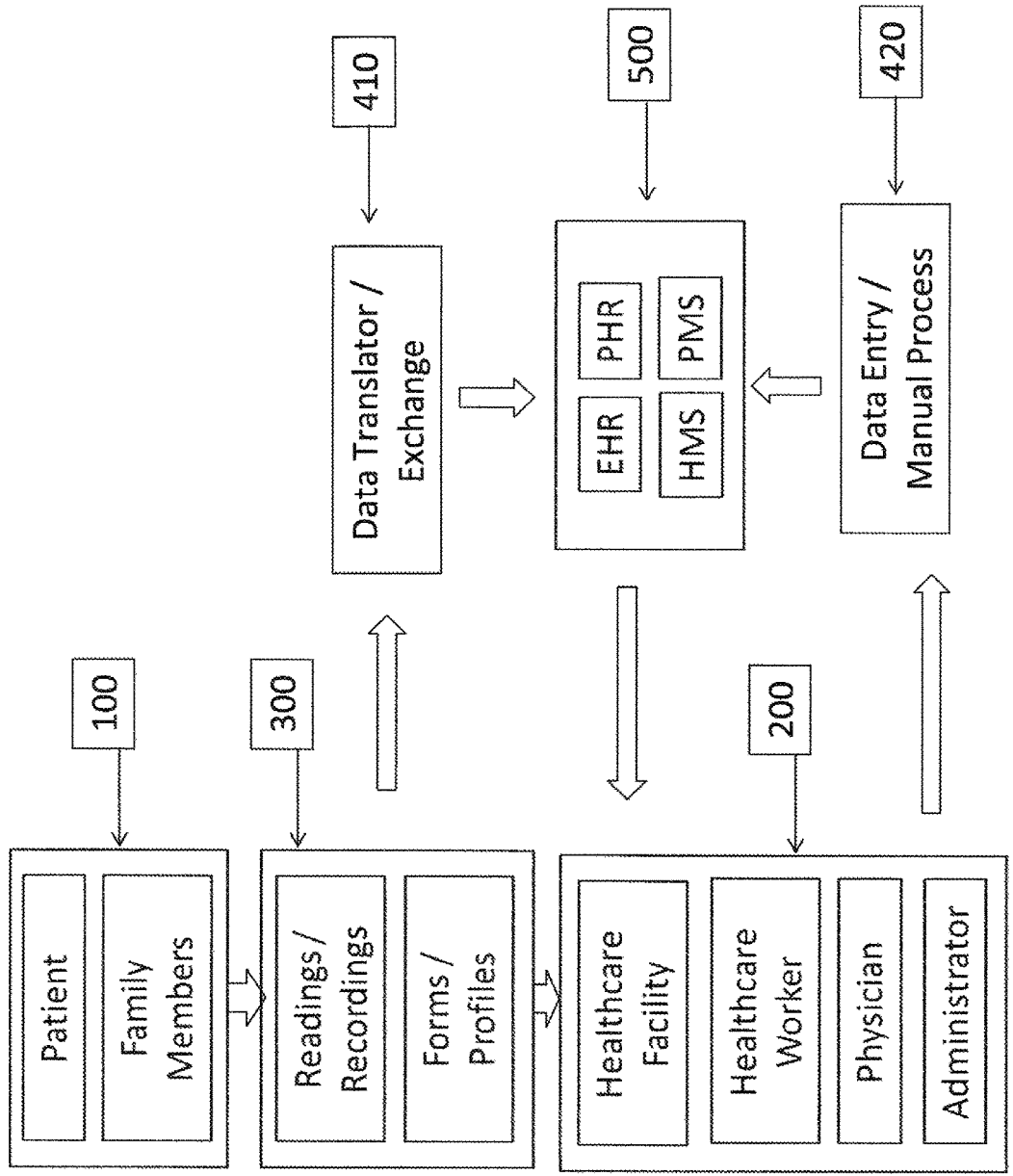
FIG. 2-B

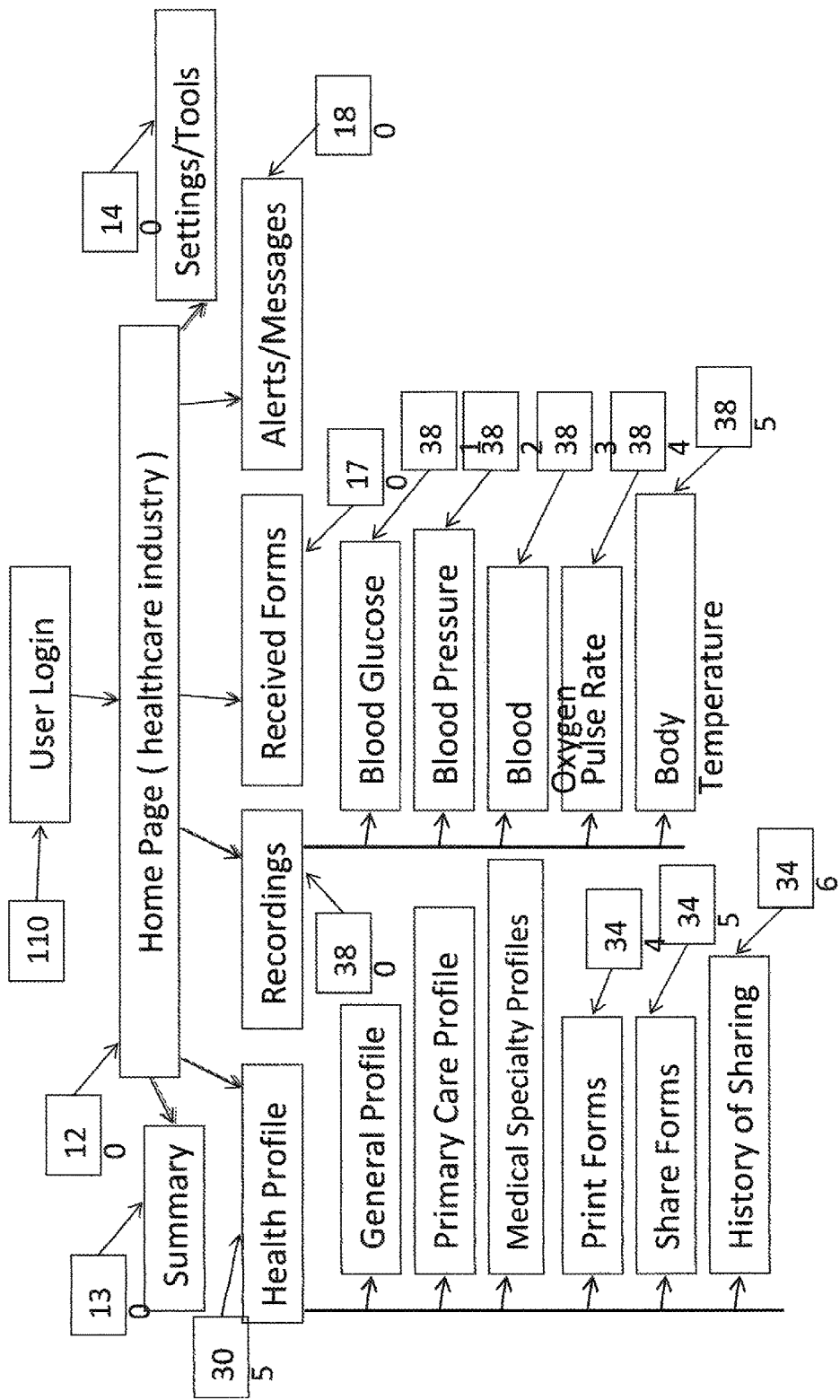
FIG. 7-A

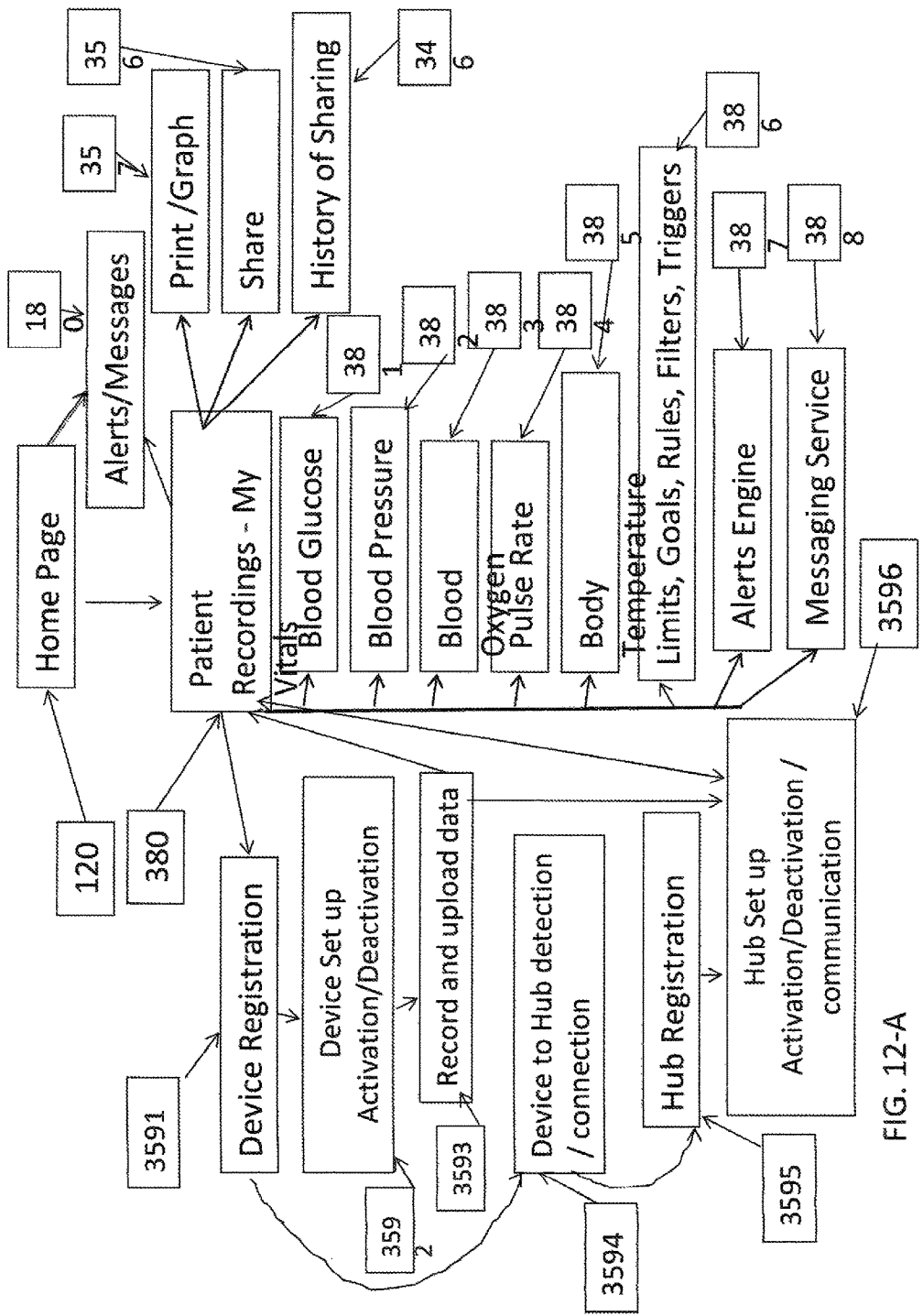
FIG. 12-A

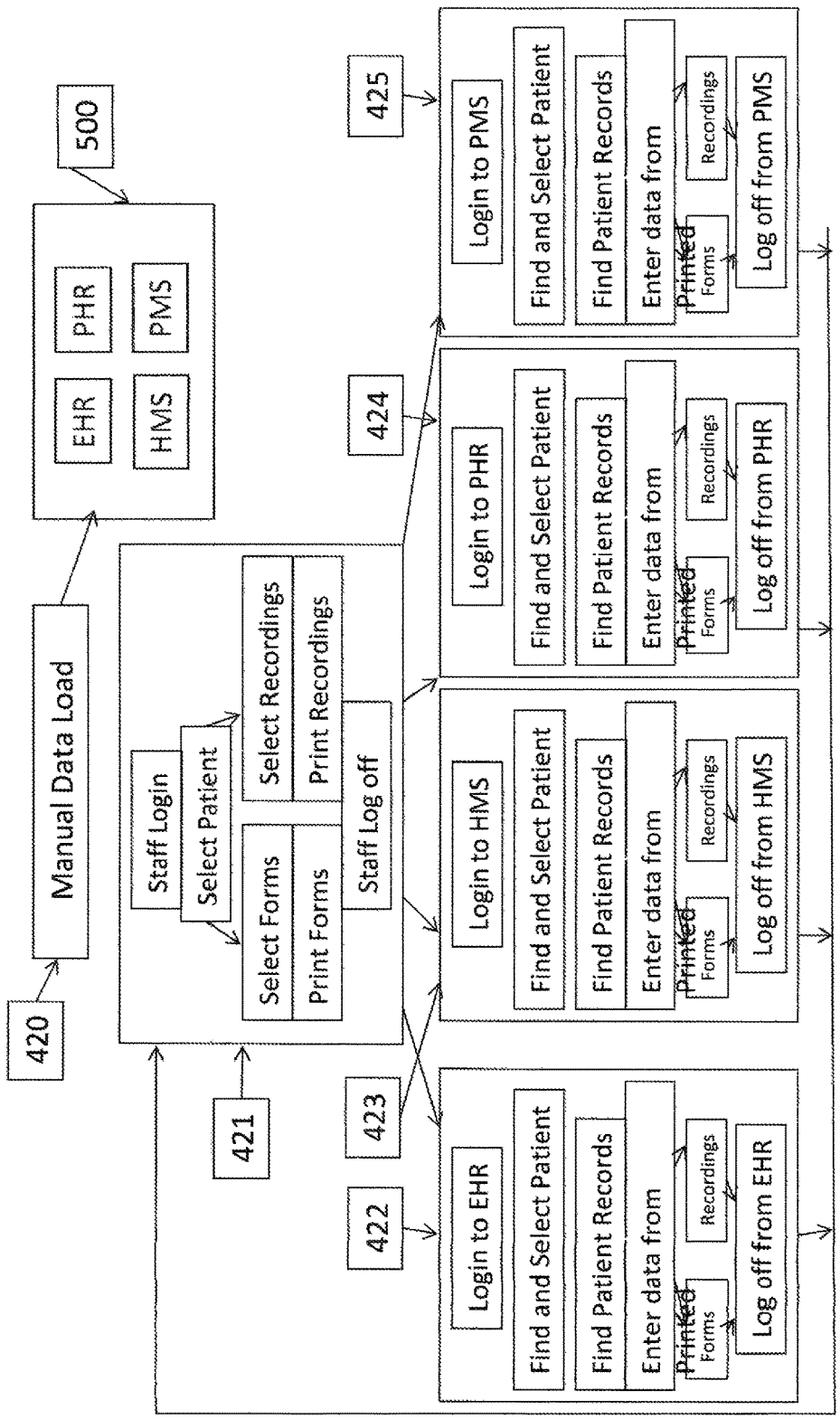
FIG. 18-A

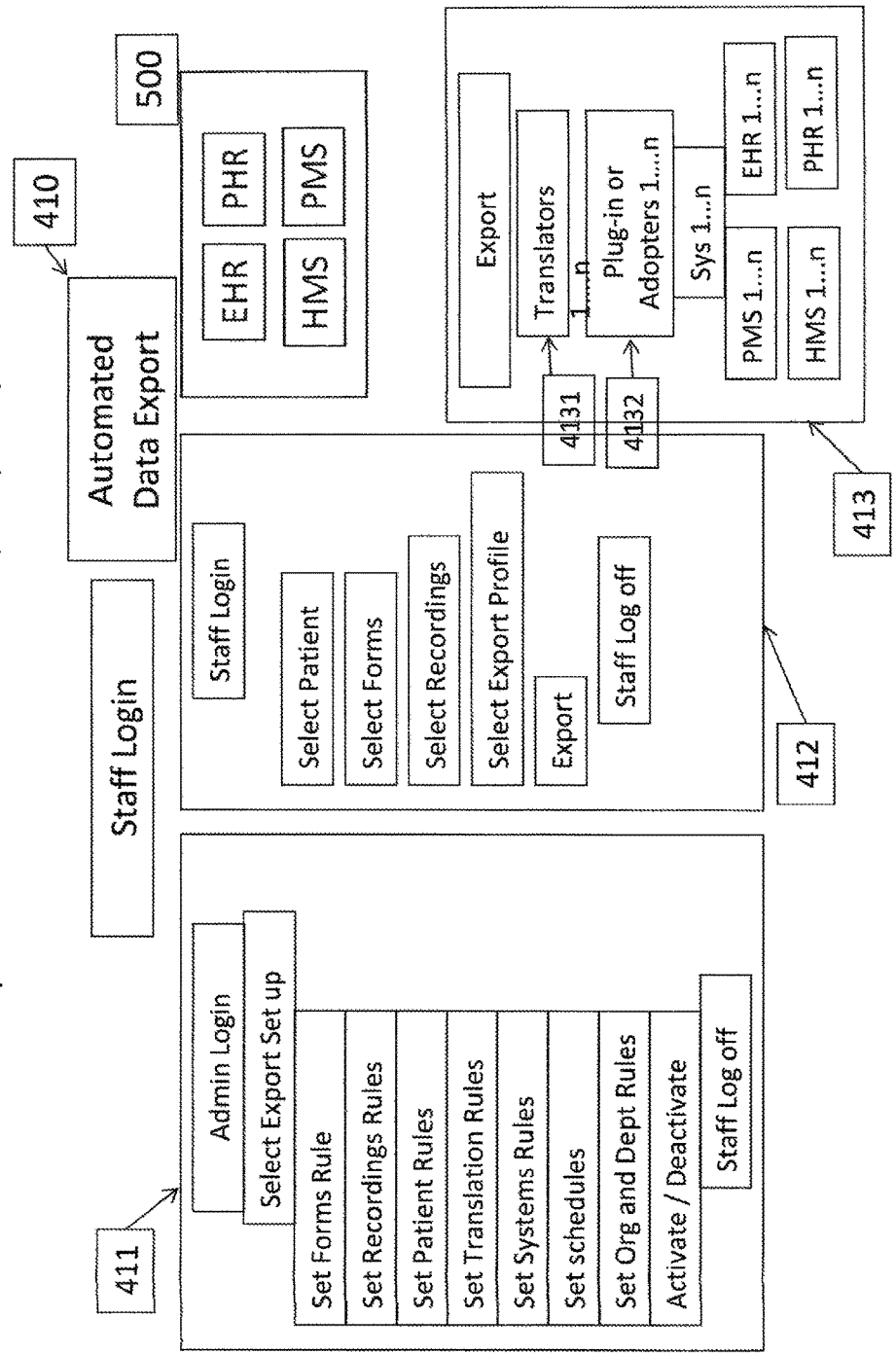
FIG. 18-B

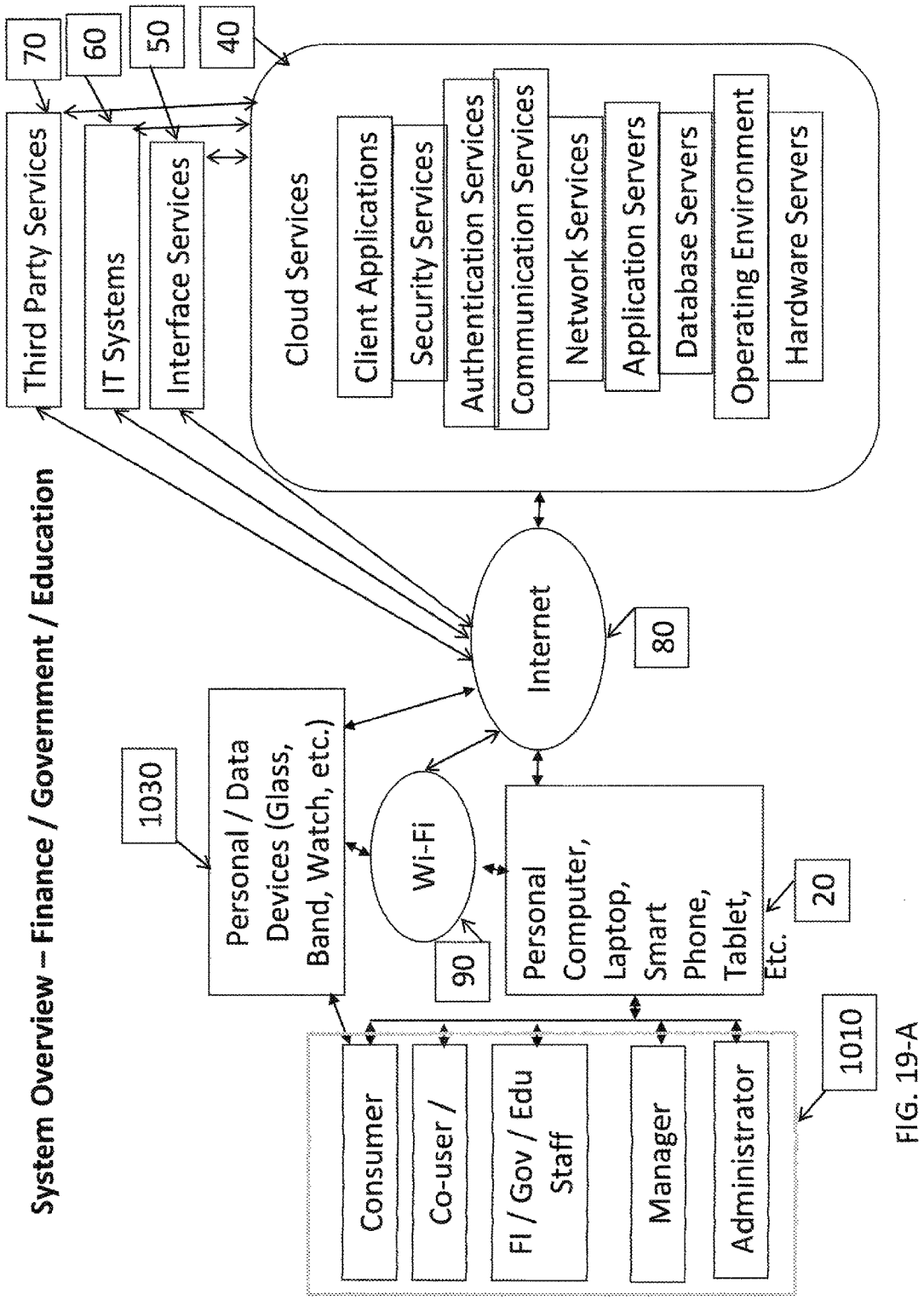
FIG. 19-A

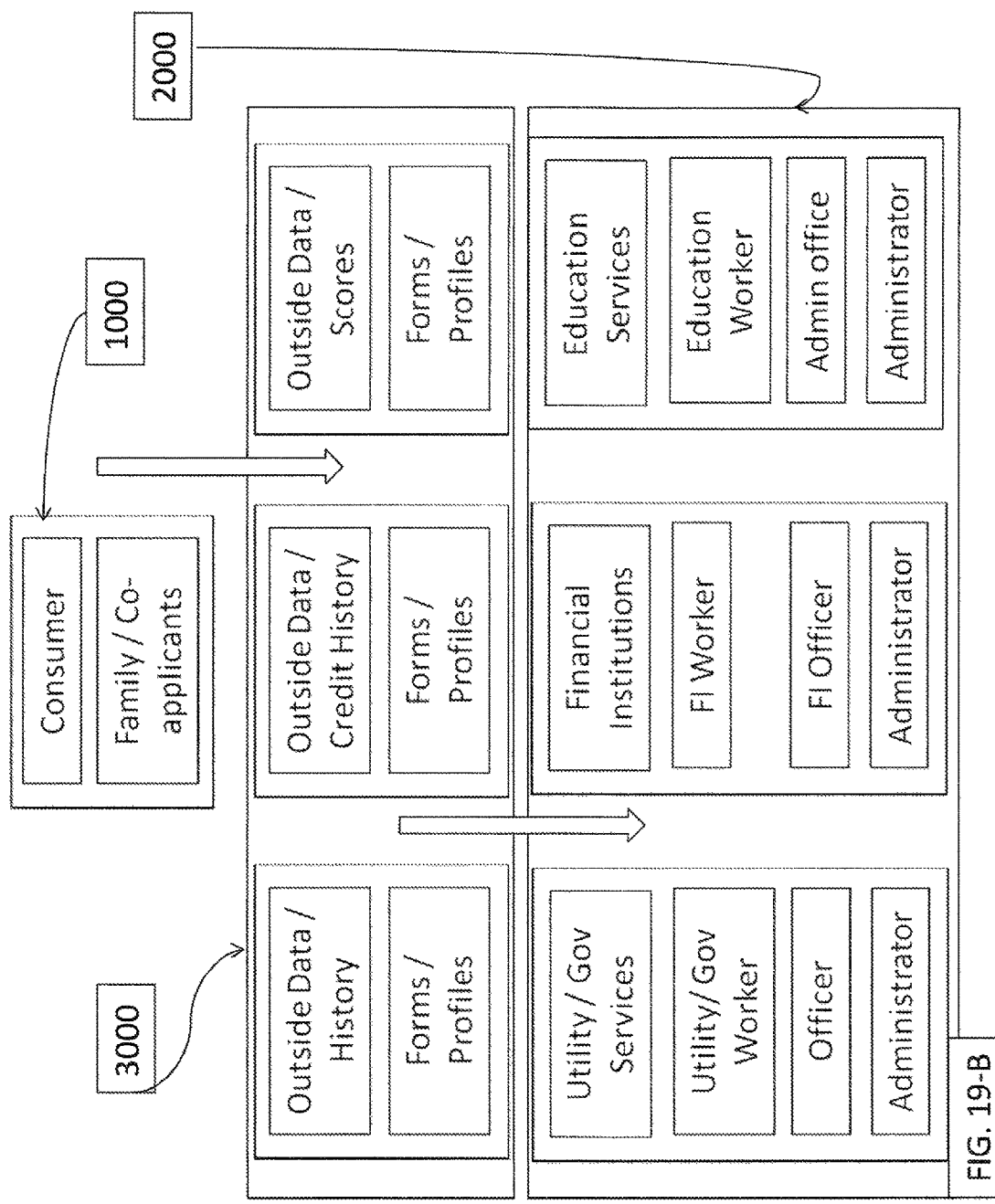
FIG. 19-B

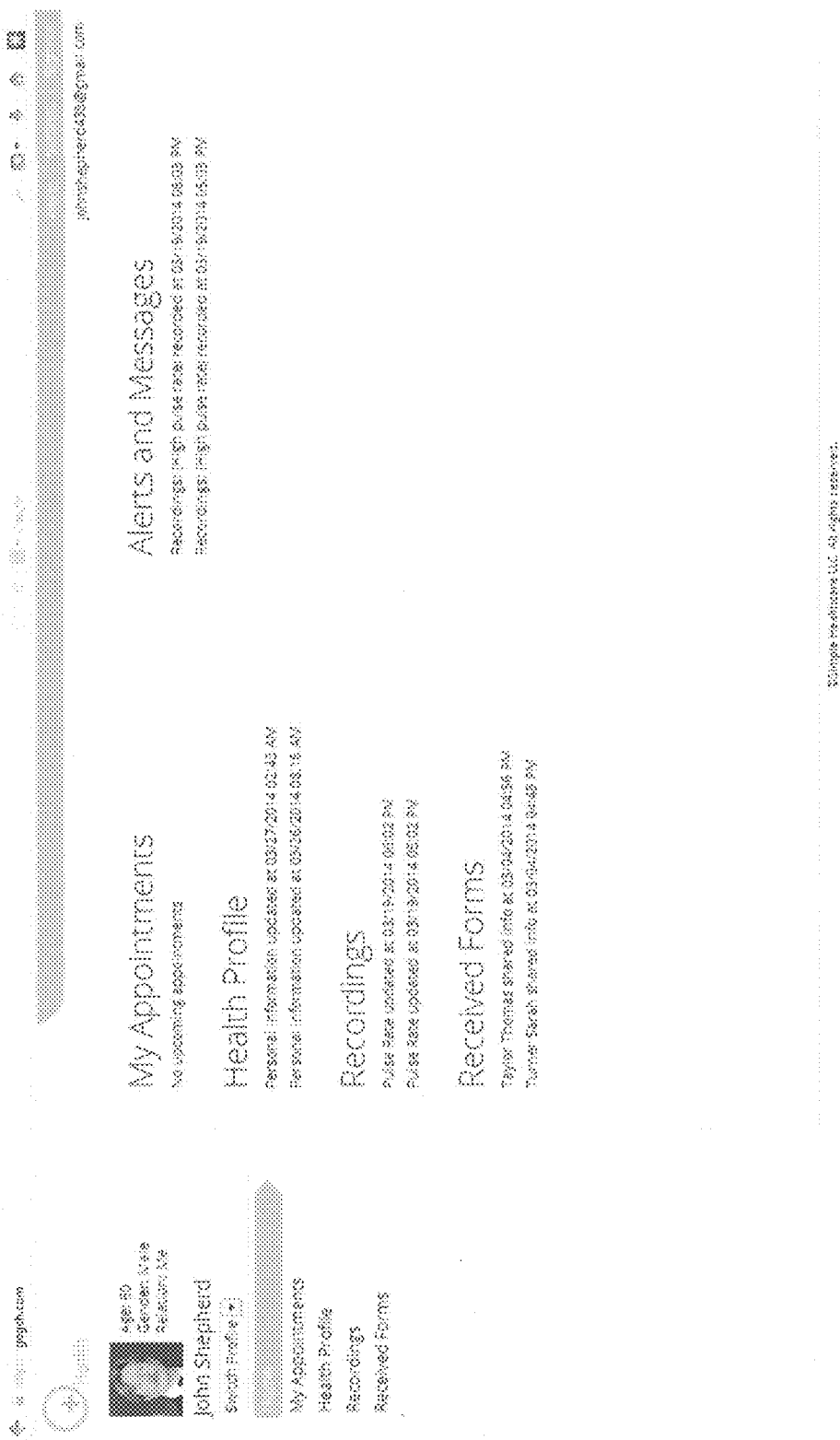
FIG. 21-A

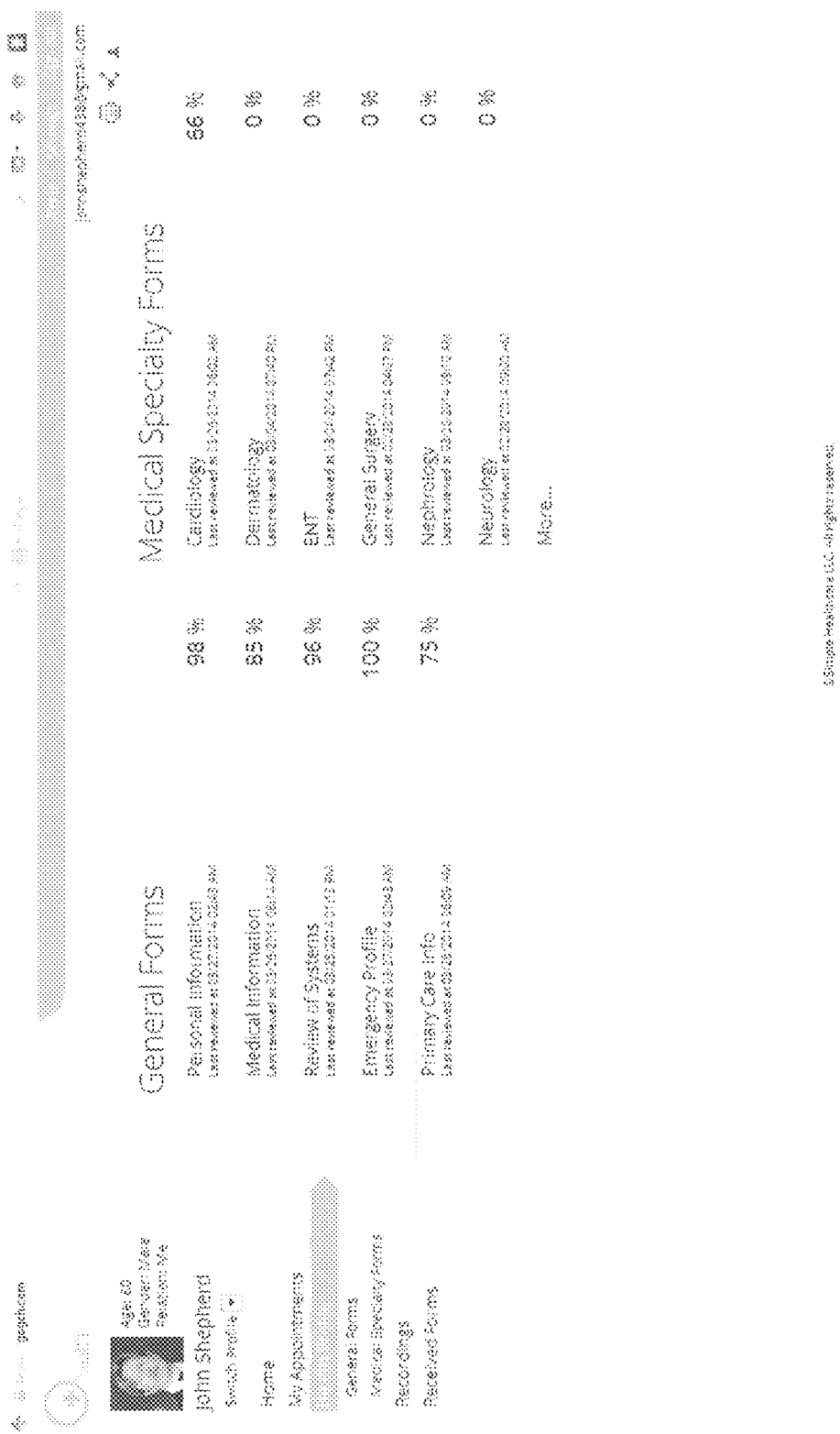
FIG. 21-B

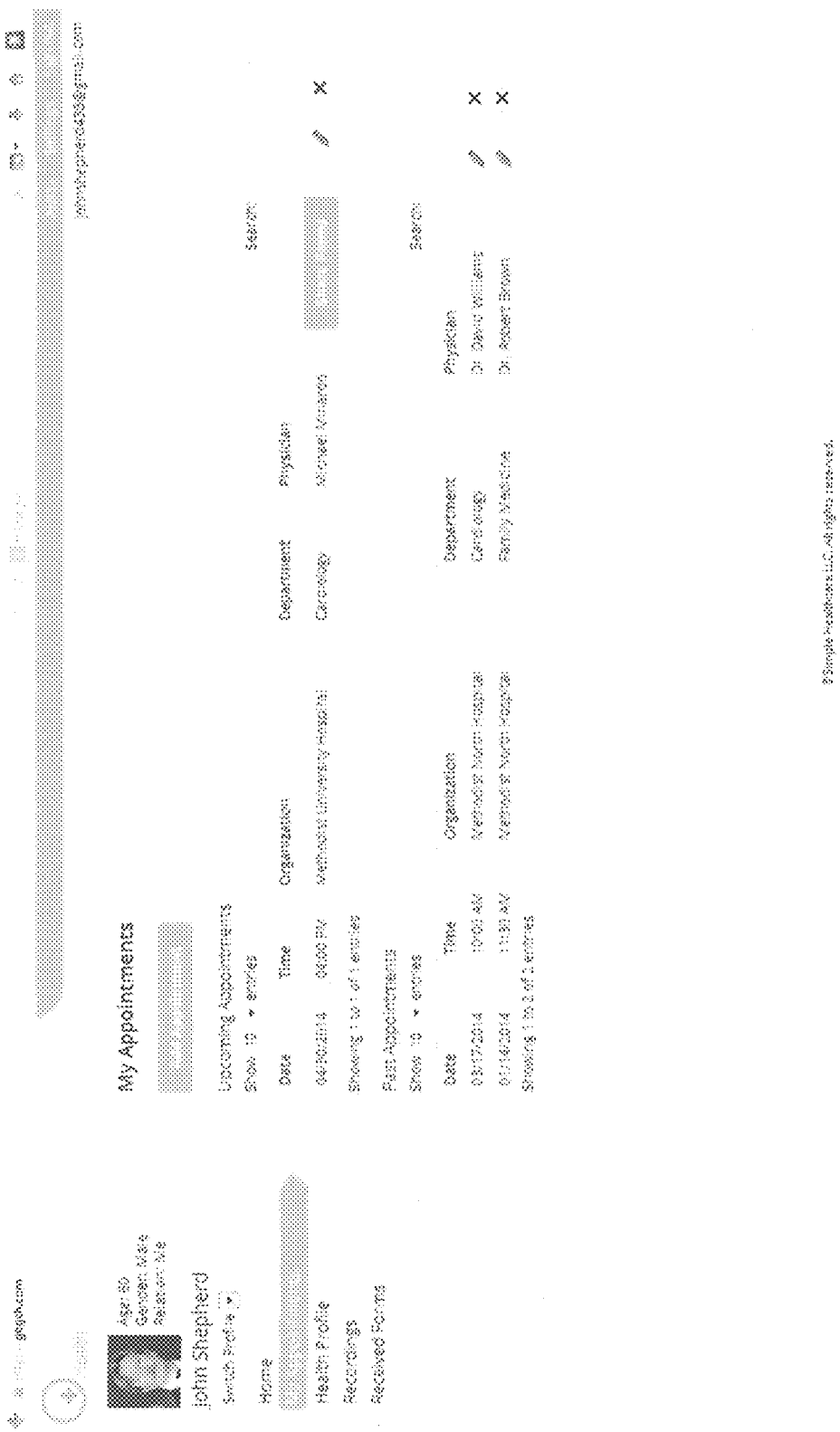
FIG. 21-C

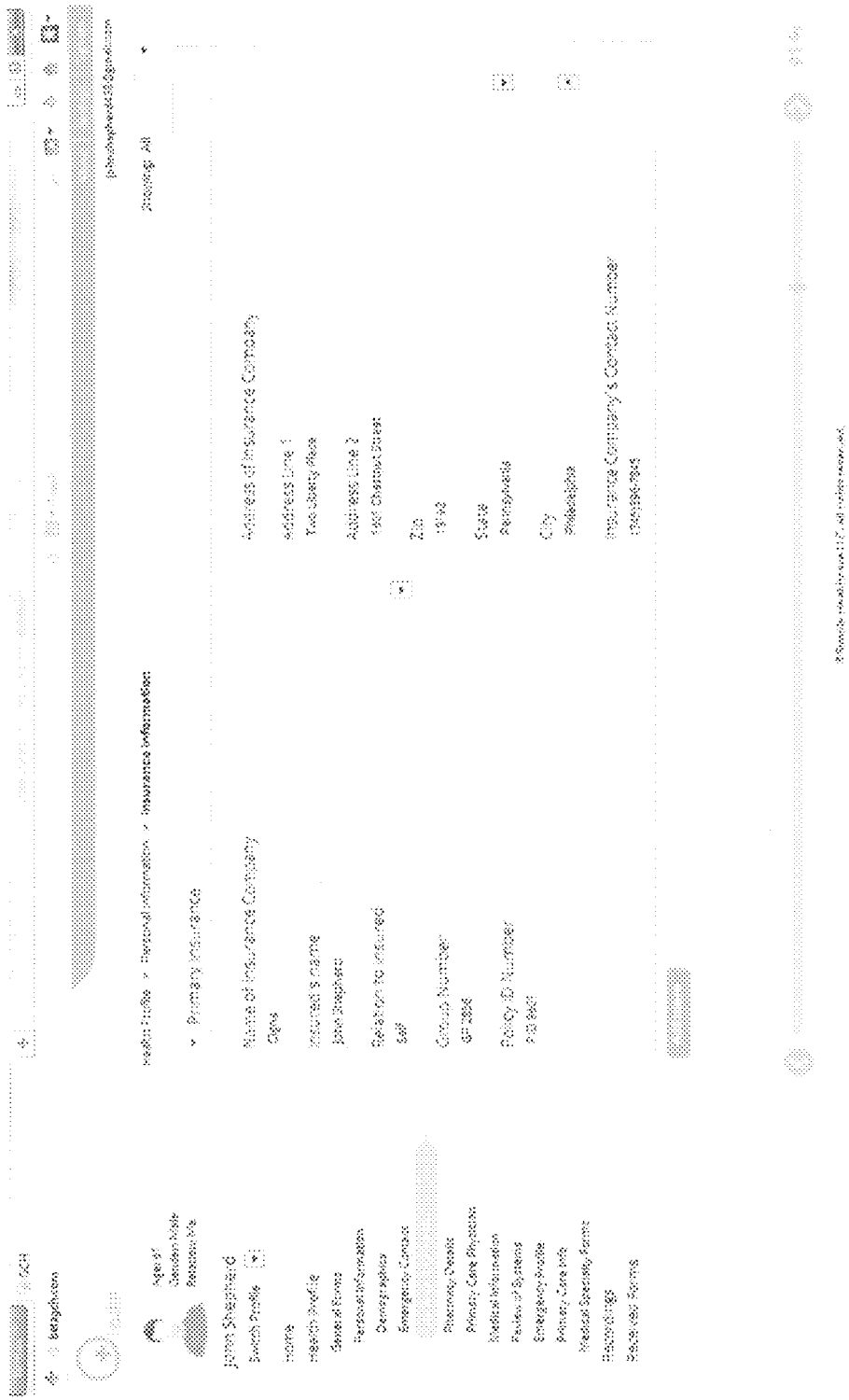
FIG. 25-A

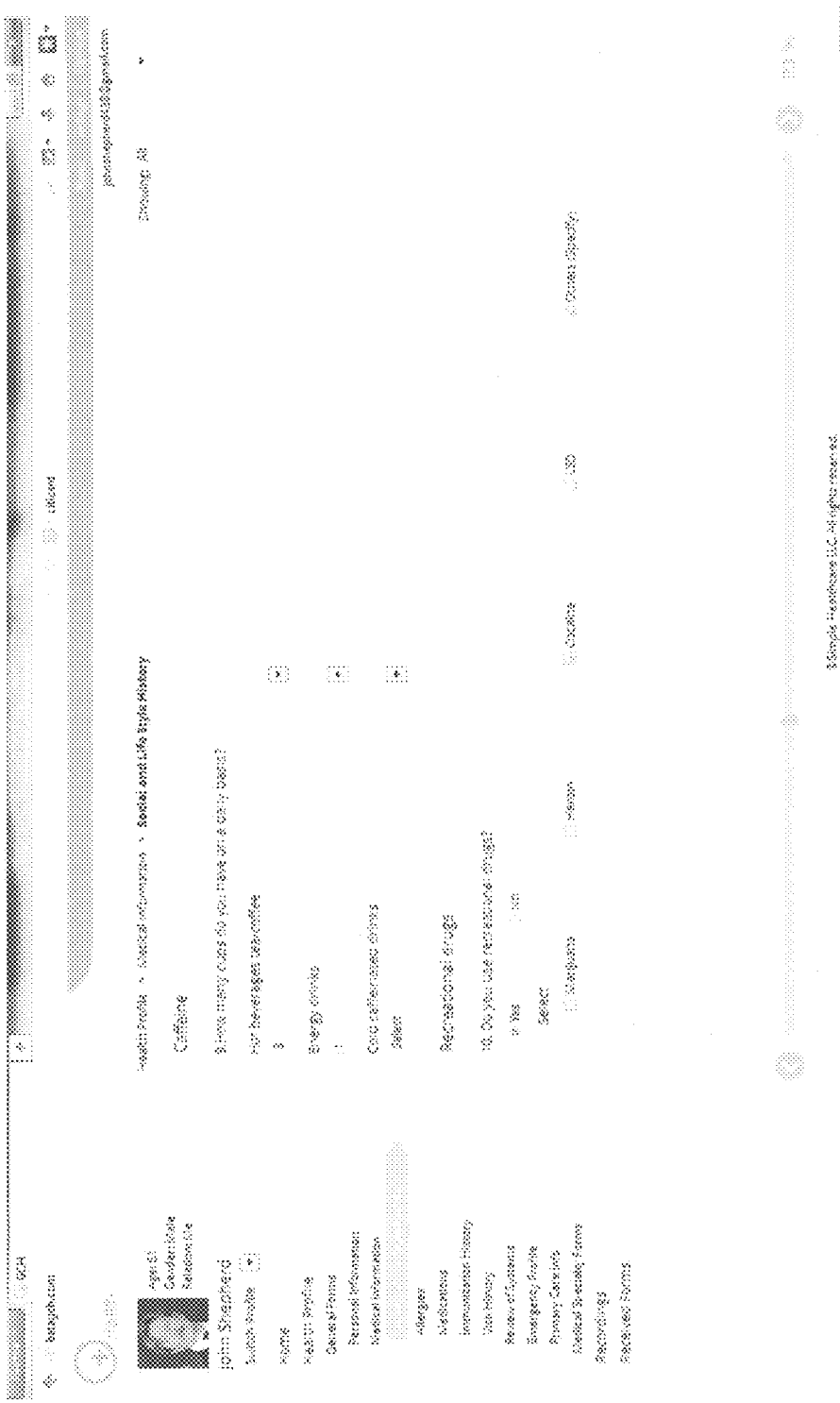
FIG. 25-B

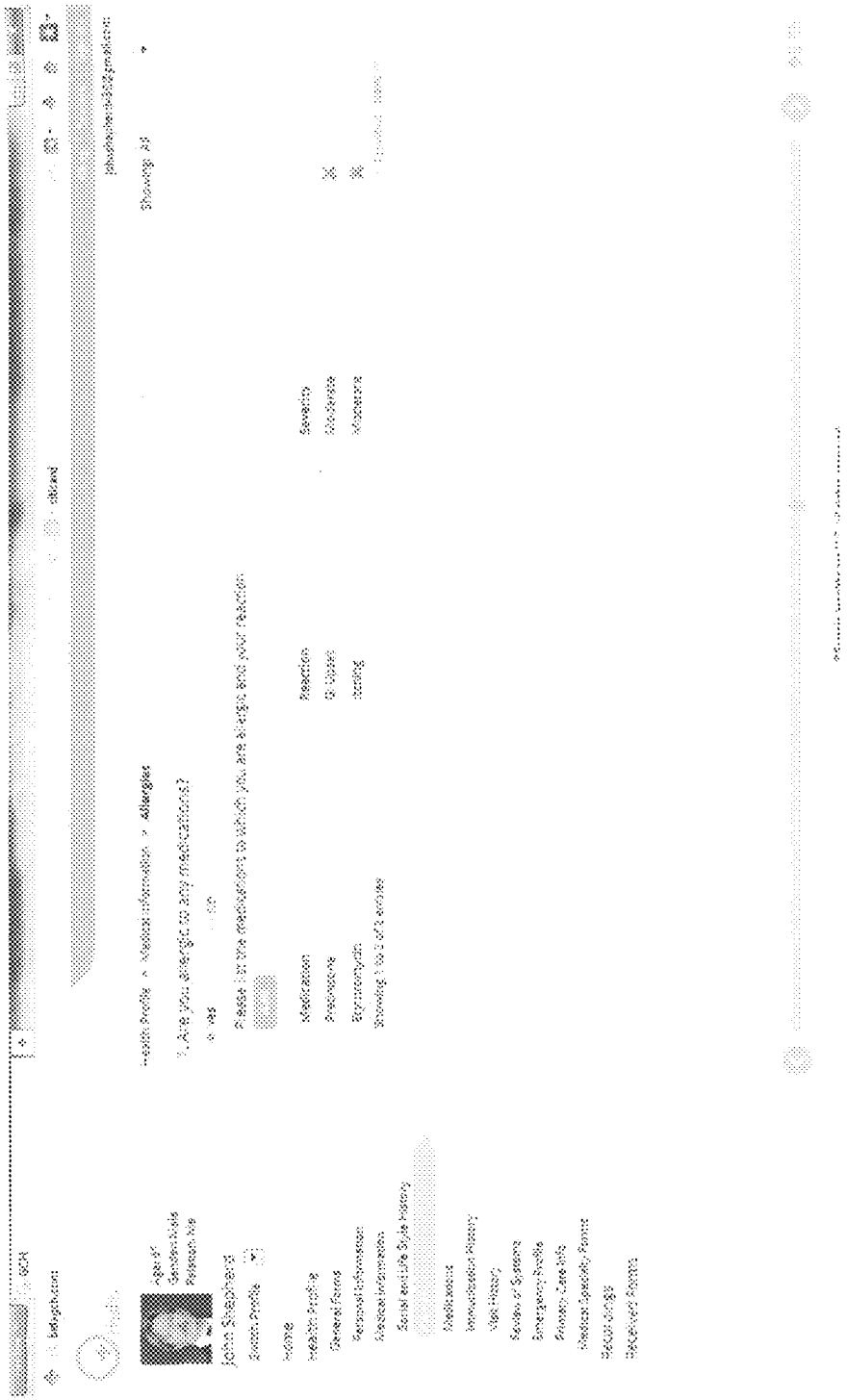
FIG. 25-C

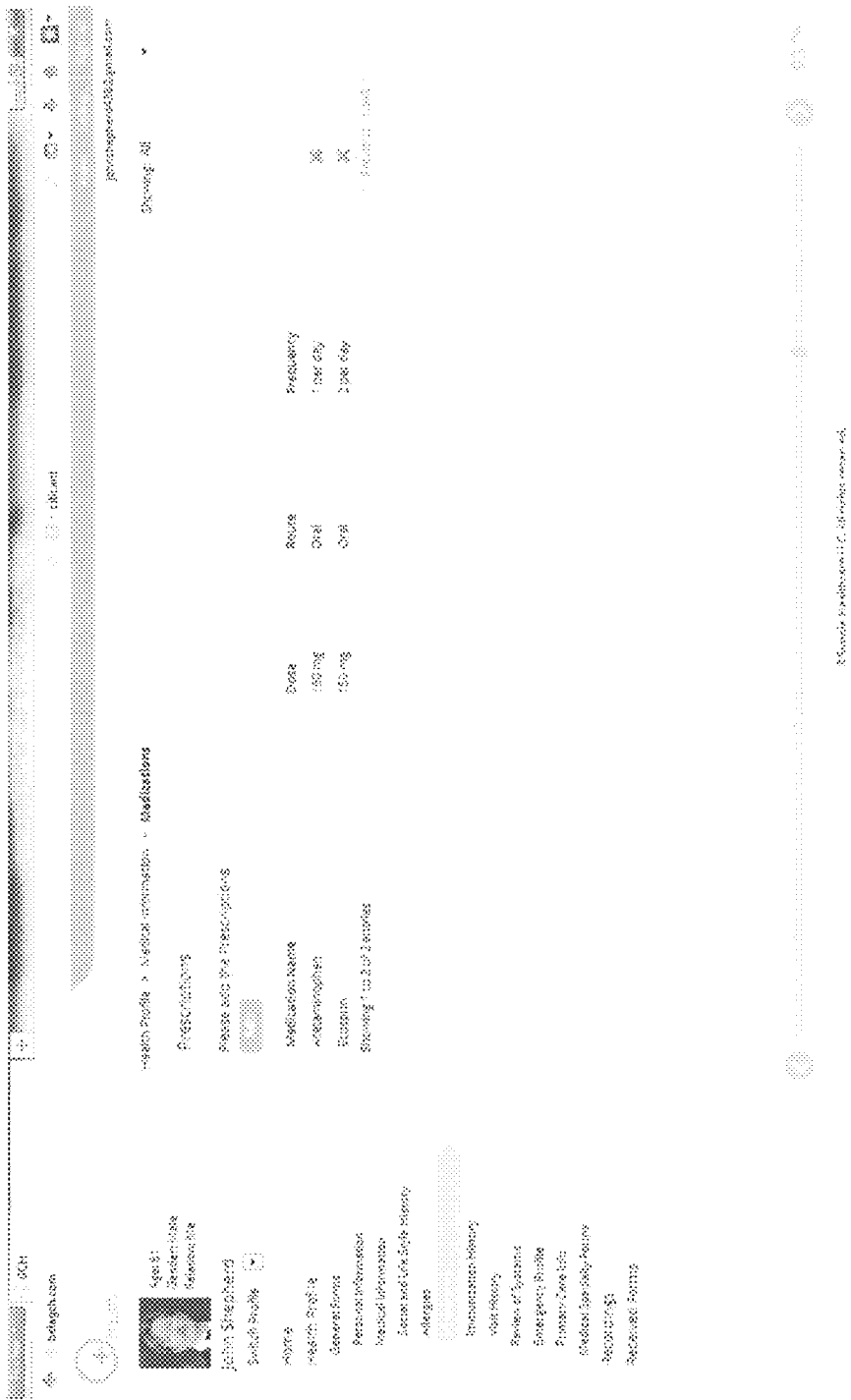
FIG. 25-D

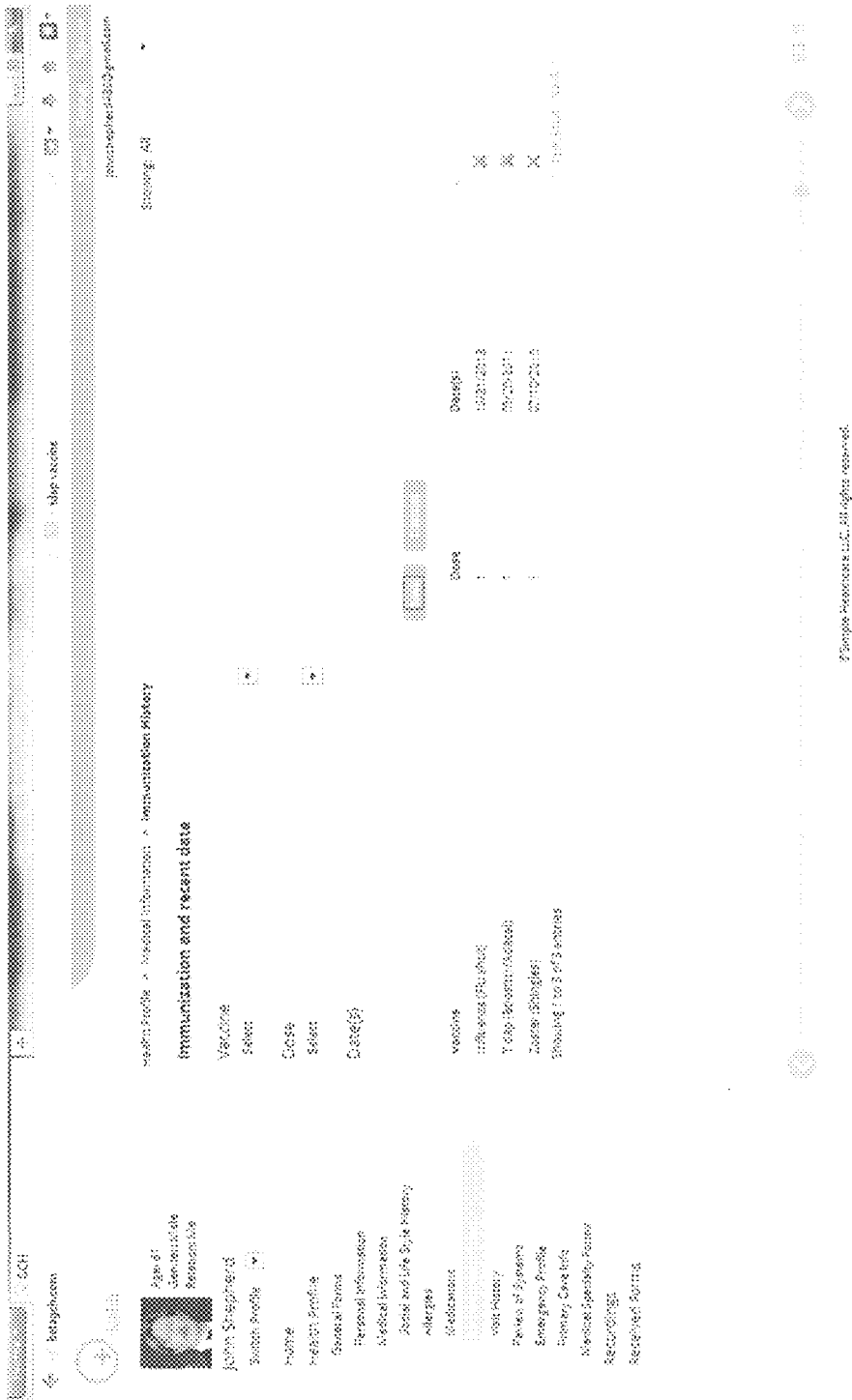
FIG. 25-E

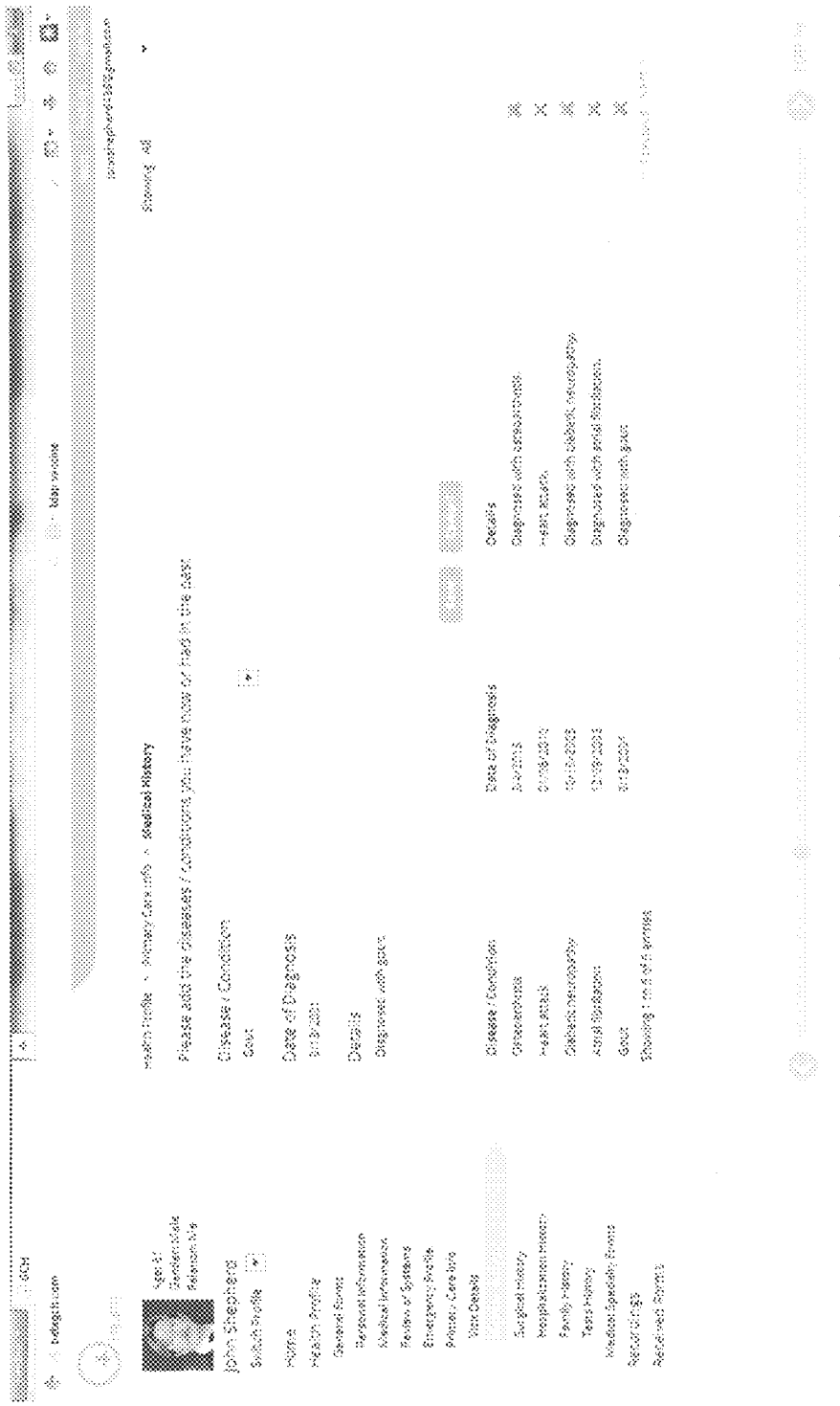
FIG. 25-F

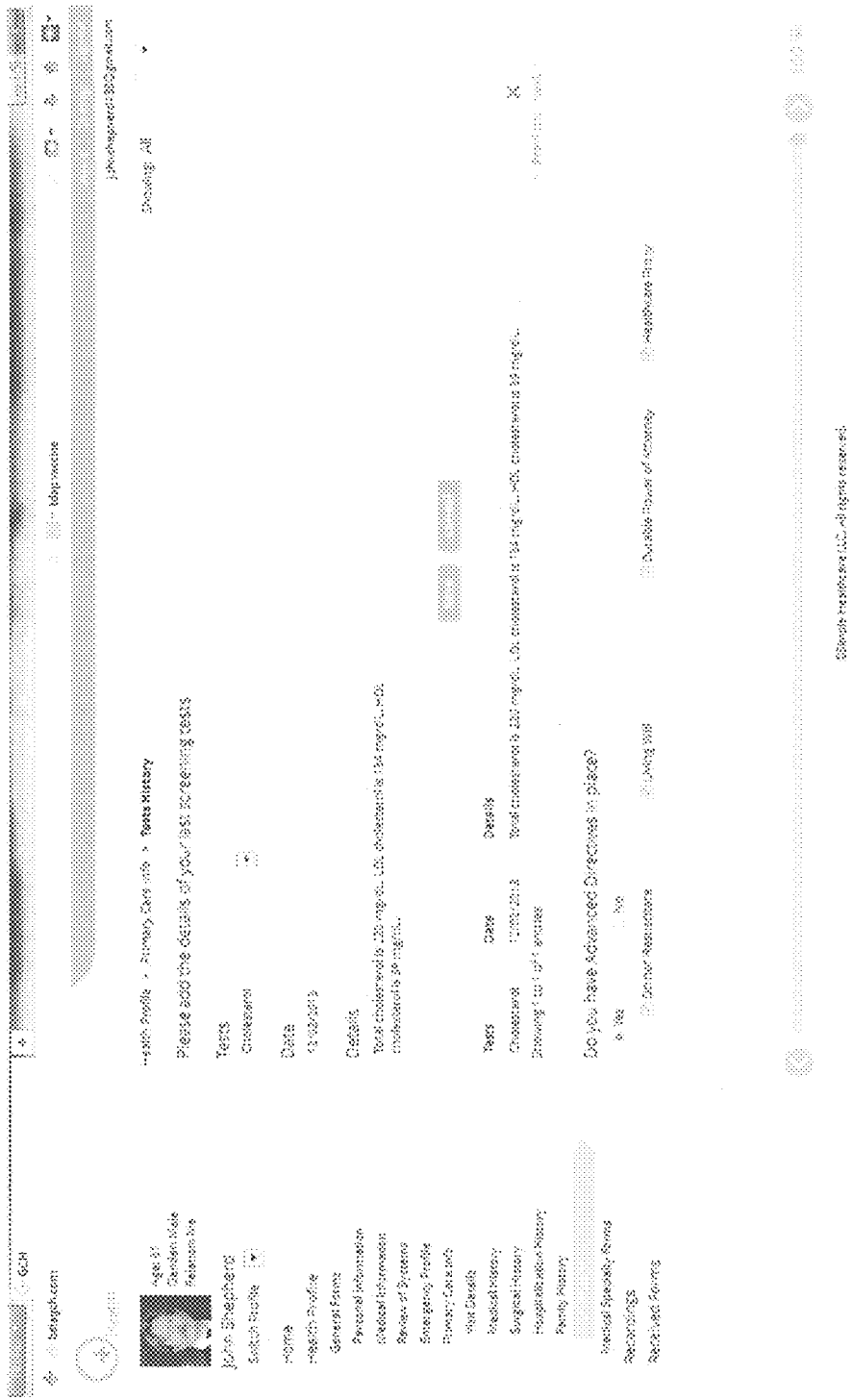
FIG. 25-G

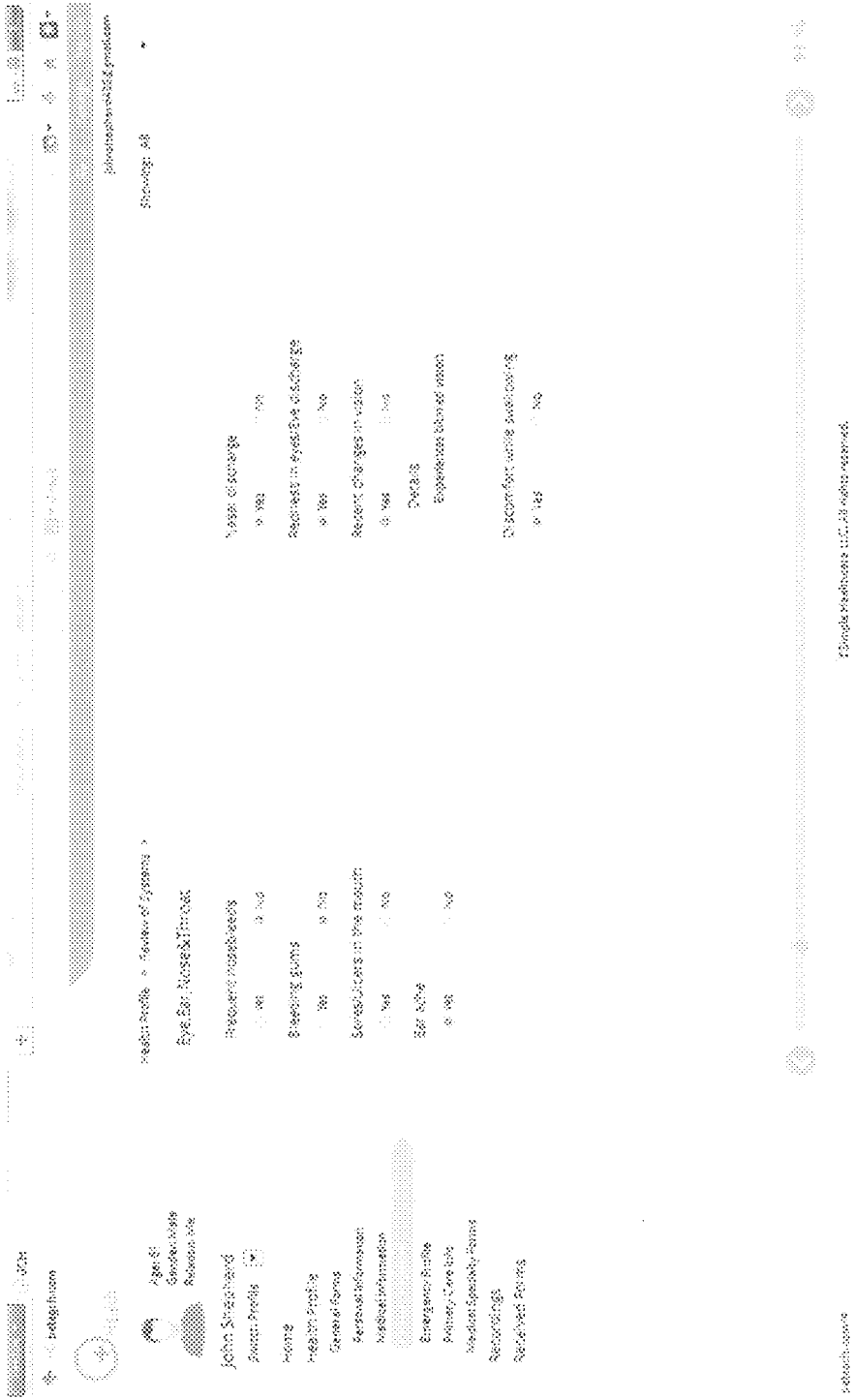
FIG. 26-A

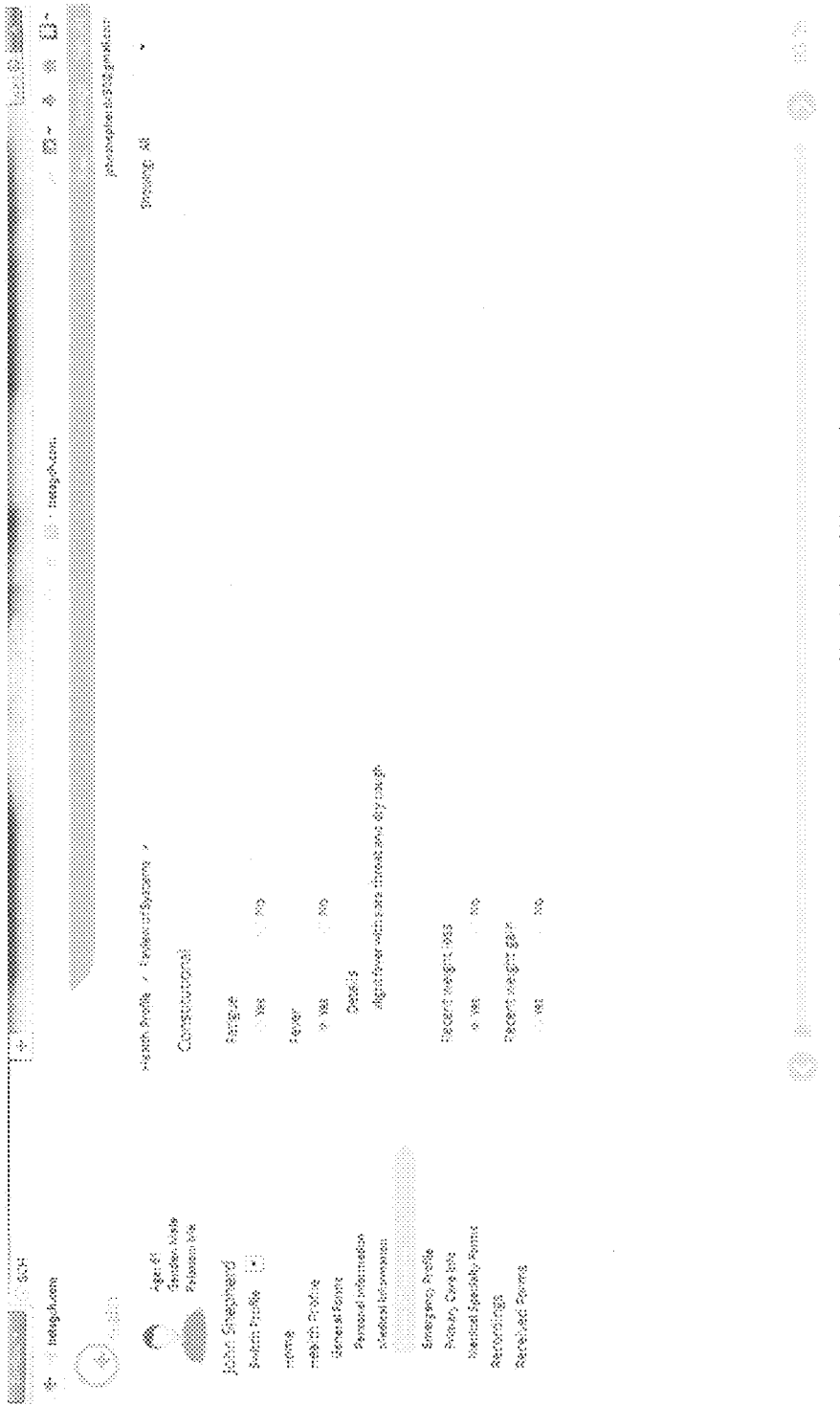
FIG. 26-B

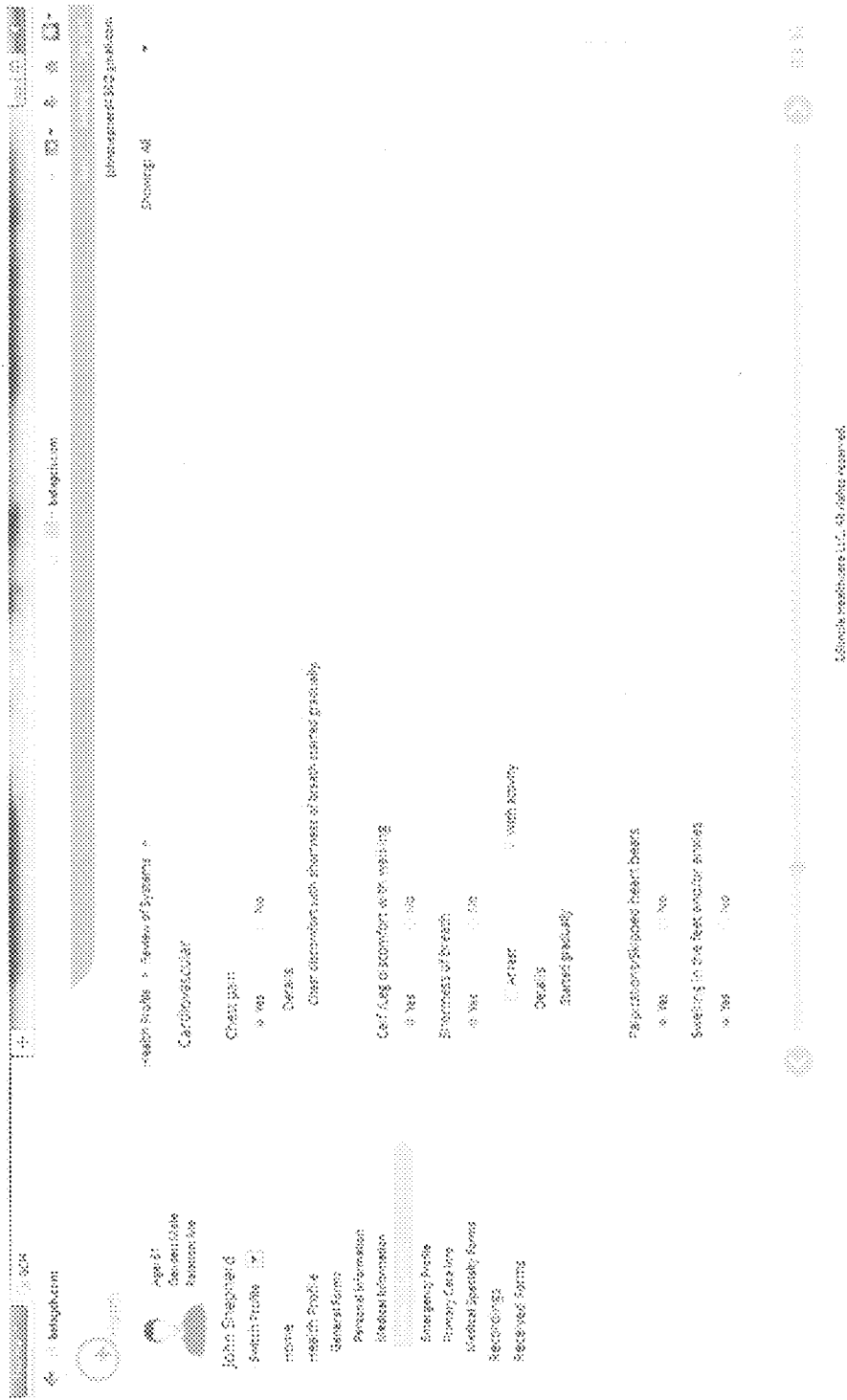
FIG. 26-C

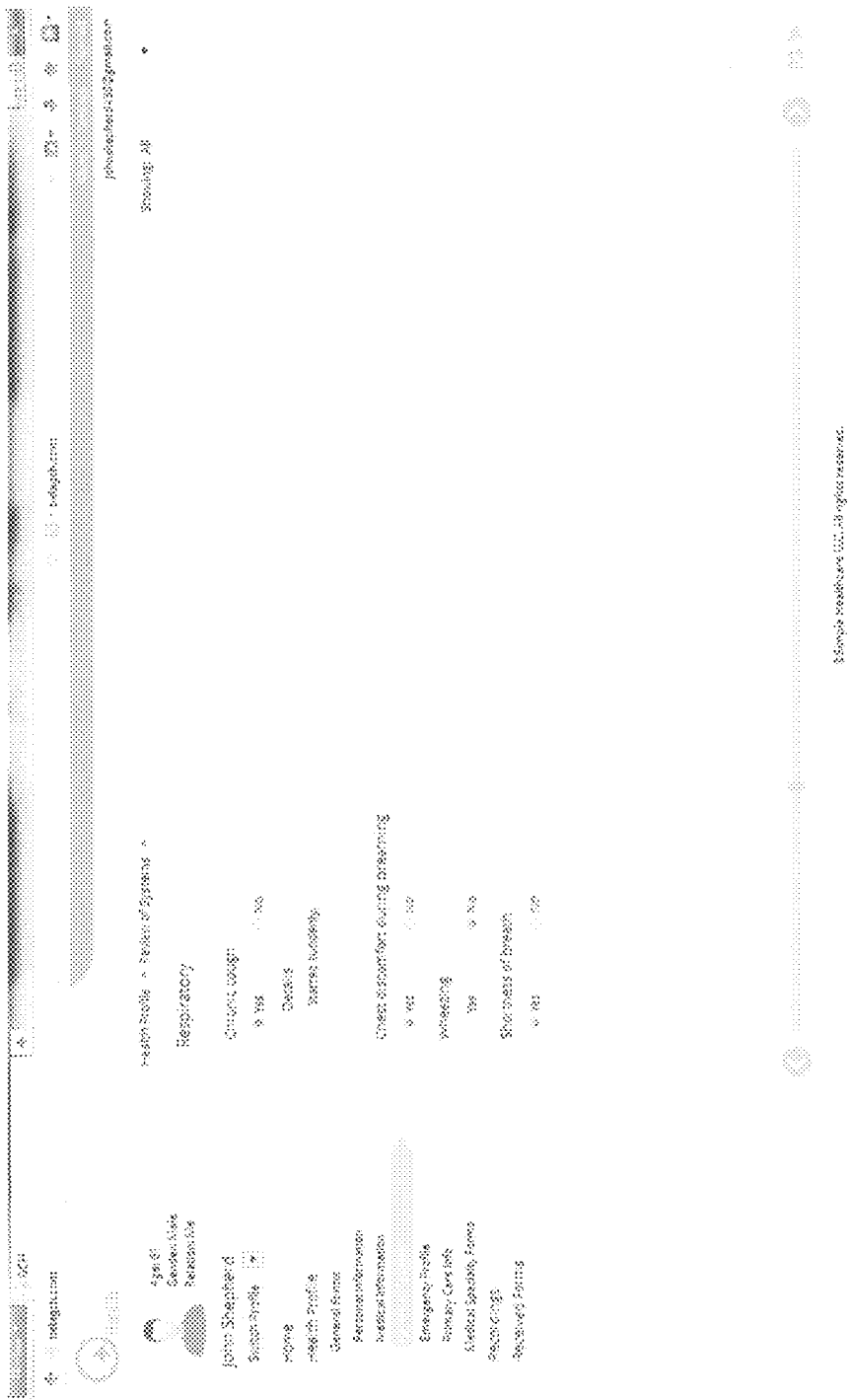
FIG. 26-D

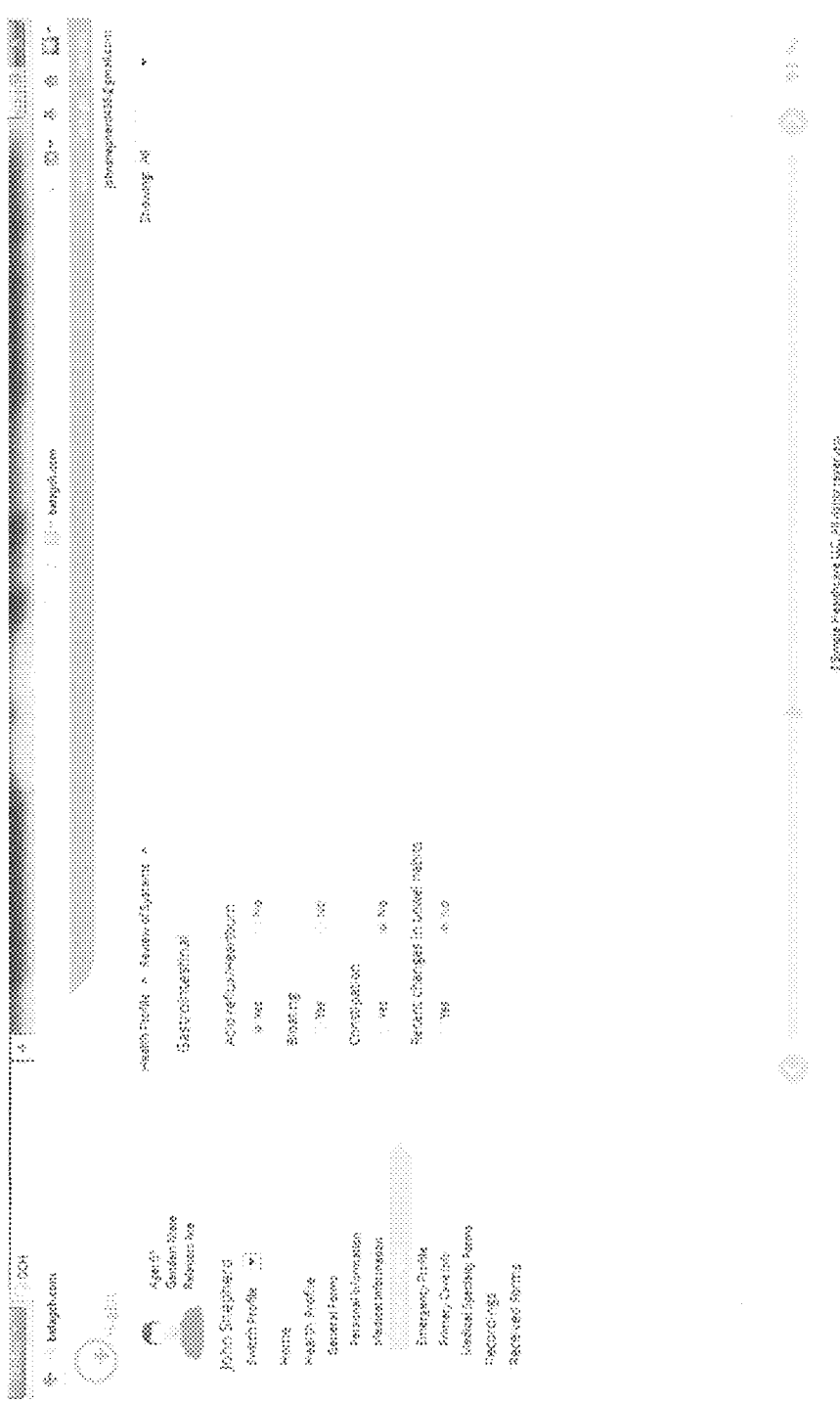
FIG. 26-E

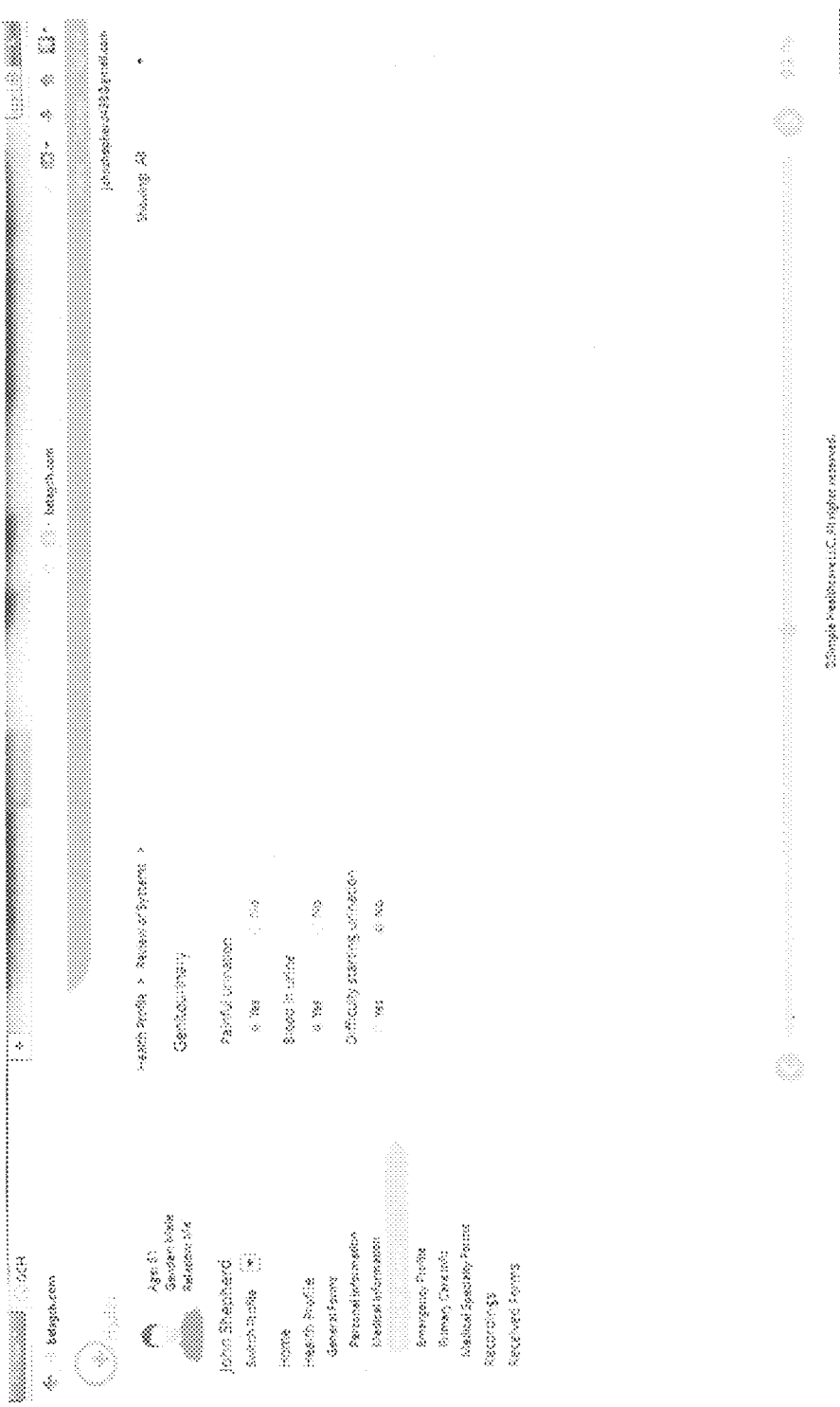
FIG. 26-F

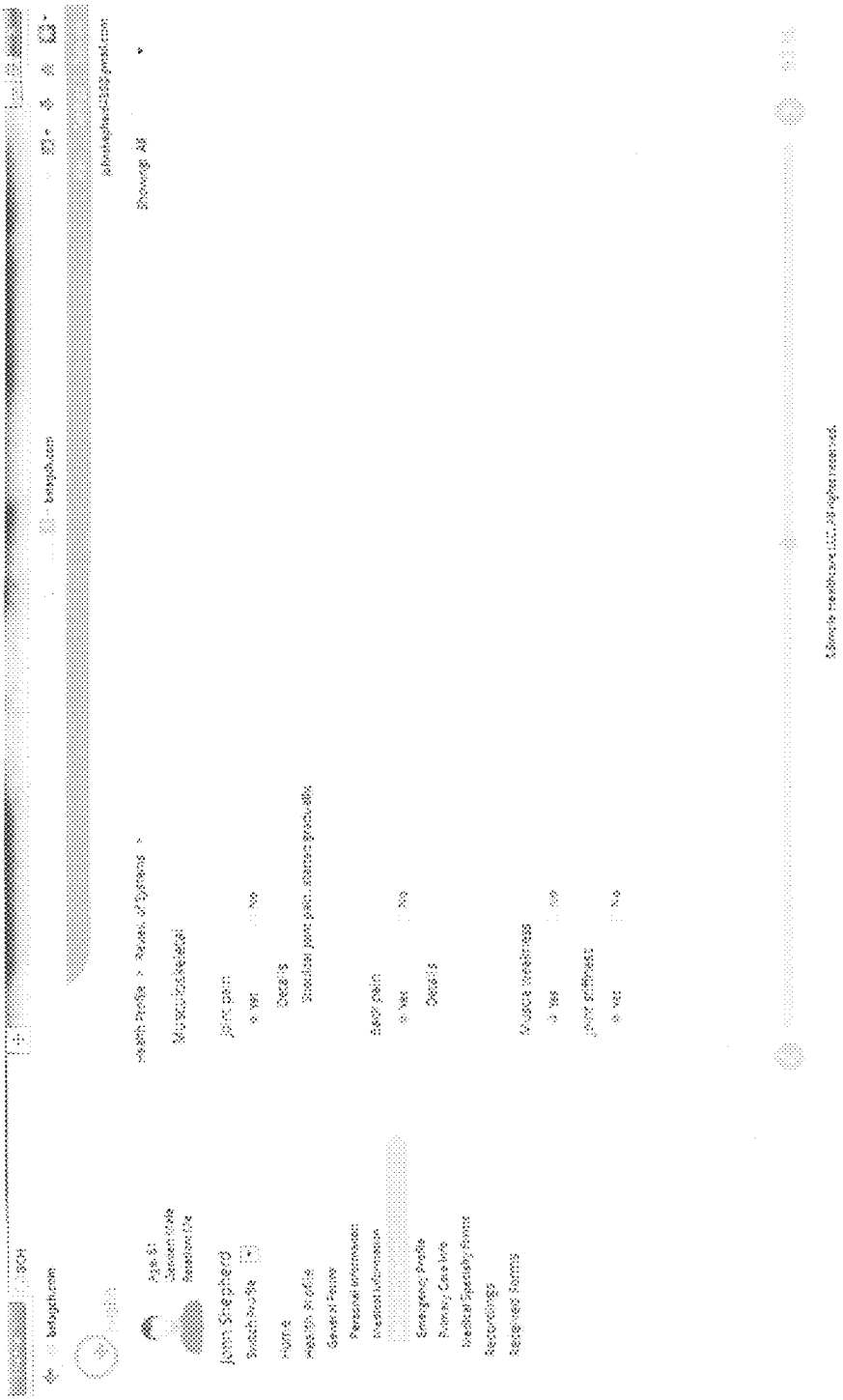
FIG. 26-G

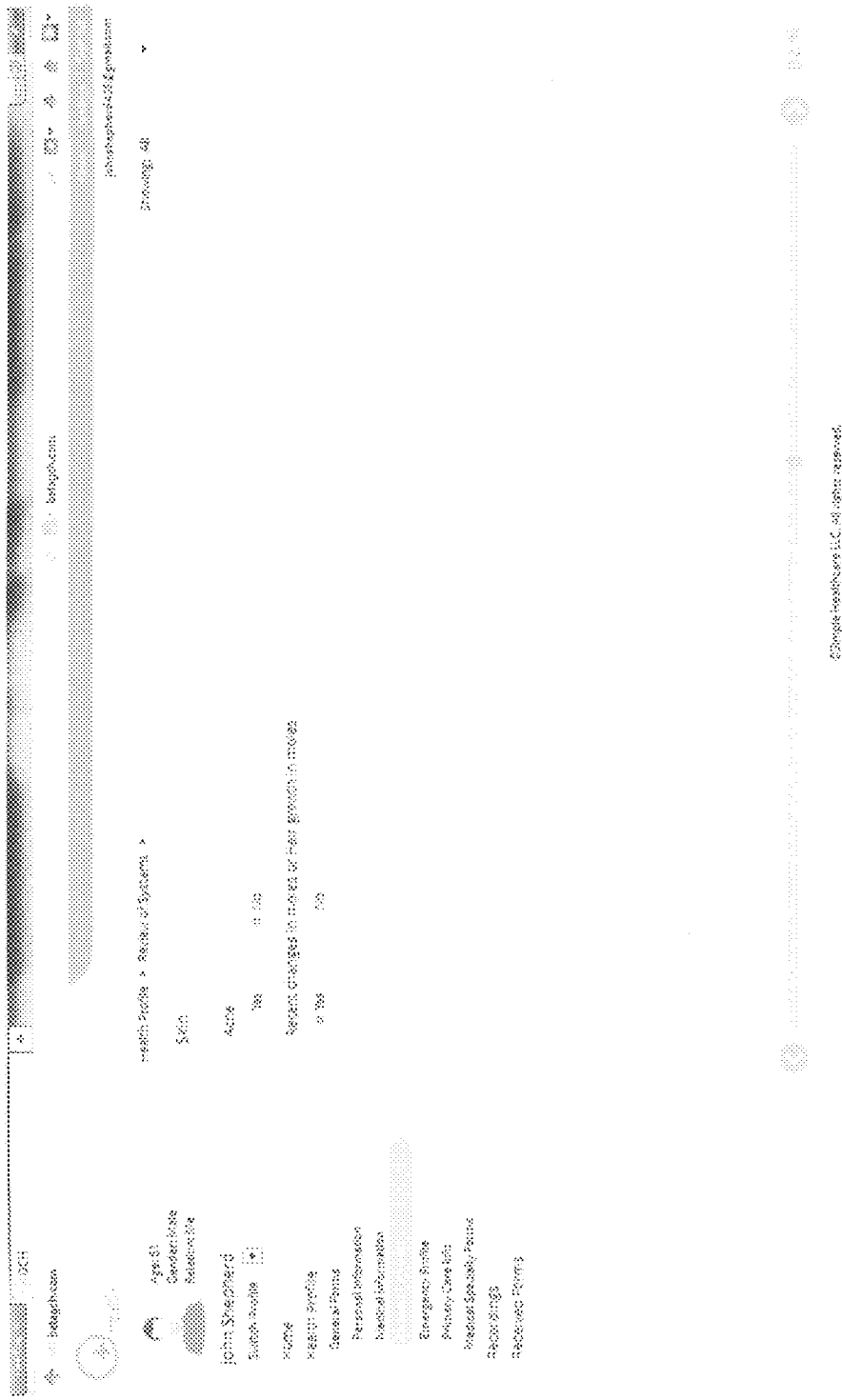
FIG. 26-H

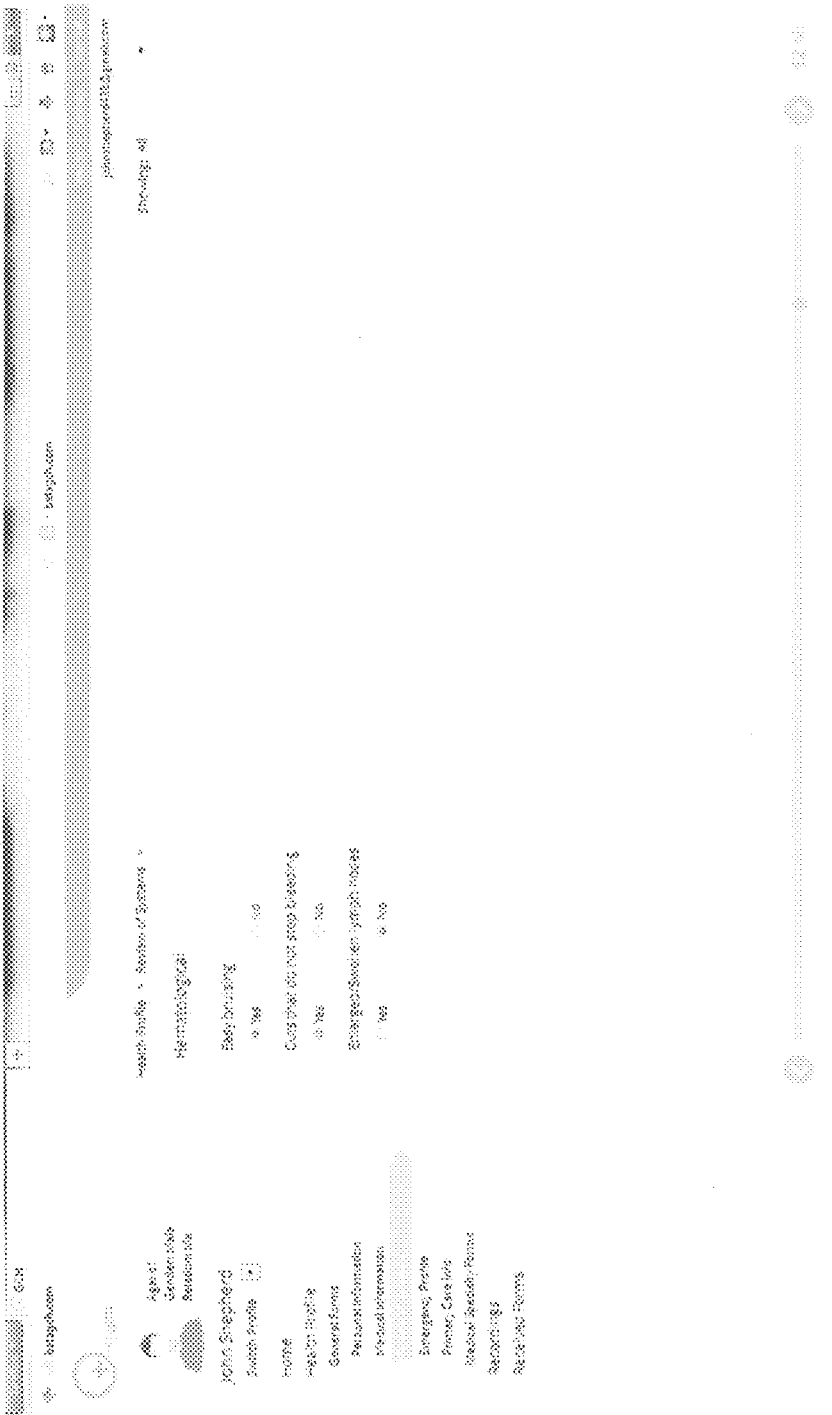
FIG. 26-J

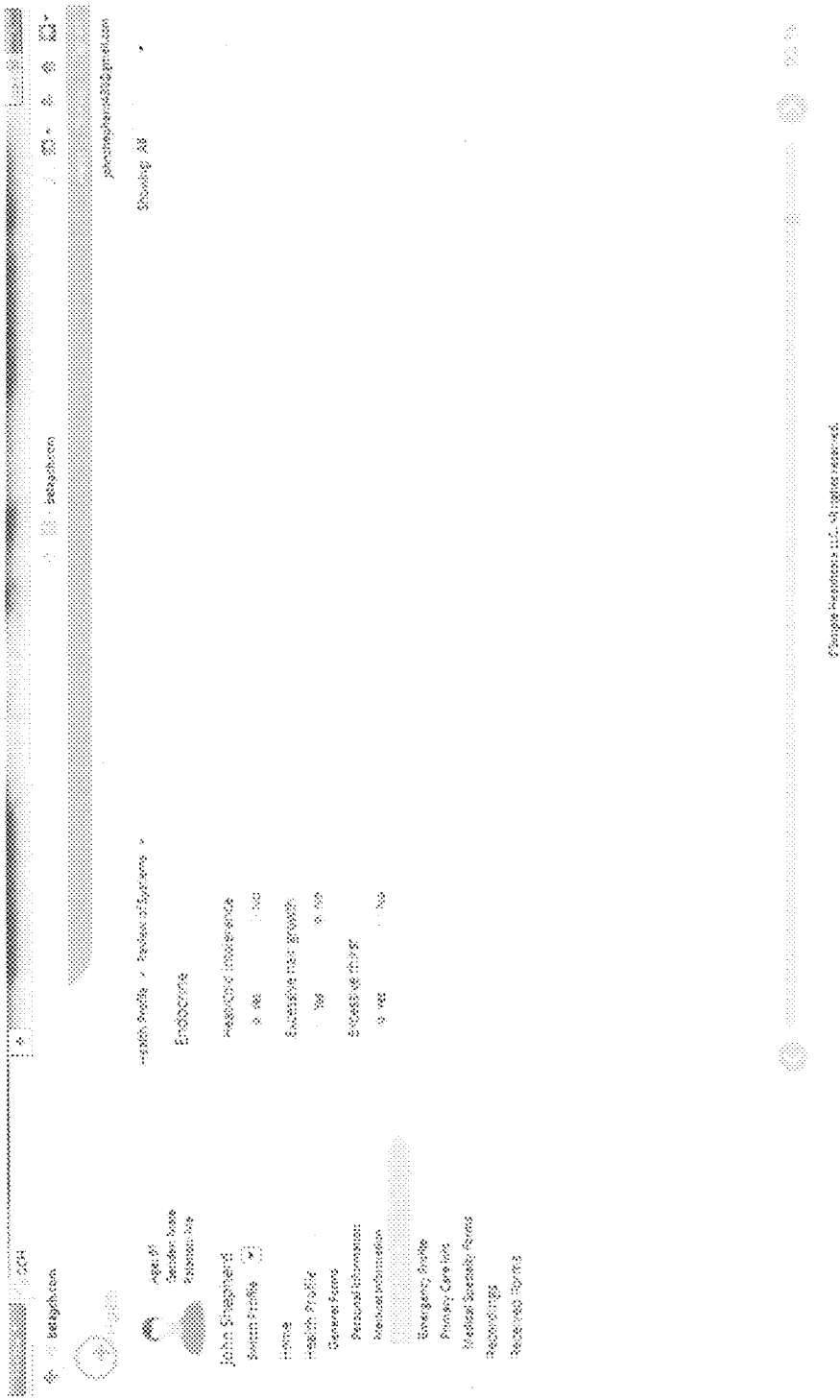
FIG. 26-K

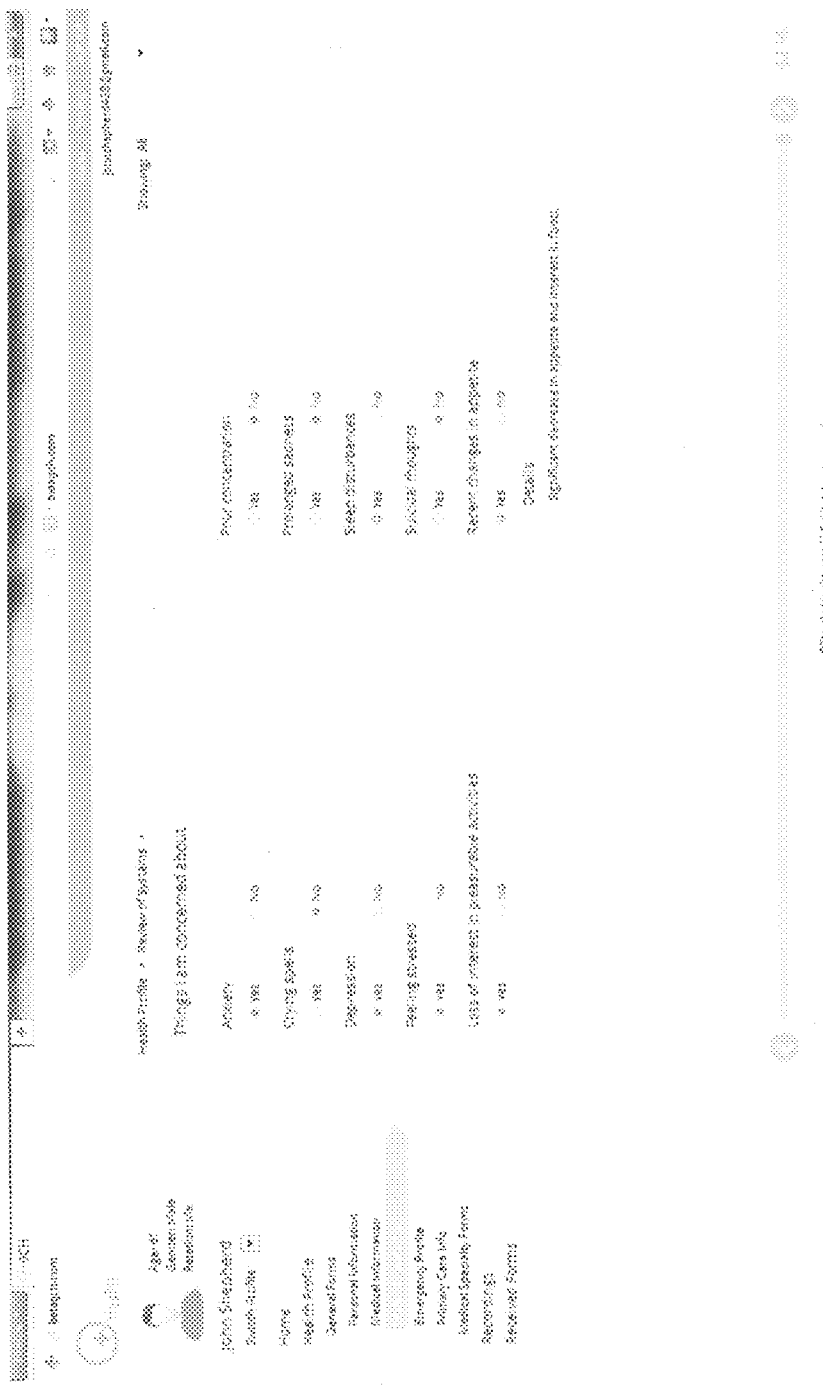
FIG. 26-L

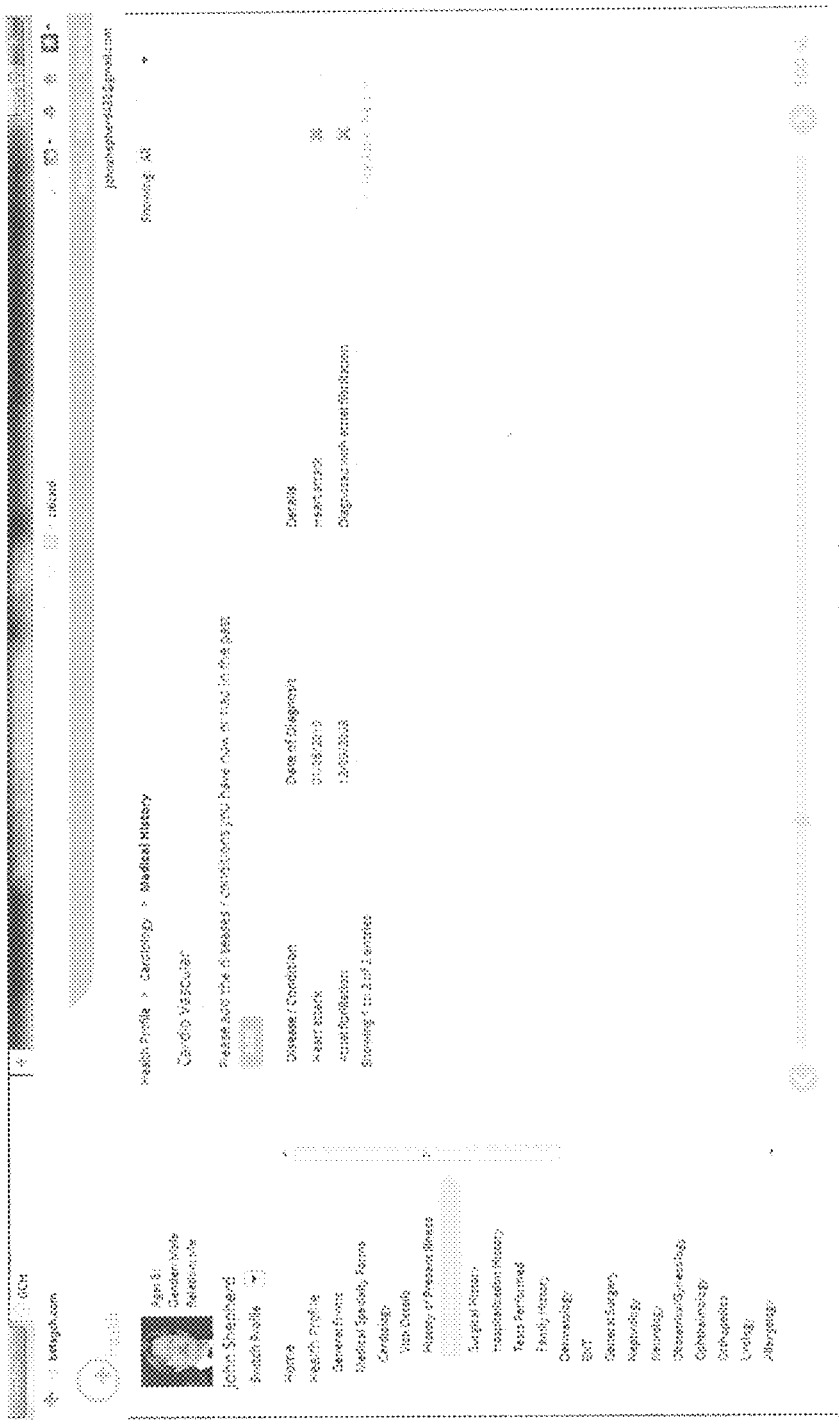
FIG. 27-A

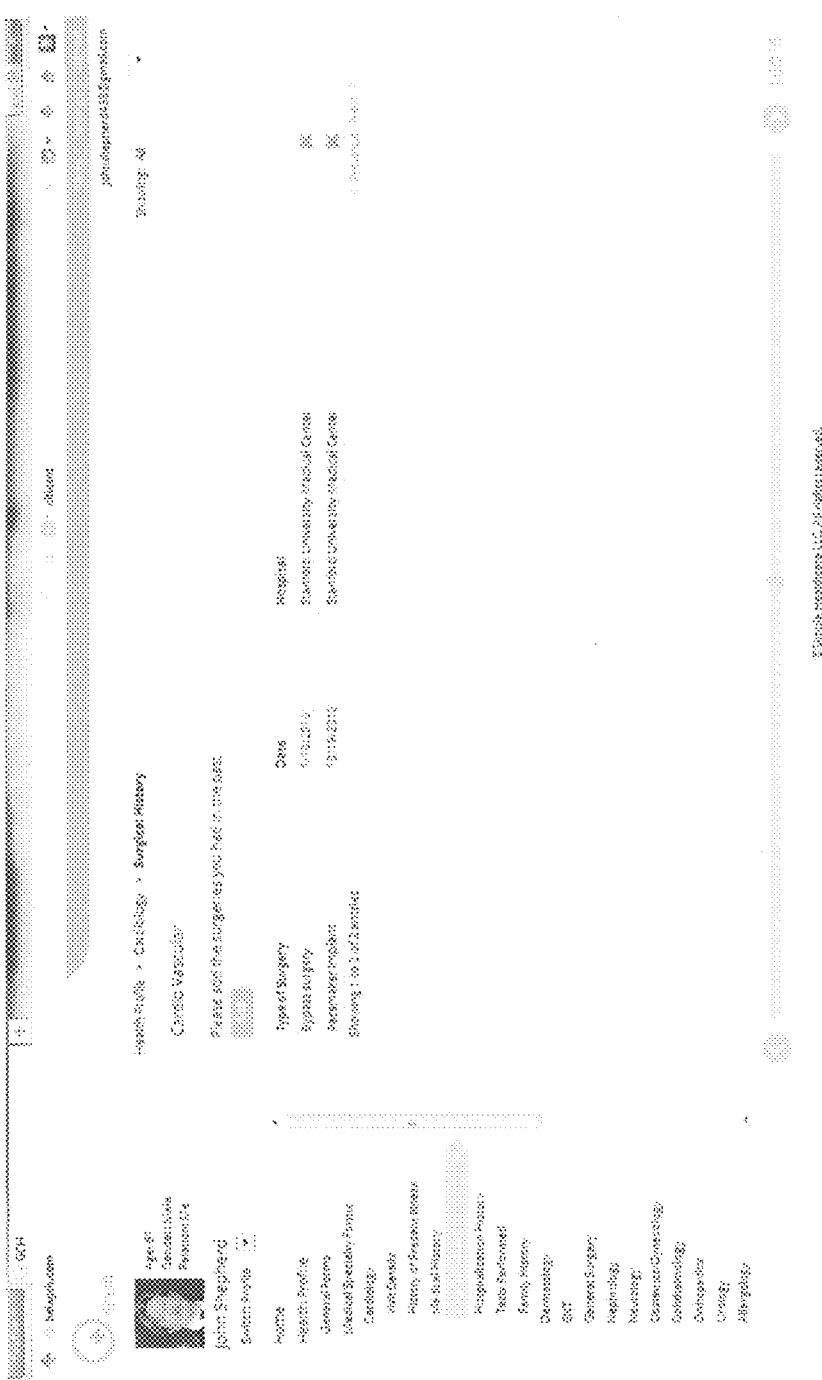
FIG. 27-B

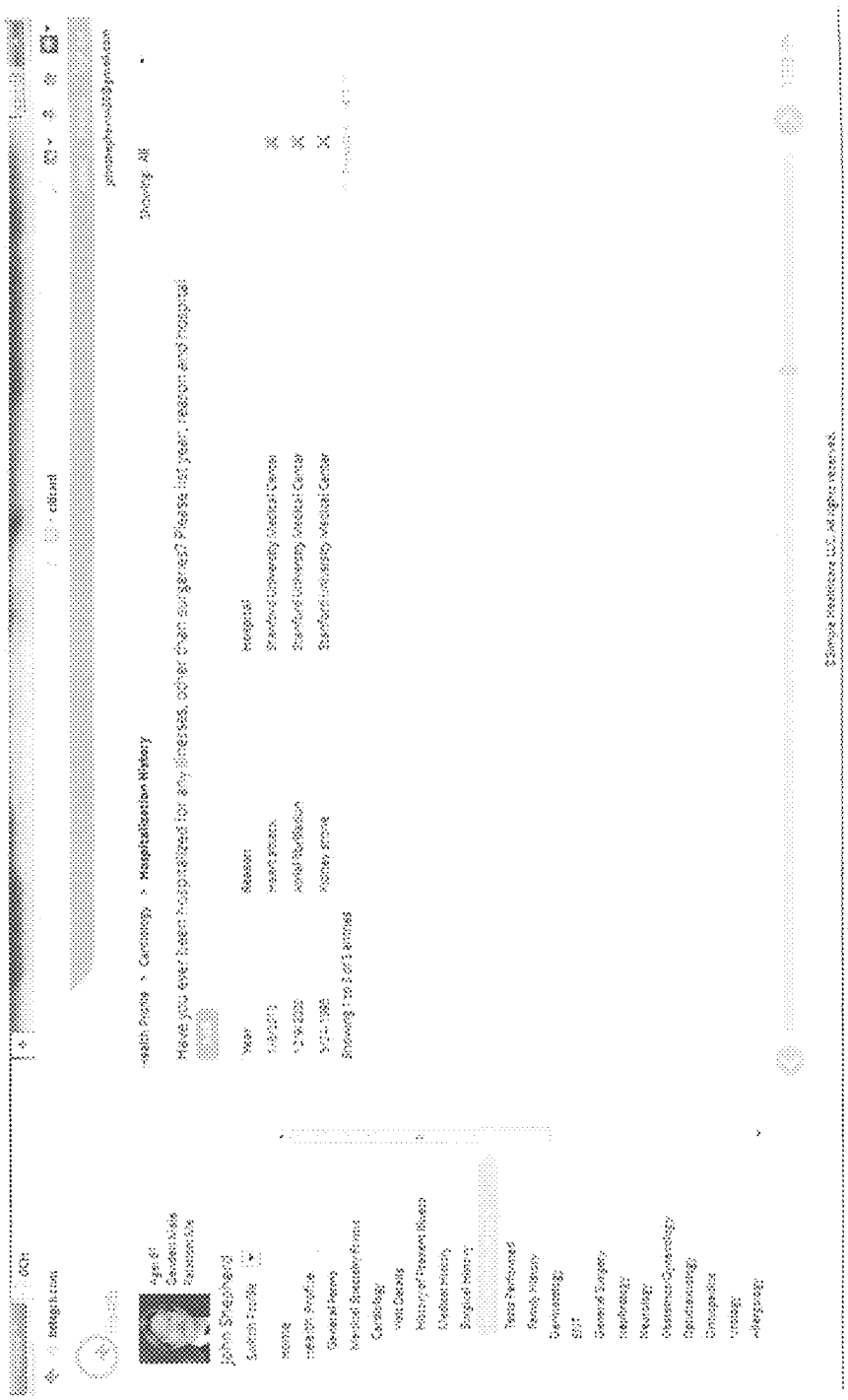
FIG. 27-C

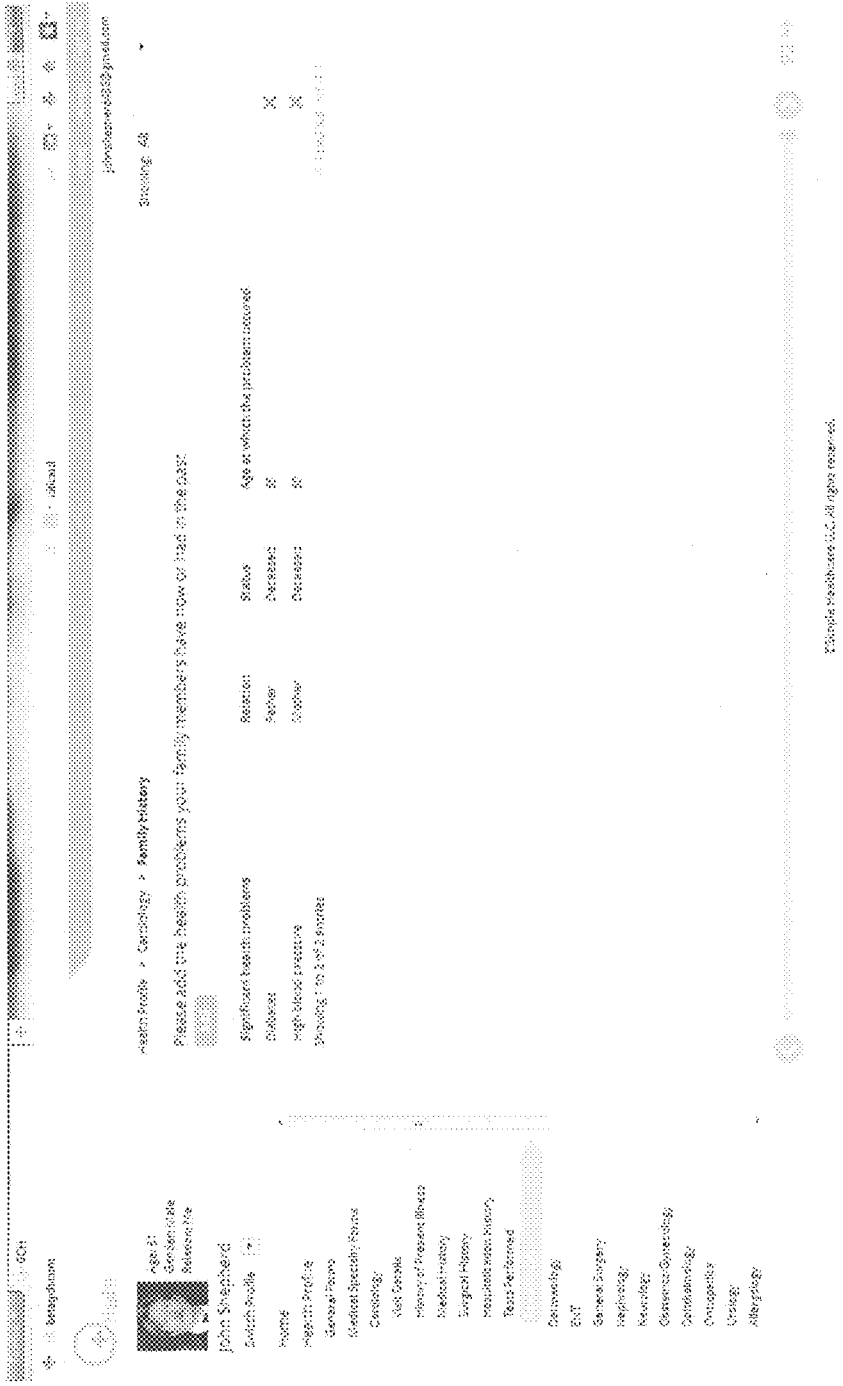
FIG. 27-D

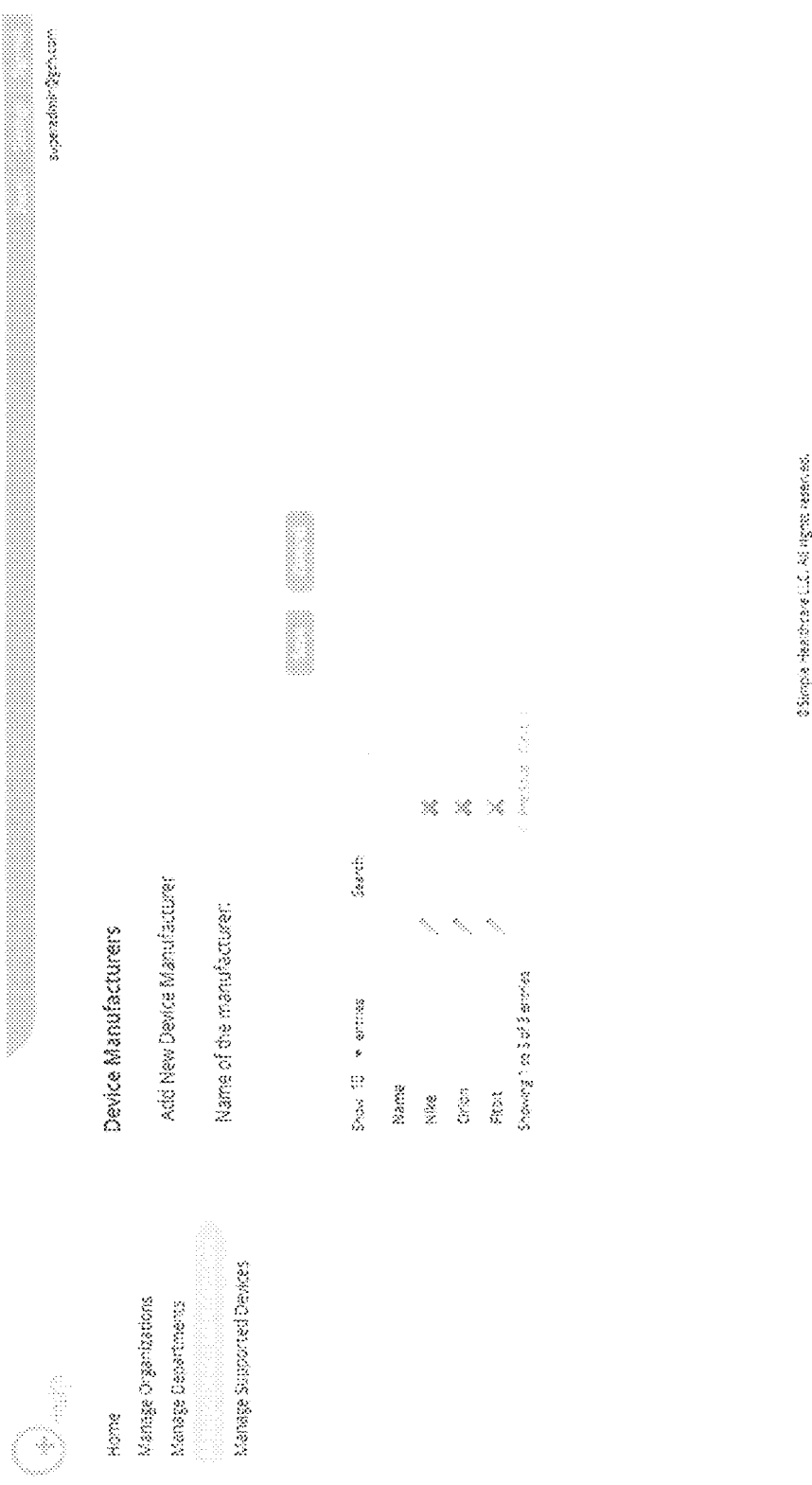
FIG. 28-A

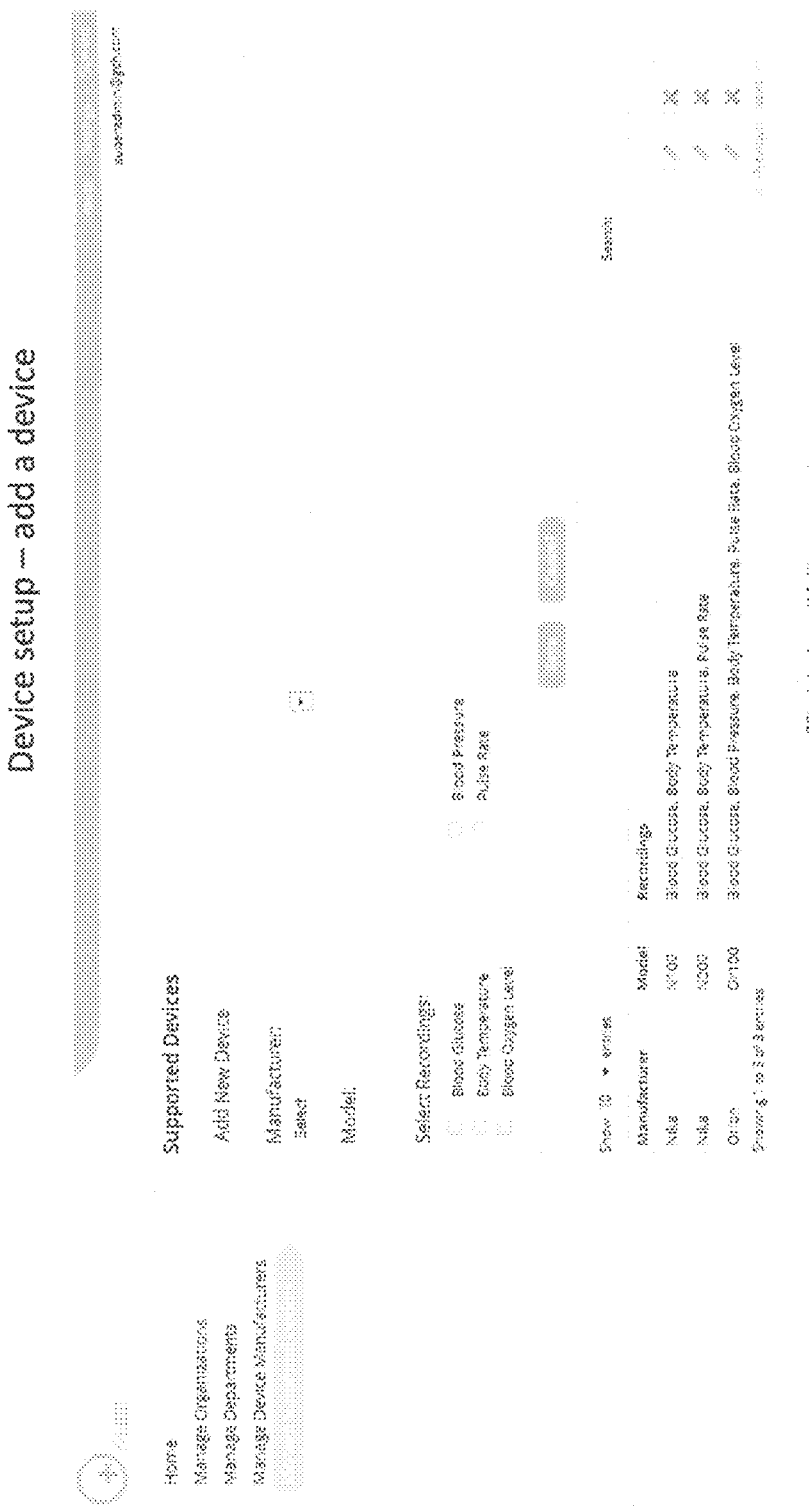
FIG. 28-B

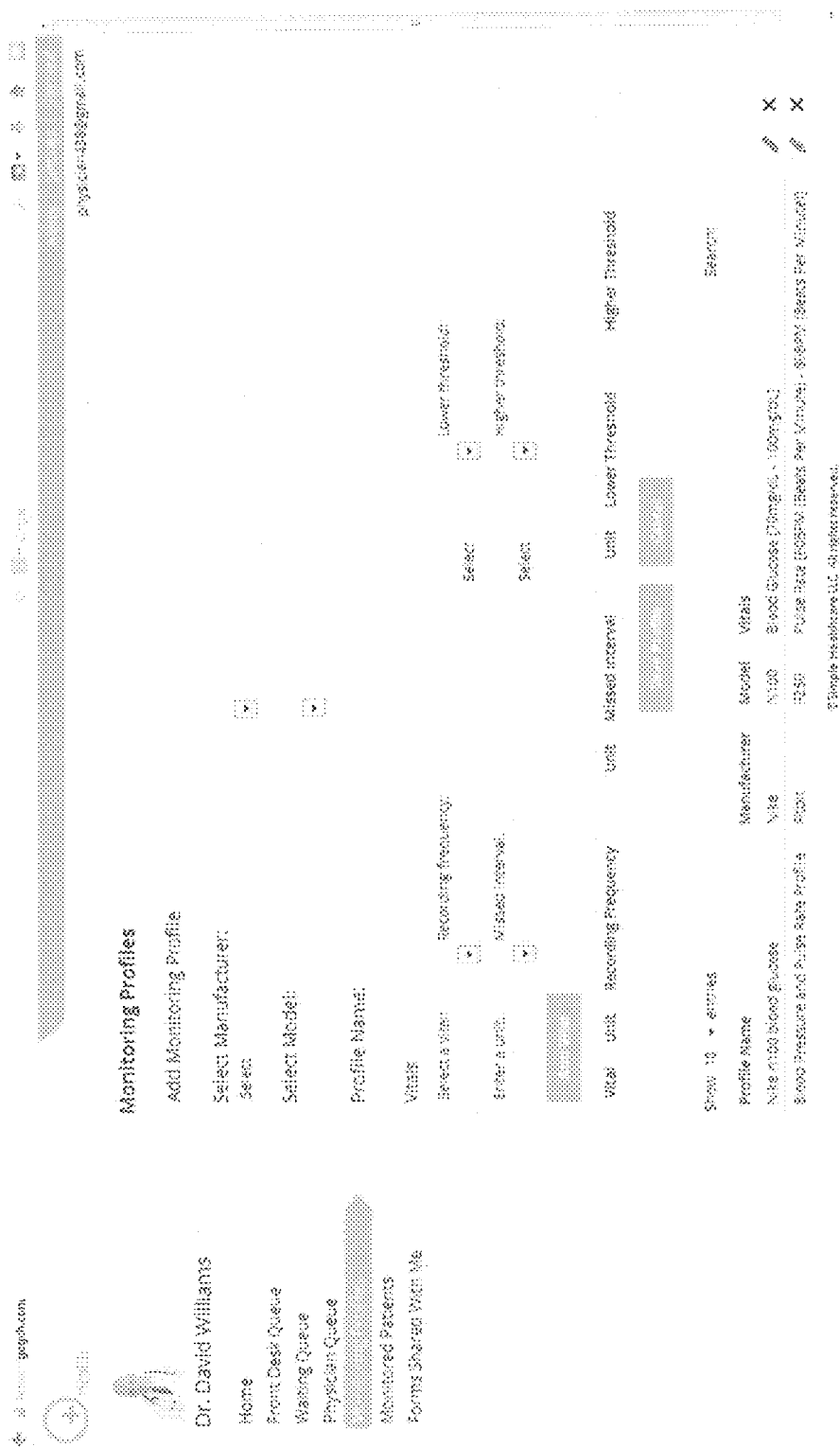
FIG. 28-C

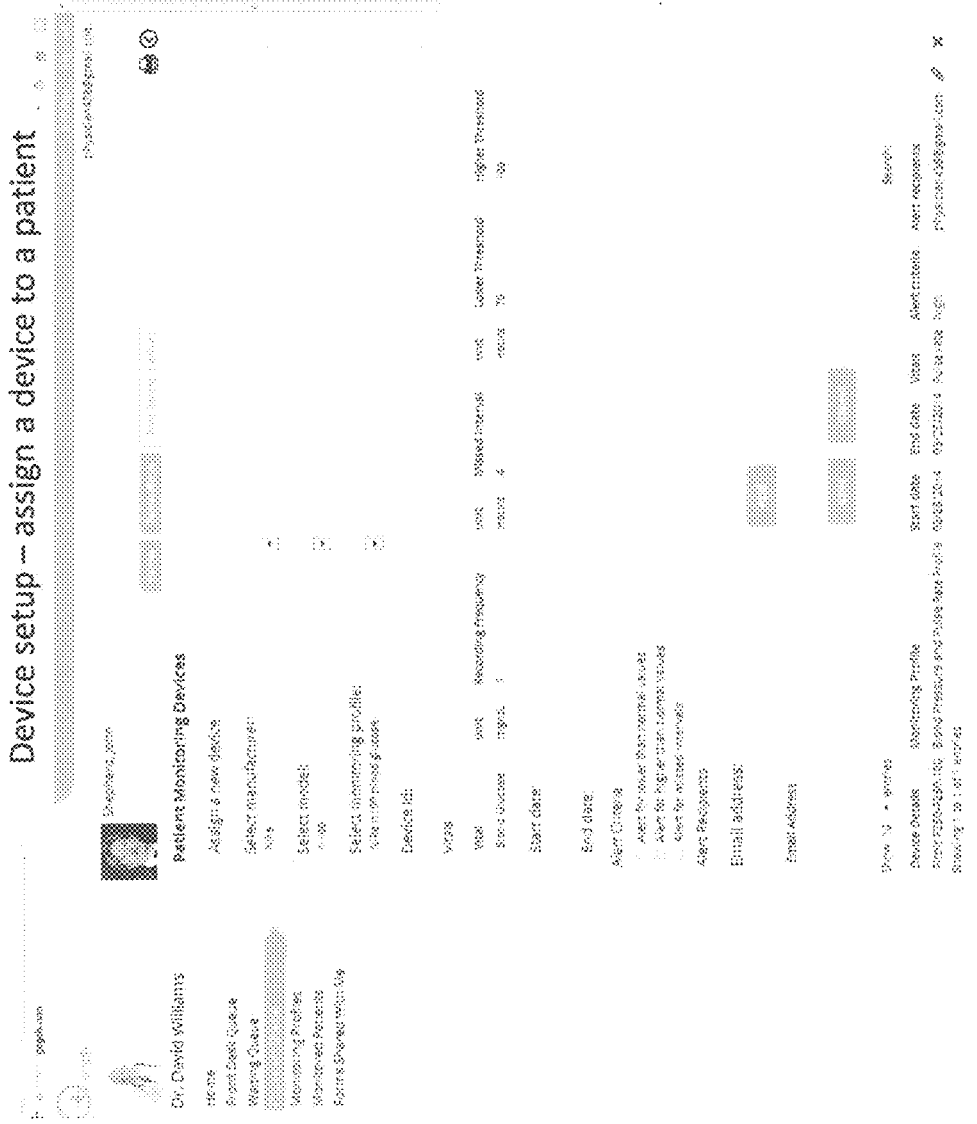
FIG. 28-D

INDIVIDUAL CENTRIC PERSONAL DATA MANAGEMENT PROCESS AND METHOD

BACKGROUND

Information systems are deployed by businesses to improve workflow and organizational efficiencies. Historically such information systems are designed to make it easy for the service providers such as hospitals, financial institutions or insurers to manage the services they provide. In these prior art service delivery models, Information systems are built and paid for by the organization for the benefit of the organization. The organizations' employees or staffs are the primary users of such systems. These systems are designed with input from such users with the focus being to improve their user experience and operational efficiencies. While the customer or consumer (hereafter "consumer" is understood to include customer, patient and other "users") is the beneficiary of such organizational services, the information technology platforms are not primarily designed for the consumer but are designed for the benefit of the organizational employees.

As such information systems have evolved, the organizations have decided to allow the consumers to access some of the information stored in the system. The organization may add services or modules to the system to grant the consumer access to some of the features of the service. These features have grown over time into what is known as self-service delivery of capabilities for the consumers. This is where the consumers begin performing some of the functions, like setting up an appointment, updating personal information like mailing address, or reviewing a bill or making a payment, using the system. Here the consumer is taking the role of an employee to do what an employee was doing with the system to manage a small part of data for his/her own data.

In case of financial systems, this delivery model is seen in online banking services where "consumers" are given self-service capabilities. In healthcare, this model is seen in the Personal Health Record (PHR) and/or Patient Portal module available with some hospitals or practice management systems as an extension of the Electronic Health Record initiatives. Over time, these information systems have performed their intended function of serving the employees and organization well. They help them deliver medical care or other services they provide to their "consumers", patients or customers. They have also made good progress in the areas of self-service for consumers. However, as such organizations deploy and control their own systems, they also retain control and ownership of underlying data and analytics from such data. The customer is required to re-register and re-enter data at each organization to open an account at the institution or to enter as a patient at a facility. The organization may have good business and security reasons to safe guard the data and limit sharing of such information within and outside of the organization. However, sharing of such data across organizations has many benefits for the consumers. These benefits are not achieved when such systems are not inter-operable by design and by choice.

Recognizing these limitations and opportunities, the financial industry tried to develop data exchange standards like Open Financial Exchange—OFX. This standard has evolved over time and it is used by the industry. It does provide some degree of inter-operability with data transfer among the financial institutions. However it has seen limited adoption with limited data transfer control by end-users. Also, for example only, there are no methods for transferring initial account setup information from one institution to another.

The healthcare industry has its own history with Health Level 7 (HL7) and its members that provide a framework and related standards for the exchange, integration, sharing, and retrieval of electronic health information. While HL7 is used by various technology providers in the industry, interoperability among service providers and platforms remains very illusive. Some of the healthcare participants, including government organizations, are spending hundreds of millions of dollars to build information exchanges to share patient data across multiple organizations and various systems within an organization. Such sharing via exchanges has seen limited if any success. There is no accepted standard based practice of sharing data and registering a patient among EHR platforms, hospital management systems (HMS), practice management systems (PMS) and healthcare providers. A patient has to re-register at each facility at each visit to receive service from the provider with various levels of personal information and medical history required to be updated.

In all these attempts at sharing of the data, the focus has remained on the data that an organization collects and what the organization wishes to achieve in terms of delivery of service and benefit to its own business. What data the organization is willing and able to share remains in its control. Such sharing of data, if any, is not designed for the direct benefit of the patients, for example only and not by way of limitation. The patients remain as secondary beneficiaries of such investments in information technologies by the organizations. There is inherent conflict in such system design between patient interests in data and institutional interest in such data. With latest technology, availability of networks and growing understanding and interest by the consumers and patients, it is now possible to change the dynamics of information system model and data ownership and sharing. The following sections describe a process and method to solve this problem and put the patient or consumer in control of information while improving organizational efficiencies and reducing data entry errors. For the first time Applicants' invention makes it possible for a patient and/or consumer to open communication with healthcare providers and other organizations as real-time data sharing becomes available.

With availability of thousands of health related apps for smart phones, consumers are getting unprecedented tools in their hands to keep track of their fitness activities such as exercise and monitoring of calories consumed and more. Personal monitoring devices such as fall detection are increasingly deployed as patient population ages as well as more tech savvy users become users of medical services. However, the limitations of the medical service delivery platforms that are described above only become more pronounced when patient monitoring is recommended or otherwise available for monitoring vital physiological and disease status frequently. Consumer focused platforms like Microsoft Health Vault or Google Health offer patients a place to store personal information made available to them by certain EHR platforms and fitness devices that support their exchange protocol, but the consumer becomes an island of her own information. There is presently no available platform or solution for a patient to communicate effectively with their healthcare providers, for example only, with such information. Similarly, financial industry platforms like Mint or Quicken offer a place for a consumer to aggregate financial data in one place with no effective means to share that data when opening a new account at a new institution.

The Patient Centric Platform

The present disclosure addresses the above problems by describing a platform in a designated computer system developed for the benefit of the patient that changes the dynamics of system design and delivery of information technology for healthcare industry, again for example only and not by way of limitation. One objective of the present disclosure is to provide a method for a patient to interface with healthcare providers using personal computers, tablets and smart phones, for example.

According to this invention, for the first time, the patients are in charge of their own data, both from a data entry point of view as well as for management and use of this data. The patients are not required to 'sign-up', 'register' or 'open an account' manually at each healthcare provider facility each time they wish to receive service from them. According to the present invention, all patient data—both static and dynamic—is entered and/or collected in a patient managed platform that stores all the relevant information needed for the patient to acquire services from any healthcare institution.

Once a patient has created such a data repository, she can update it any time as needed and share the latest information and/or history with any one she chooses at any time. The recipient organization or person can continue to use the platform they may have invested in per the traditional model and simply 'take' or 'accept' the information authorized to be provided by the patient by means of the present invention to improve the quality of data in their own systems.

This disclosure further describes methods for various processes involved in establishing such service for the benefit of a patient and her healthcare services providers. As described more fully hereafter, it will be seen that this same approach works equally well in many other settings for consumers in dealing with other service providers such as financial institutions, insurance services, retail or online stores or educational and governmental institutions.

The present invention further addresses the recording of various readings of recommended or desired physiological and other readings by the patient manually or by using devices that communicate with the invention platform for the patient and for the patient to share selected data with medical service providers. As can be understood by those of ordinary skill in the art, the same approach also works for non-medical recording of data and reporting.

By way of example only and not by limitation, Applicant has identified several benefits of the present invention's patient centric platform for patients as follows:

Benefits for a Patient:
1) Patient builds and retains complete medical history and control of information
2) Patient gets a life time medical history depository with ease and accuracy of data
3) Patient has an easy to use environment that is available online—anywhere, on any device
4) Patient can submit her medical and personal data to selected recipients such as, for example only, her primary care provider online or via mobile device
5) Patient can collect specialty specific data prior to a visit and submit the data online or via mobile device
6) Patient can work on incomplete parts of the requested information at home or while waiting at medical facility
7) Patient has to enter data once or import data from any other platforms once and it remains available to use again and again for sharing with any other providers
8) Streamlines registration and check-in process at the front desk
9) Delights patients by reducing wait-time in front office—easy to register and check-in Benefits for the Healthcare Providers:
1) For patient authorized recipients of selected data the invention provides better tool to front desk staff—easy to admit/check-in patient, easy to see what data is missing and complete it on the spot, upload data into existing systems
2) Provides a better tool to back-office—automatically import that data from the invention in to EHR and no need to type/re-enter data manually
3) Have complete and accurate data while reducing data-entry time and errors
4) Improve staff efficiency and morale
5) Reduce cost of operations without investing in new servers
6) The invention is a fully secure platform, compliant with laws and regulations
7) Enabled by this invention to monitor patient data as "Medical Home" and reduction in hospital re-admission work flows develop in the organization
8) Enabled by this invention to support/participate in sensor based data gathering and services as adoption of such devices and applications become part of a practice
9) Move to $21^{st}$ century interaction with medical office and patient and make the office visit experience match with patient expectations
10) The present invention does not replace existing EHR/PHR/PMS/HMS platforms but enhances the value of existing investment and extends utilization
11) Engages patient in managing healthcare data by providing them a reason to enter it once and use it often The Methods By way of continued description, the present invention is understood by example in the medical arena to provide methods for a patient to request and setup an account with the invention platform (here "platform" is understood to include a computer system in the form of a programmable device configured to utilize a computer processor to process data as described more fully herein), the platform performing activation, completing authentication, verification and identification, presenting personal, general and specialty medical profiles status, recorded reading status, completing personal information consisting of demographics, payments and other information, entering medical history information consisting of immunization, medicine taken, family and social history and other information, entering medical review of systems such as cardiovascular, respiratory, etc., completing primary care data such as prior hospitalization, prior illness history etc., auto selecting right questions based on age and gender of the patient, and tracking percentage complete for each profile. Further, the platform enables continuing completion of information as and when needed for medical specialist specific data such as cardiology, surgery and all other specialties, entering purpose of visit and date of visit, and recording prior tests and, if available, entering or uploading test results. The present invention also provides a method to upload documents like a copy of the patient's—authorized user's—insurance card, identity card, like driver license, health directive proxy or living will. In addition, the invention provides methods for recording of data such as blood pressure, blood glucose level, blood oxygen level, body temperature, pulse rate, urine output volume etc. The present invention enables an authorized user to review the data, print the forms and share selected data with authorized recipients by means of a filtering matrix. This filtering matrix is based on criteria set by the recipient organization for each type of data, and there can be one or more such matrix filter for each organization or each department or service provider. To address the concern of filling out endless forms for each specialty and organization, the forms are removed from the data entry side. The present invention instead presents data requests in a series of questions for each different specialty and once a question is answered in one place, the same data, if requested in another place or form, is used in reading or printing various forms without the requirement of duplicate data entry by the patient. According to one aspect of the invention, a slider control presents data gathering in a series of question and answer modes, with a slider changing color, for example only and not by way of limitation, to show all (e.g. green slider) or only incomplete (e.g red slider) or some other filter based (e.g. orange slider for critical items) set of questions to gather data and improve user experience and data normalization.

Additionally the above described method for data recording may further include devices that reside with the patient and automatically generate readings and use various networking techniques to report the data to the invention platform. This may further include an optional local hub that aggregates data from one or more devices and one or more patients before reporting to the invention platform, thereby improving performance and localization.

On the medical service provider staff side, additional invention methods allow the authorized recipient user role to be defined based on job functions and/or expertise and provides tools to filter patients and organize work queues so as to help those with incomplete data to complete necessary information, receive the patient data and review, print, import or export information as needed, all only as authorized by the patient.

According to another aspect, the invention offers extra security to ensure that only an intended authorized recipient gets the data by providing for use of a token. When a patient sends the data to an authorized recipient healthcare provider, not only a notification—email or other message—goes to the authorized recipient but also a token is generated for the patient/sender, who can deliver that token to the healthcare provider over phone, via text message or in person at the time of visit. This also serves another benefit of protecting the healthcare provider against medical liability on the part of the recipient as by holding the data in a wait queue until patient visit time, and not having access to the data until the token is redeemed. This ensures that the healthcare providers are not assuming responsibility of treatment prior to a visit and avoids liability for any failure to treat or any complications that may occur prior to a visit.

Similarly with real time or near real time frequent recording of device based data, the invention platform offers a method to collect and hold data, and to generate filter based boundary conditions that may trigger an alert to a patient or a care provider or a healthcare professional based on the workflow method selected as will be described more fully hereafter.

In another aspect, the invention further allows a patient to share her full profile with any family member to co-manage their affairs or for a parent and/or guardian to manage data for another person using various profiles, thus making it a data repository for an entire family while at the same time, allowing the data owner to take away profile sharing as and when needed.

According to a further aspect of the invention, the method takes this patient-medical service provider approach to other industries where the "patient" is the consumer who by the present invention is enabled to manage personal data for financial, insurance, retail and other services and respective service providers that are authorized recipients of consumer provided data to offer service, where the consumer no longer has to fill-out forms for each service but only has to enter data in her specialty profile once in one place—her authorized user data repository—all as will be described more fully hereafter.

The above advantages, as well as many other advantages, of the present invention will be readily apparent to one skilled in the art to which the disclosure pertains from the reading of the claims, the appended drawings, and the following description.

BRIEF DESCRIPTION OF THE DRAWINGS

FIG. 2-A and FIG. 2-B are showing patient data flow from the patients to the healthcare providers in traditional environment and in one powered with the innovation;

FIG. 7-A is a high level workflow for a patient after they log in the system to schedule an appointment;

FIG. 12-A shows a device registration and assignment process;

FIG. 18-A shows manual upload of data to the third party systems;

FIG. 18-B shows automated upload of data to the third party systems;

FIG. 19-A shows application of the invention in other industries;

FIG. 19-B shows process flow with the invention in other industries;

FIG. 21-A and FIG. 21-B show user screen sample for patient home pages;

FIG. 21-C shows user screen sample for appointments management;

FIG. 21-D shows user screen sample for CCD upload and viewer;

FIG. 22 shows user screen sample for physician home page;

FIG. 25-A shows user screen sample for medical insurance information;

FIG. 25-B shows user screen sample for social and life style history;

FIG. 25-C shows user screen sample for allergies;

FIG. 25-D shows user screen sample for medications;

FIG. 25-E shows user screen sample for immunization history;

FIG. 25-F shows user screen sample for primary care medical history;

FIG. 25-G shows user screen sample for tests history;

FIG. 26-B shows user screen sample for review of systems—Constitutional;

FIG. 26-C shows user screen sample for review of systems—Cardiovascular;

FIG. 26-D shows user screen sample for review of systems—Respiratory;

FIG. 26-E shows user screen sample for review of systems—Gastrointestinal;

FIG. 26-F shows user screen sample for review of systems—Genitourinary;

FIG. 26-G shows user screen sample for review of systems—Musculoskeletal;

FIG. 26-H shows user screen sample for review of systems—Skin;

FIG. 26-I shows user screen sample for review of systems—Neurological;

FIG. 26-J shows user screen sample for review of systems—Hematological;

FIG. 26-K shows user screen sample for review of systems—Endocrine;

FIG. 26-L shows user screen sample for review of systems—concerns;

FIG. 27-A shows user screen sample for review of systems—Cardiology—medical history;

FIG. 27-B shows user screen sample for review of systems—Cardiology—surgical history;

FIG. 27-C shows user screen sample for review of systems—Cardiology—hospitalization history;

FIG. 27-D shows user screen sample for review of systems—Cardiology—family history;

FIG. 28-A shows user screen sample for device setup—add a manufacturer;

FIG. 28-B shows user screen sample for device setup—add a device;

FIG. 28-C shows user screen sample for device setup—create a monitoring profile;

FIG. 28-D shows user screen sample for device setup—assign a device to a patient;

FIG. 28-E shows user screen sample for device setup—monitor a set of patient;

FIG. 28-F shows user screen sample for device setup—summary of patient vitals;

FIG. 35 shows user screen sample for signature, token and confirmation of sharing.

DETAILED DESCRIPTION

Figure 1:
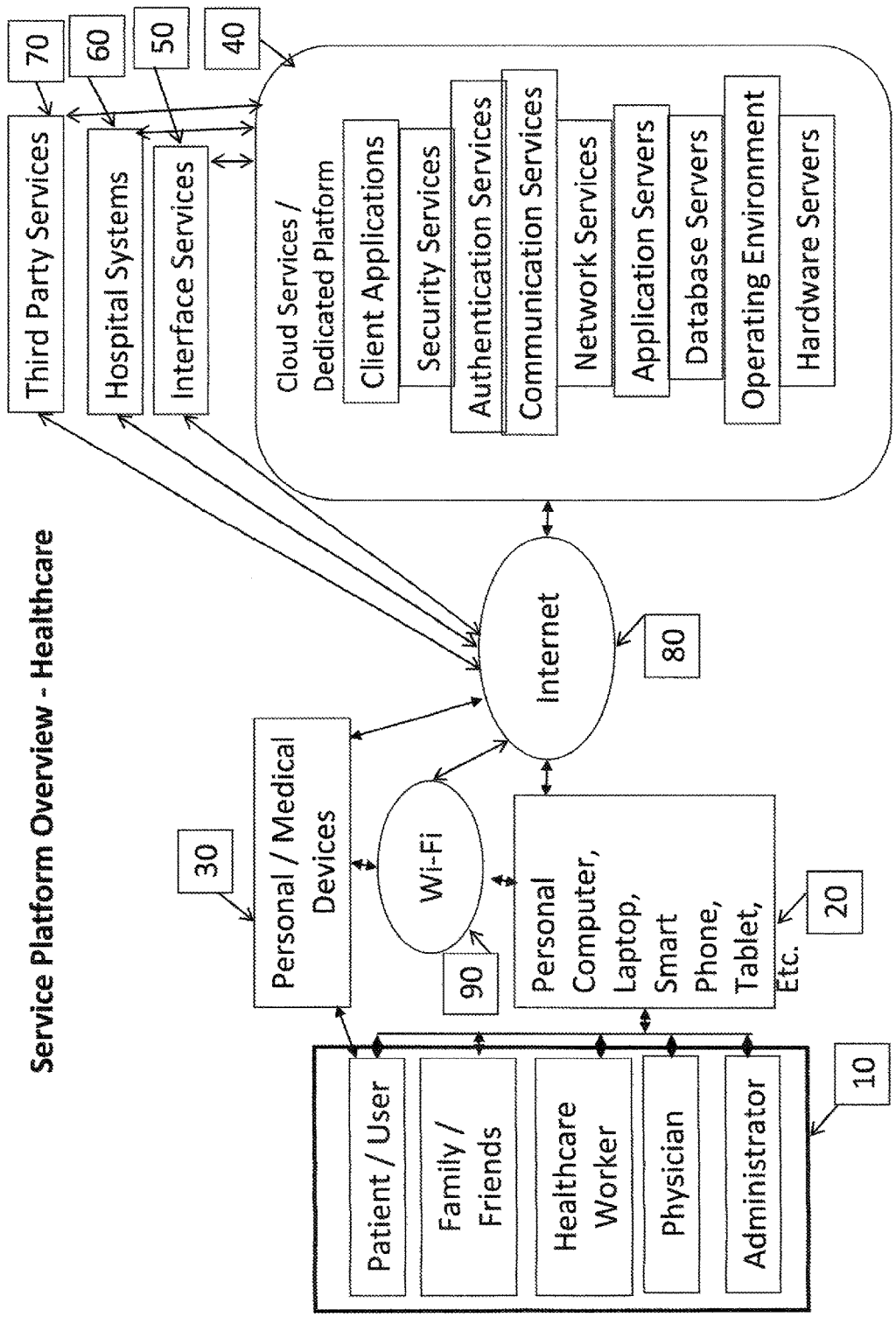
FIG. 1 is a diagram of the service platform overview that illustrates a system for patient to interact with medical service provider according to an embodiment of the invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated. For example, further insubstantial approximations of the process and/or algorithms are also considered within the scope of the processes described herein.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware and software based devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

Overview

The present invention provides, in alternative embodiments, computer systems and computer implemented methods for data management and sharing. Specifically, various embodiments describe a computer system architecture including programmable means configured for medical data management by a patient to share with authorized friends, family and healthcare professionals and such shared data to be used by healthcare professionals, and methods of implementing that architecture. In alternative embodiments, such architecture supports financial forms data, government forms data, educational admission data and so forth for the consumer to manage and share with respective authorized recipient organizations and the authorized recipient organization to use the data with existing systems.

FIG. 1 shows an abstraction of the system where various users (10) of the system are defined as patient, friends and family or associates, healthcare staff, physician or manager of a practice and administrator of the facility or service. These users access the services provided by the invention using devices (20) like personal computers—a desktop or a laptop, mobile devices like smart phones and portable devices like tablets and transformers, independent of what manufacturer or operating systems they use. These devices connect to local Wi-Fi network (90) as well as Internet (80) to connect to services provided by applications using the present invention. These applications could run on a dedicated hardware/software platform in more traditional fashion but are as likely to run on cloud services (40). Such a platform will consist of hardware servers running various operating systems and creating virtual servers, that will provide data base servers, application servers, interface servers providing network services, security services, authentication services, load balancing, streaming, and client services which will drive the user experience and application logic. Remote monitoring devices like pedometers, heart rate monitors, blood pressure monitors, smart watches or belts or sensors, various medical measurement devices (30) are used by the patient to gather biometric or other data and some of these devices may communicate with other devices over a Wi-Fi network and/or Internet to connect to the service provided by the present invention to report routine or exception data. This data is analyzed by the client services in the cloud or dedicated servers (40). The application defined in this invention also communicates with third party interfaces (50) which allow integration with external systems to exchange relevant information such as identity information, reading for other platforms such as prescription or lab test results etc., exchanges data with hospital or healthcare provider systems (60) so that a new patient can be registered in the existing systems or an existing patient of those systems may be verified as such and information may be exchanged or updated as needed, as well as many third party platforms (70) such as may exist among many providers of healthcare services or monitoring devices or dispatch services or communication services and so on. With these external interactions, important data may be sent to those systems as well as existing information may be imported in to the platform of the present invention to provide additional services which may be rules based analysis, or decision support, reminders, alerts, or follow up activities and so on.

The focus of the following detailed description along with the help of the rest of the diagrams is to explain these client services and the logic of the present invention which can be implemented using modern software development methodologies such as using object oriented paradigm. As a result the following workflow diagrams are not always shown in traditional structured programming language oriented flow charts but instead may show functional objects and entity relationships.

FIG. 2-A is used here to give an overview of the service model according to one embodiment of the invention. In this model there are two main entities: I) (100) the patient who accesses the "system" (as the present invention occasionally will be referred to for brevity) via a computer, tablet or a phone type device, for example only, as explained above, and ii) (200) the health facility staffs and physicians who access the system via a computer, tablet or phone. Thus, there are two main "users" of the system, "authorized users", patients or consumers, who control their personal data, and "authorized recipients", users such as healthcare providers or office staff that are allowed access to selected data by the authorized user patient. While others may "use" the system, only authorized users may access their personal data unless the authorized user permits an authorized recipient access to data selected by the authorized user. The object of their interest in this interaction among the patients and healthcare providers is the patients' personal information, medical history and records of health related data. As this description continues, it will become clear that a difference in this interaction in the stated invention from those of the prior art is control and flow of such information. According to the present invention the necessary information is created only once and is managed by the patient to be shared as often as needed with one or more authorized recipient healthcare providers. Patients retain control of their data and share it with any one they desire to share it with. As a result, a patient when going from one health facility to another health facility or healthcare provider is able to check in with any facility without having to re-enter any data. The patient selects the data she wishes to share with a given authorized recipient facility and sends that to that facility, privately and securely, keeping it compliant with HIPPA regulations, while avoiding data entry errors or dependency on anyone else for entry of her data. According to the present invention, the patient is also able to share selected data with other family members or friends, if she wishes them to have access to her data, either for ongoing care or in case of any emergencies. Similarly with proper authorization, the patient by means of the present invention is able to enter, edit, and manage healthcare data for other family members in the system so that if she is responsible for anyone else in the family, she can manage that data for medical or administrative purposes just as effectively as she handles her own data.

The FIG. 2-B helps explain the system of the invention from flow of the information expanding upon the last figure to show that the object of interest—the patient data entities (300)—personal profiles, health records, readings, etc.—are being shared by the patient with authorized recipient healthcare providers. Once the providers receive them, they can be used in various ways. One common application will be for them to be applied to or imported into the healthcare provider platforms (500). As shown here, there are at least two options (410) and (420). The first one (410) is a fully integrated and automated approach in which an interface adopter or translator is used to take patient provided data (300) and to load it in the healthcare provider platform (500). Another approach is for the authorized recipient health facility to receive data by accessing the invention platform directly and either review it there or print the information and use it or even manually load (420) the data into their existing platform (500). The automation approach is driven using the interfaces provided by the platform of the invention where data can be distributed to many systems at the same time if so desired without any work on the part of the healthcare worker by means of a translation matrix that is explained more fully hereafter. When the authorized recipient system is unwilling or unavailable to receive the user selected data in an automated or semi-automated way, the manual approach requires the healthcare provider to continue using their existing system for data entry. Nonetheless, they can see upfront that the patient has provided complete data and what if anything has changed since last time and the data is available in electronic or print form and not hand written on paper where it could be incomplete or difficult to read.

Figure 3:
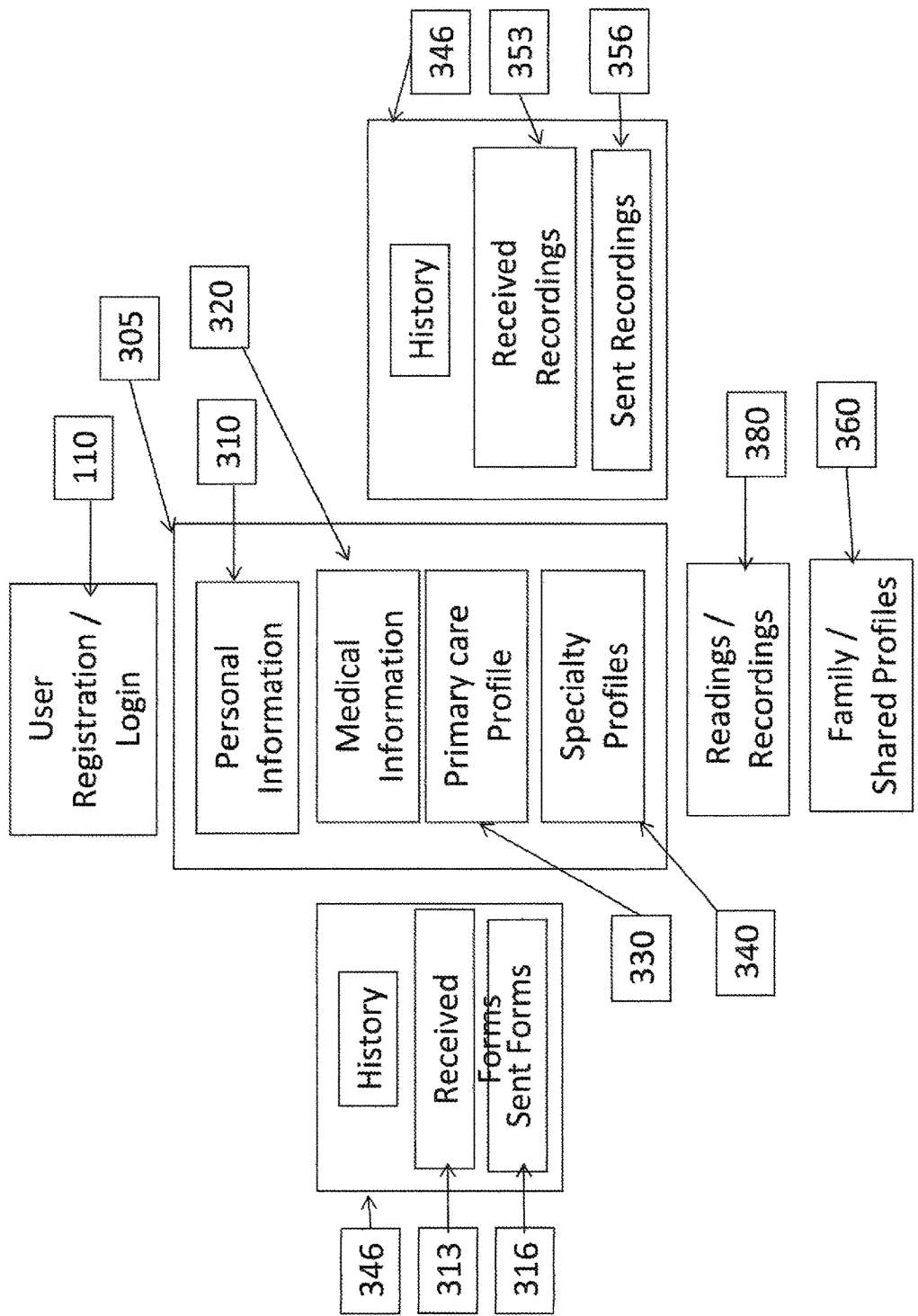
FIG. 3 is high level workflow from patient login to various actions by the user using the invention to create, store, edit and share information.
Figure 20:
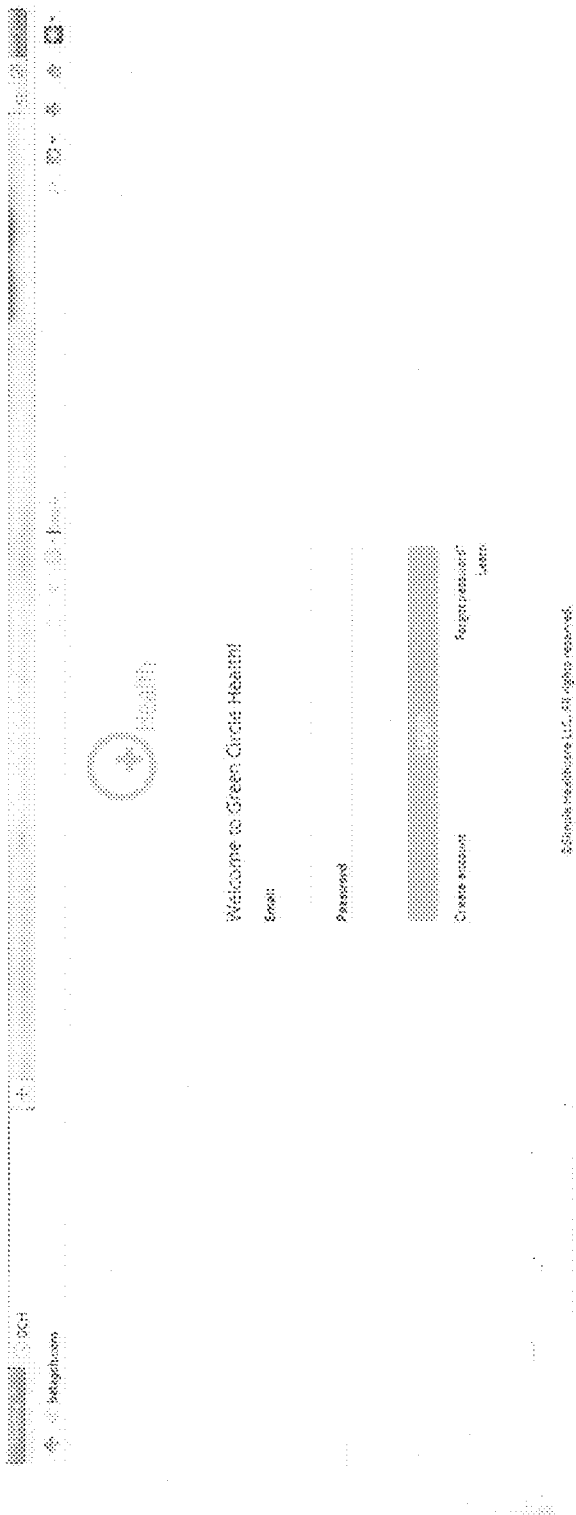
FIG. 20 shows user screen sample for user to log in the system.

By way of example, interaction with the present invention begins with a patient registering for the service on the platform provided by the invention. In FIG. 3 this registration process is defined in block (110) which will be further explained later. Once a patient is registered in the system, the patient logs into the system as shown in user screen in FIG. 20 as an "authorized user" and arrives at the patient home page that is shown in sample user screens as in FIG. 21-A and FIG. 21-B. From here the patient can create a medical profile (305) consisting of personal information (310), medical information including review of systems (320) Primary care profile (330) and Specialty Profiles (340). The patient is also able to create necessary profiles (360) for family members or others. The patient has access to, and control of, collection of biometric readings using devices that communicate with the invention platform in real time mode or at periodic intervals or may do the same using manual data entry when the devices do not communicate with the invention platform (380). The patient may select appropriate information (316) and (356) to share with family members, friends or one or more healthcare service providers and then share the selected information in a manner more fully described herein. Similarly she may receive shared information (313) and (353) from other family members as they share it with her. All user interactions are captured in audit trail while the shared information is also available for future reference in a history log (346).

Figure 4:
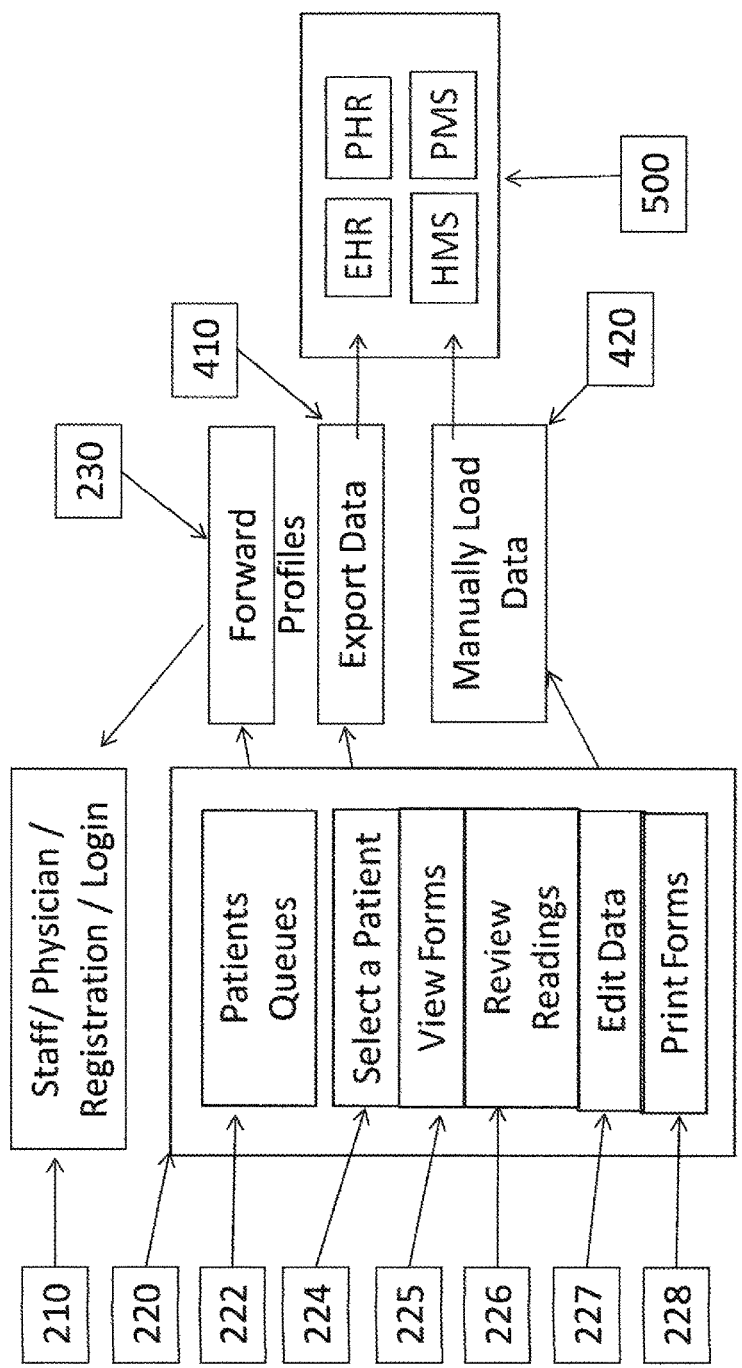
FIG. 4 is high level workflow for medical staff from login to various actions by the user using the invention to review, complete, route, print, export, etc. the shared information.
Figure 22:
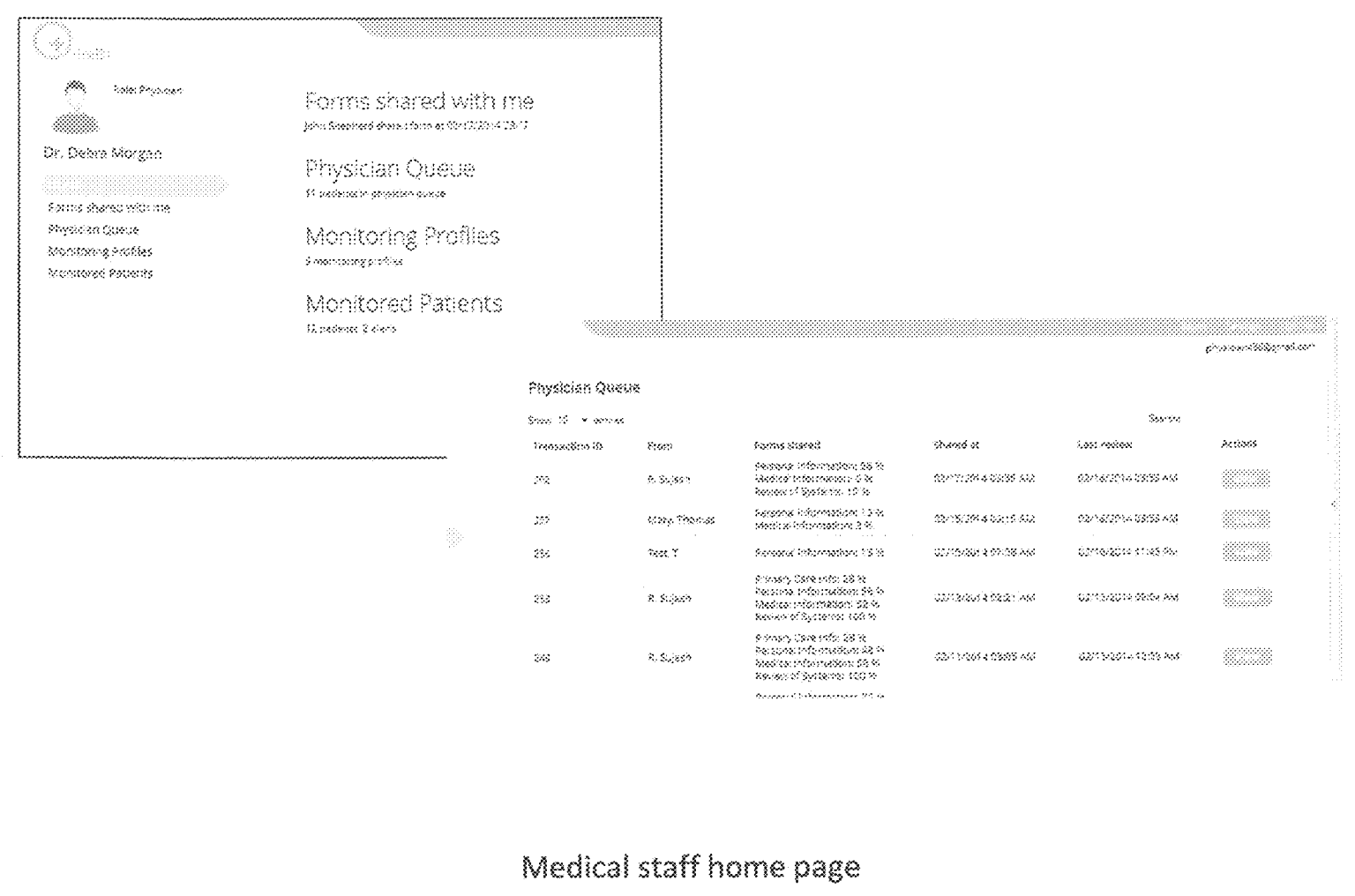

Similar to the above described patient interaction with the platform of the present invention, there are facilities provided by the platform for authorized recipient medical staff to perform various services. While in one embodiment of the invention in this platform, the staff may register directly with the service as shown in FIG. 4 as block (210), in another configuration, it is possible that the medical facility system administrator or manager may create such users in the system and assign them roles and privileges to access the platform for intended purpose as per respective user authorization level. Once such a user logs into the platform using a login facility similar to that shown in user screen at FIG. 20, the authorized recipient medical staff user is presented with a home page of medical facility staffs or physicians appropriate for their user access right as shown in a sample user screen in FIG. 22 for a medical staff. One of the primary reasons for such an authorized recipient medical user to log in is to receive the shared data—forms or recordings from monitored patients—via the invention platform. They can then process the data using their existing platform (500) when data is loaded in that platform automatically (410) or manually (420). From their home page (220), a number of actions are possible for them to take. They can use the platform of the present invention to handle the data where they can manage the patient queue (222), select a patient (224), view forms (225), view recordings (226), edit forms and recordings (227) or print them (228). They can forward the data to another entity (230). In short, this is a dash-board for the authorized recipient healthcare providers to organize their workflow to provide better service. The platform of the present invention allows the authorized recipient medical service to augment the workflow of an existing system without replacing or re-engineering that pre-existing healthcare provider proprietary system.

Next the workflow processes enabled by the present invention platform to perform each step involved in delivery of such services is described.

Figure 5:
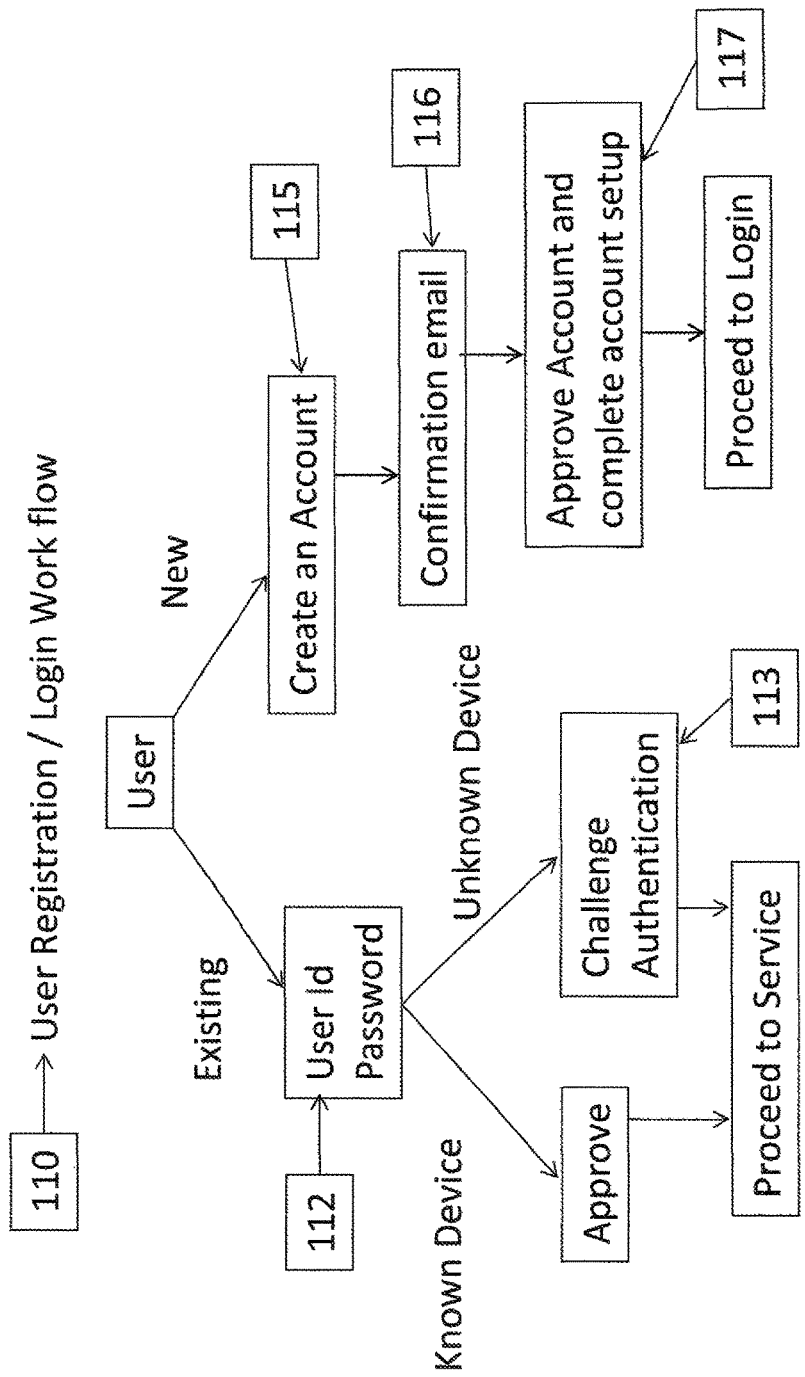
FIG. 5 is a workflow for creating a new user or logging an existing user in the system.

In FIG. 5 the first workflow process (110) is identified for logging into the system (112) of the present invention and for creation of a new user account (115) where, in this example, the user is a patient. A new user patient begins use of the platform of the invention by selecting the "Create an Account" option where the patient provides an unique email id, selects a valid password, enters some information like name, date of birth and accepts terms of service to use the service of the present invention. The system creates a user record and sends an email (116) to the new applicant so as to validate the user email id. The user returns to the system with the information in the email and completes account setup (117). In addition, the system records device identity and network access profiles for the user to improve security and protection for the user as well as the platform. The user establishes a site validation phrase and/or picture and challenge questions and responses that could be used for additional authentication as well as for password reset function. Once the user account is activated the user becomes an "authorized user" and the now authorized user uses the login sequence (112) to enter the platform and use the service of the invention. According to one aspect, the system evaluates risk associated with each login attempt and adjusts its security barriers accordingly to ensure that only authorized users may access and control data in the data registry for a particular authorized user. Parameters for such adjustments could be user id, user login attempt count, last successful attempt time, device signature, network address, inactivity duration, history of previous access, history of authentication management, level of engagement with the service, in-band and out-of-band authentication settings and validation, and so on. E.g. email or SMS are used for out-of band validation.

Figure 6:
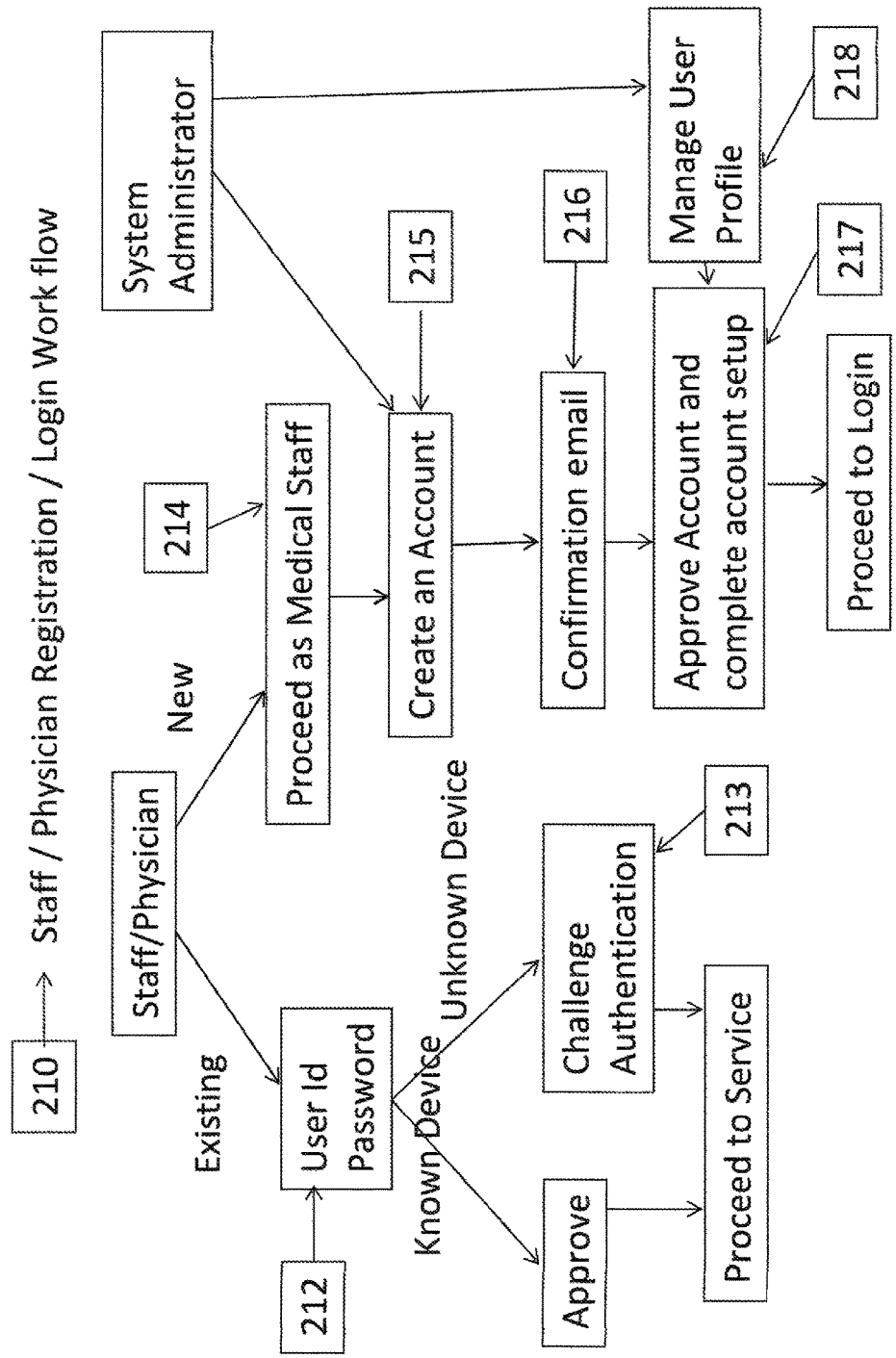
FIG. 6 is a workflow for creating a medical staff user or logging an existing staff in the system.

Similar to patient account setup and login, there is a process for creating accounts for other users such as healthcare service provider staff and for enabling access to the system. FIG. 6 shows the workflow (210) for creating a new account (215) and logging in the system (212) where the user is a medical facility staff or a physician or an administrator. This method is modified from one in FIG. 5 so as to identify the user as a healthcare provider staff member (214) and to assign various roles and to associate the user with the appropriate organization and departments (218) when completing an account setup process (217). These tasks can also be controlled where a healthcare facility manager or administrator may decide to manage creation of such accounts. Each staff user may have an assigned role and usage privileges which are further managed with creation of user profiles or user roles where each profile or role has attributes like what functions that role is allowed to perform. For example, a front desk person role user may be able to review and request completion of incomplete information authorized to be provided by the patients in today's work queue in a given form but may or may not be allowed to edit the information before a patient can be checked-in. Such user may print or export selected patient authorized data to other systems or forward the data to another user. On the other hand a nurse role user may only view patients that have checked in and have completed forms. Such user may not change any static patient data but may or may not update readings based on current measurements. Similarly a physician may chart readings for a given period of time for only those patients who have validated their recent token and so on. All security parameters discussed before including additional authentication (213) are applicable here. This could be further modified to match the security requirements of a specific healthcare organization. Use of single sign-on between existing systems of such an organization and the platform of the present invention is within the scope of such deployment. This embodiment of the invention supports use of cloud based servers as well as dedicated servers residing in healthcare facility data centers. This is supported as a deployment time configuration option that will be clear to people experienced in such technologies.

Patient Interactions

Figure 7:
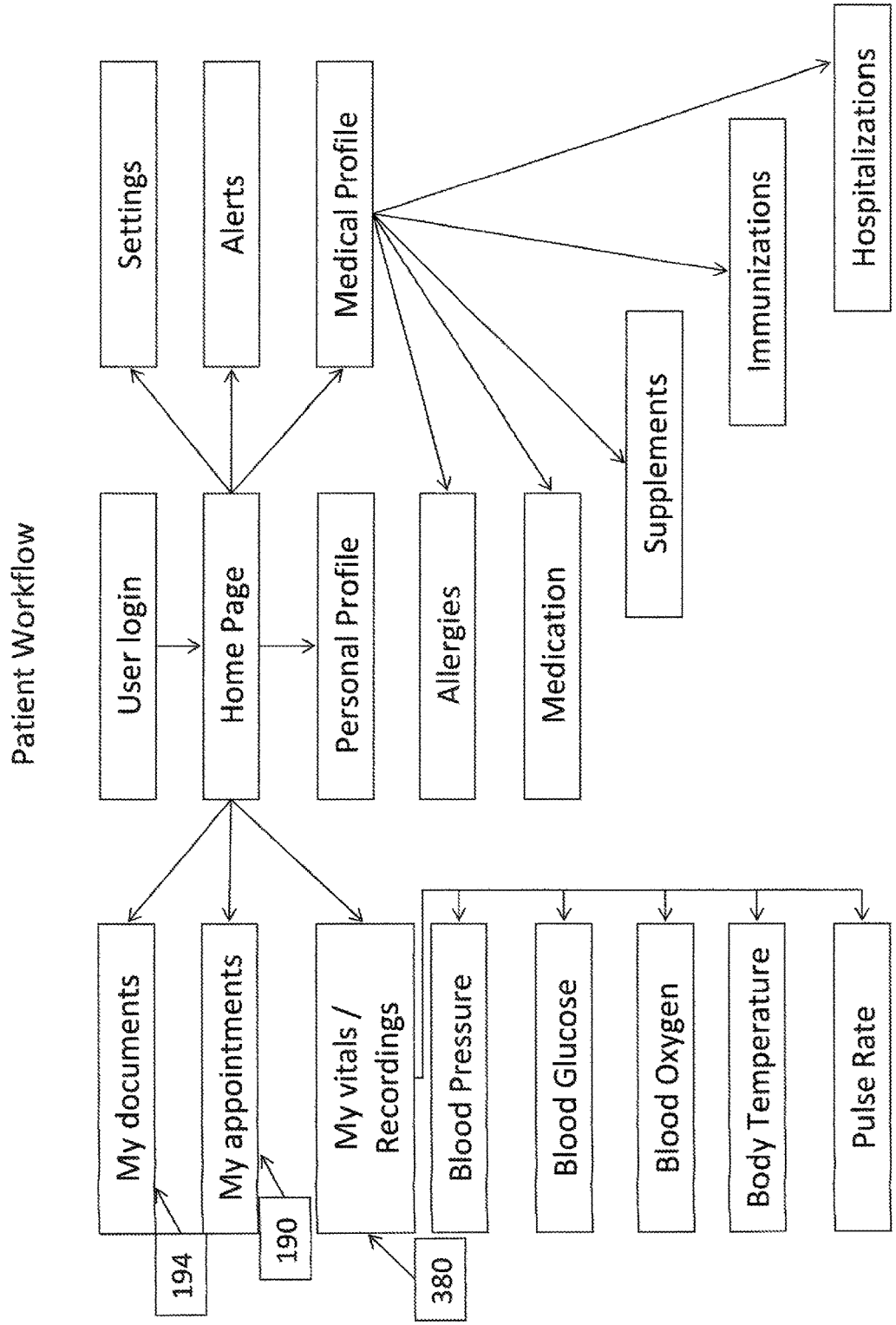
FIG. 7 is a high level workflow for a patient after they log in the system to enter data and take actions.
Figure 8:
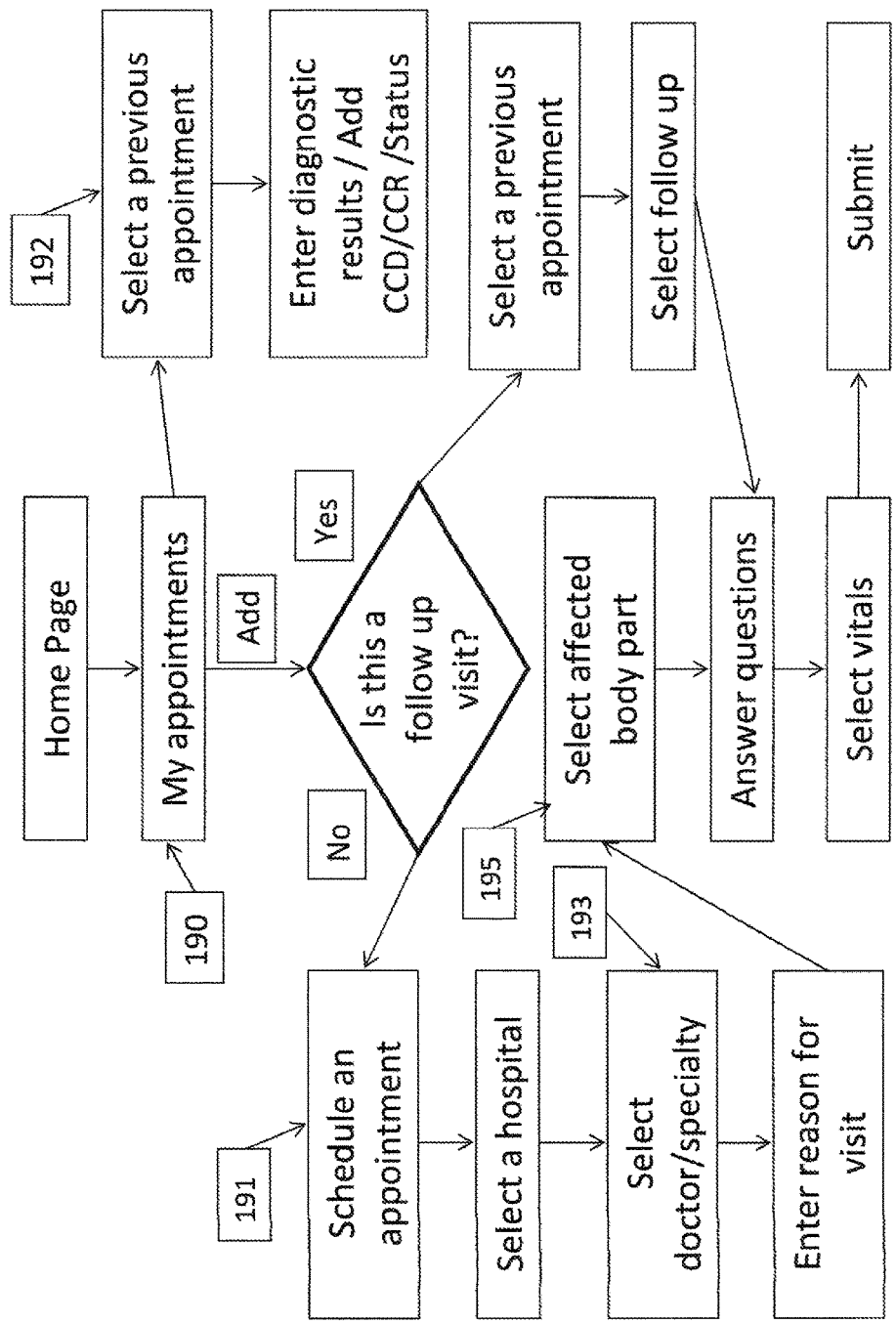
FIG. 8 is a high level workflow for a patient managing an appointment.
Figure 9:
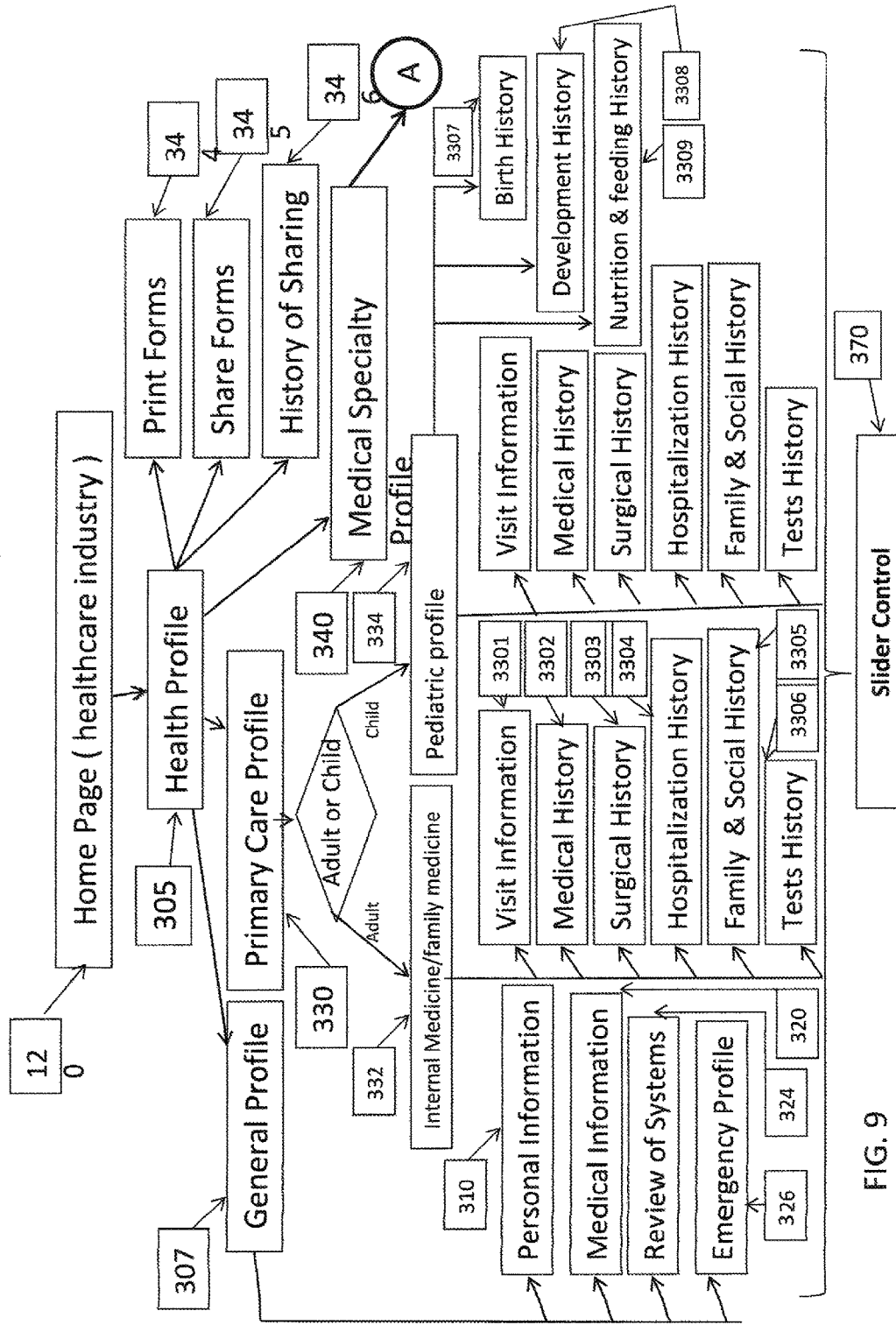
FIG. 9 is a workflow for patient to complete general health profile including slider control.
Figure 10:
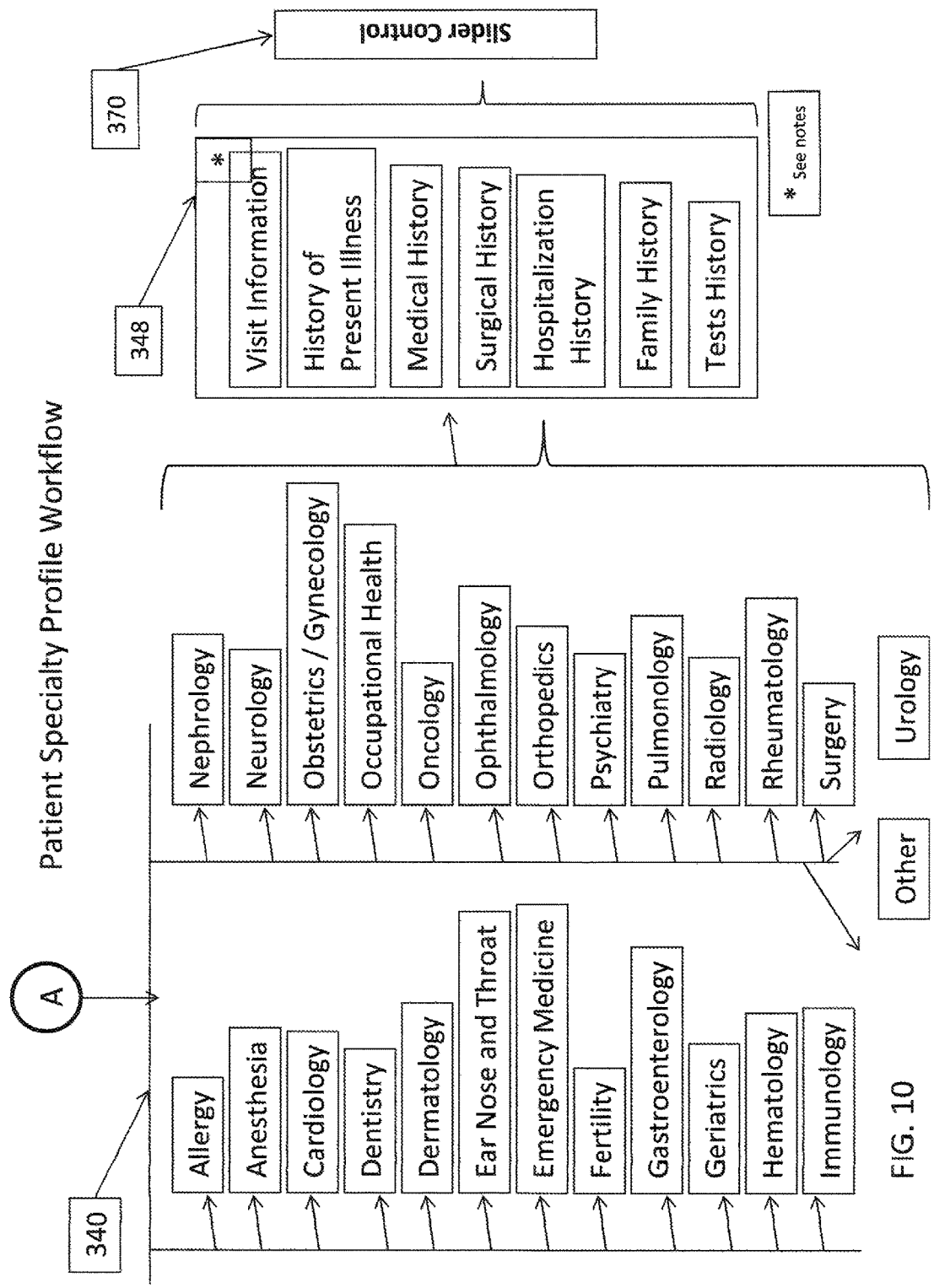
FIG. 10 is continuation of workflow from FIG. 9 to complete specialty health profile.
Figure 23:
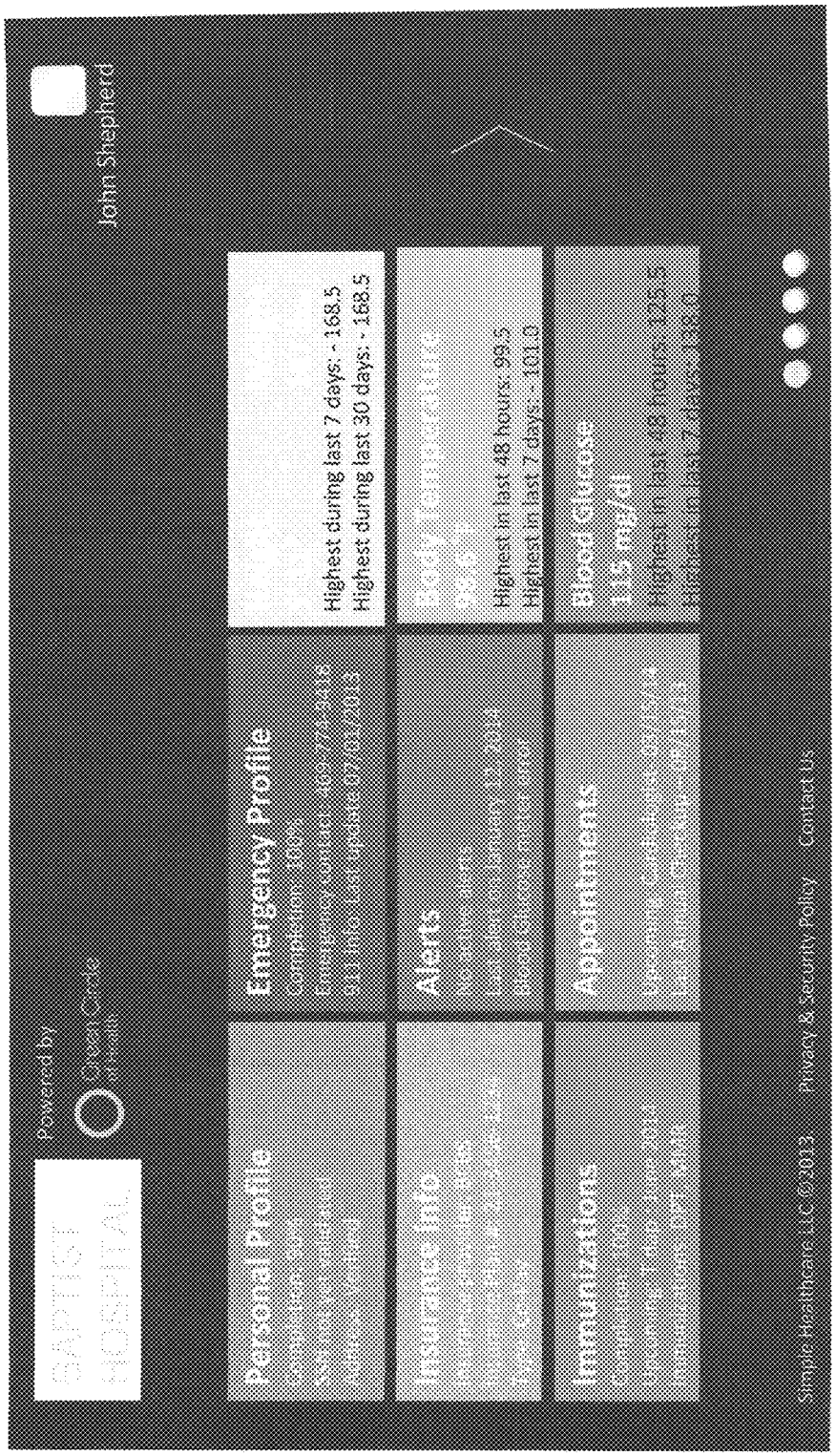
FIG. 23 shows user screen sample for patient home page with active tiles for various functions.
Figure 24:
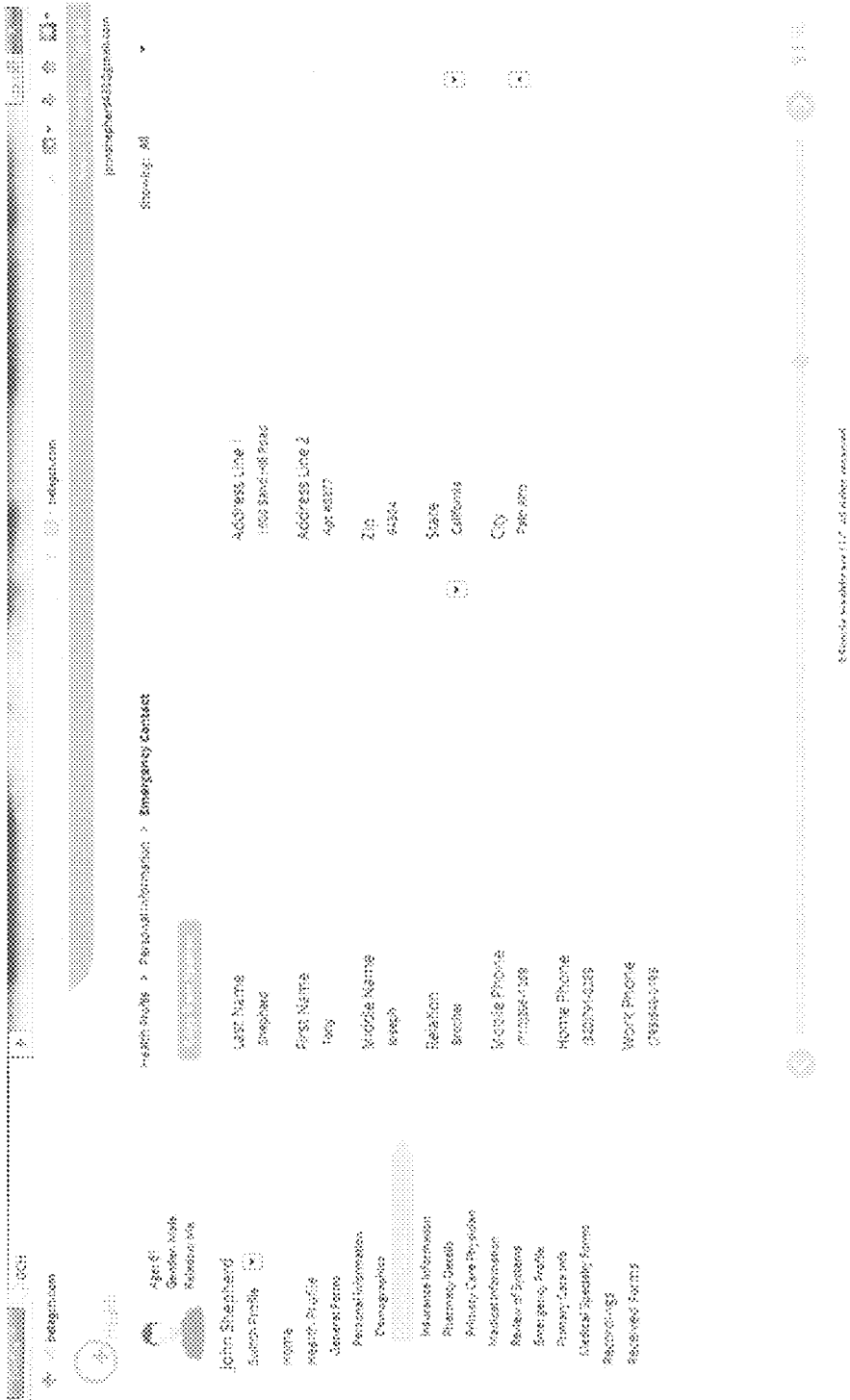
FIG. 24 shows user screen sample for patient to complete personal information in health profile.

Expanding on the user workflow, as a patient creates and manages her personal and medical data, FIG. 7, FIG. 7-A, FIG. 8, FIG. 9 and FIG. 10 illustrate the process of the present invention and outcome of such steps. The patient workflow begins each time an authorized user patient logs in to the system (110) and proceeds to home page (120) which in this case is a healthcare industry related home page. This page may contain a summary of the user activity (130), a link to adjust personal settings and use tools (140), links for health profile (305), vitals or recordings (380), a link for received forms from others (170) and alert/messages (180), and links to other functions. Each item may be presented as an active tile with information about latest updates or readings and so on. User screen sample in FIG. 23 shows an example of such active profile presentation. Upon selecting a respective link, additional features and functions are made visible to the authorized user by the platform. An authorized user that selects Health Profile, for example, is given a summary of profiles completed or partially completed such as General Profiles consisting of Personal Information (310), medical information including review of systems (320), primary care profiles (330) and specialty care profiles (340). As an example shown in FIG. 7 the platform includes items like medications, supplements, immunization history, hospitalization history, prior illness history and family and social history. Upon selecting a given profile, a series of questions are presented by the platform of the present invention for the patient to answer which in turn is a method to complete a profile without going into a form-fill approach. User screen sample in FIG. 24 shows such an interaction between the system and the authorized user to collect health insurance information. In addition to completing the profiles, as shown in FIG. 7-A, the patient is able to print forms (344), share forms (345) and view history of sharing of forms (346). Similarly, the patient can work on recording (350) of data or readings for physiological conditions such as Blood Glucose (351), Blood Pressure (352), Blood Oxygen (353), Pulse Rate (354), Body Temperature (355) and others. These vitals recordings could be received automatically from connected authenticated and authorized devices or data may be manually entered by the patient when automatic interface is not available. This allows the patient to accurately bring actual readings over an extended time to healthcare providers. While printing or sharing the forms, a patient can also include vitals recordings to print or share. This same home page also displays health or system alerts and messages for the patient. As shown in FIG. 8 the patient can also keep track of all the appointments (190) with healthcare providers where even without integration with the healthcare provider systems, such information is still useful to the patient and with integration it could be used to synchronize the hospital and patient calendars thus optimizing time for both parties. Further, the system of the present invention allows an authorized user to upload and store documents, images and charts or reports generated or gathered from other systems or scanned from papers (194) where such function may be centralized or distributed throughout the system for an authorized user to add documents without explicit attempt.

Next is the detailed description of some of the unique functions that the platform of the present invention supports that enable the patient to maintain control of such data and share selected data with authorized recipient healthcare staff.

Figure 21:
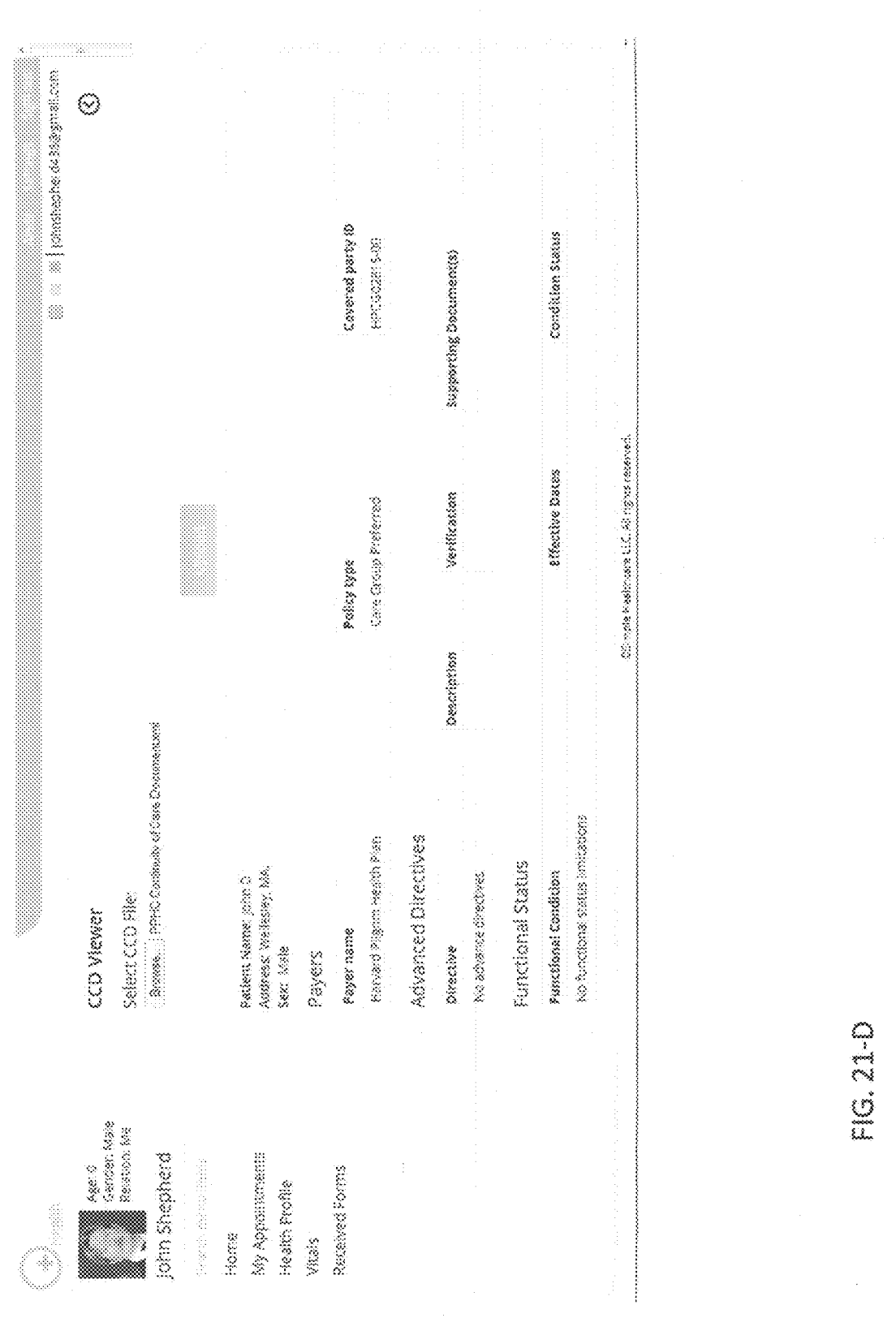

Expanding on the patient scheduling function, FIG. 8 shows additional details of the process of a patient scheduling an appointment (191) or updating information on an existing appointment (192). When the patient selects "my appointment", the patient can select if it is a new or existing appointment and if it is a new appointment if it is a follow-up visit or a new visit. FIG. 21-C shows a sample screen for such appointments. For scheduling a new appointment, the patient selects a hospital or healthcare service provider facility, a specialty or department (193) and a doctor to see and proceeds to provide the reason for the visit. The patient may select what part of the body is hurting (195) and the system may help the patient select a doctor or specialty or facility to visit and proceed to complete the rest of the profile information needed for that visit. The patient can further proceed to provide any vital recordings they have collected which may be useful for the visit. Once a visit is completed, the patient can select existing appointment (192) and mark the visit complete, and it will become part of the visit history with any comments added by the patient/user. If the provider electronic platform delivers results from visit via email or download through their portal, the patient can upload such information for storage in her data repository in the platform. In an integrated environment, an authorized recipient healthcare provider system may push such information as "Continuity of Care Data (CCD)" or "Continuity of Care Record (CCR)" to the patient by means of the present invention platform, where the system may parse and process the incoming data as well as present it to the patient in an easy to read format, making it less burdensome for the patient to maintain such information for future use. FIG. 21-D shows a sample screen for such CCD upload and viewer.

By way of continued explanation of the patient workflow to create and update personal and medical data, refer now to FIG. 9. This figure shows a workflow for a patient to work on her health profile (305) and get it completed for various uses such as sharing with an authorized recipient healthcare provider. After the patient logs in to the system; from the home page (120) as an authenticated authorized user she proceeds to Health Profile (305) where she reviews information and selects General Profiles (307). This gives her the status of various general data sets such as Personal Information (310), Medical Information (320), Review of Systems (324) and "Emergency Profile" (326). She proceeds to work on each of these areas using a "Slider Control" (370), provided according to one aspect of the present invention, to help in her navigation along with common browser controls.

As she works on each area, the present system helps her with progression updates and navigation. Next she selects Primary Care Profiles (330) and based on patient age, derived by the system from the birth date information collected as part of account setup and other personal information, the system presents her with an Adult—Internal Medicine/Family Medicine (332) or a Child—Pediatric medicine (334) profile to complete. Again, according to one important aspect of the present invention, completion of the profile is an interview process where various areas like upcoming visit information (3301), Medical History (3302), Surgical History (3303), Hospitalization History (3304), Family and Social History (3305) and Test History (3306) are collected with the help of a Slider Control (370). If it was a child profile, additional information like Birth History (3307), Developmental History (3308) and Nutrition and Feeding History (3309) will be collected. In all cases questions are adjusted by the present invention to be appropriate based on age and gender of the patient. Similarly Medical Specialty profiles (340) are collected as described in next workflow and sharing (345) as more fully described hereafter. An authorized user may also print, review, or check history of past sharing.

Figures 1, 26:
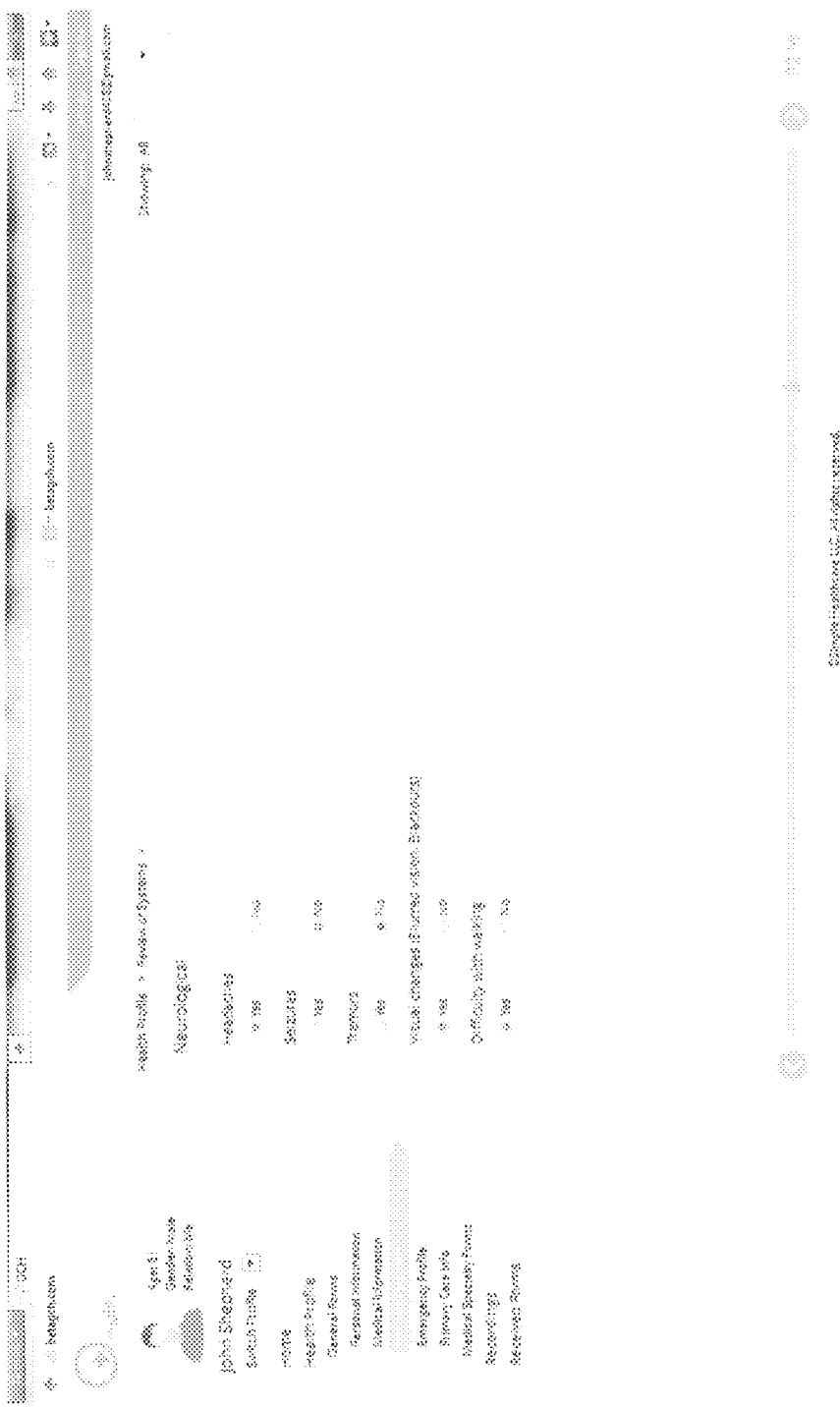
FIG. 26-A shows user screen sample for review of systems—Ear, Nose and Throat.

The following figures illustrate one implementation of these interactions on desktop or tablet platform with sample screen diagrams: FIG. 24,—sample emergency profile contact information, FIG. 25—A—sample of personal profile insurance information, FIG. 25-B—sample medical information for social and life style history, FIG. 25-C—sample medical information for allergies, FIG. 25-D—sample medical information for medications, FIG. 25-E—sample medical information for immunization, FIG. 25-F—sample primary care medical history, and FIG. 25-G—sample primary care test results and medical directive. FIG. 26 A—sample of review of systems for ear, nose and throat as one of twelve different systems shown in FIGS. 26 B to 26 L, These are examples of patient interviews presented to an authorized user to complete necessary data gathering to establish a complete record of patient history for future use. By means of one important aspect of the present invention, data normalization, the user enters data only once in the system and the system ensures that that data flows across all forms and all specialties so that the user does not have to re-enter the same information multiple times. This single data entry and persistence of data across all forms and all delivery makes the Applicants' platform unique and greatly valuable to a patient as well as to healthcare providers as not only complete data is available each time in all specialties but also data is highly accurate and readily accessible with clear indications of any changes. The platform of the present invention also supports audit trails for further analysis and investigation of changes if needed.

FIG. 10 shows a workflow that continues from the FIG. 9 to complete Medical Specialty Profiles (340). An authorized user patient is shown the status of the completion of the specialty profiles for each of twenty or more, for example only, the authorized user is guided to complete the remaining tasks to complete the profile. The platform can offer more specialties simply by adding them to this set. Each specialty interview supports unique requirements of medical data for that specialty. A patient begins by selecting a specialty and begins to complete necessary information for an upcoming visit with a healthcare provider. Once a specialty is selected, the slider control (9370) helps the patient navigate through the question and answer session. For each specialty, the patient provides data (348) consisting of Visit Information. History of Prior Illness, Medical History, Surgical History, Hospitalization History, Family History and Test History, etc. Here the questions are tailored for the specialty selected and by means of the data normalization process of the present invention any common data used in General Profiles and/or any other specialty is also updated and made available across all profiles, removing duplication of data entry. FIG. 27-A to FIG. 27-D shows sample screens for some of the data entry screens for Cardiology specialty. A patient only answers cardiology specific information when gathering data for this specialty and the same logic applies to all other specialties supported by the platform.

Figure 11:
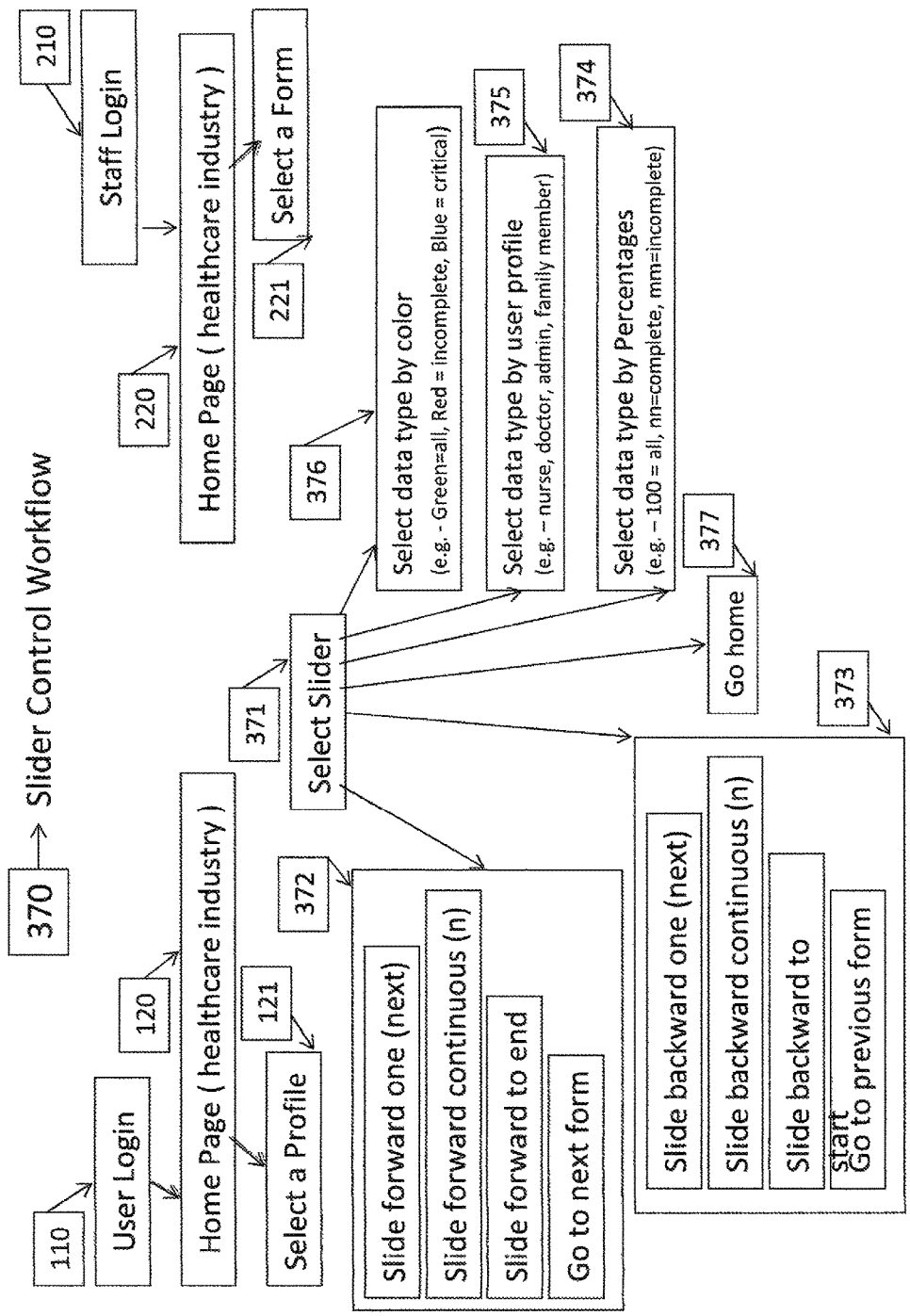
FIG. 11 shows functionality of slider control.

Another unique aspect of this platform is the ease of data entry made possible for the patient by means of various control features of the present invention as, for example, the slider control. FIG. 11 describes the slider control (370) which makes it easy for an authorized user patient to progress through data entry. A patient selects a profile to work on (121), which results in the invention automatically bringing up the slider control. The slider control allows the patient to go forward (372) where she can go to next question or next page, jump to any other questions or pages forward in the sequence, or go to the last question or page or go to next data set or form. Similarly, the patient can go backward (373) to a previous question or page, jump to any preceding questions or pages, or first question or page or go to a previous form or data set. The patient can select a type of data set using colors (376) or a drop-down list—for example, green equals completed items, red equals incomplete items, or blue equals critical items, or yellow equals all items and so on. The present system may allow control of what is available for display or edit by setting various user profiles (375) where a different data set is associated with a different user profile. One can also manage the data set by status of data set such as percentage complete or incomplete (374). One implementation of such slider control is visible in a number of screen design samples included here like FIG. 25. Similar to the patient, the authorized recipient medical staff may also use the slider control to improve use of data and interaction with the patient where the staff can use the slider control to identify what data is completed for a given patient visit, what is incomplete and to present incomplete information to the patient and request the patient complete and resubmit the data form. This eliminates the need for going through an entire data set or set of forms to find out if an item of interest is complete or not, or what are the parameter values in critical areas and so on.

Figure 12:
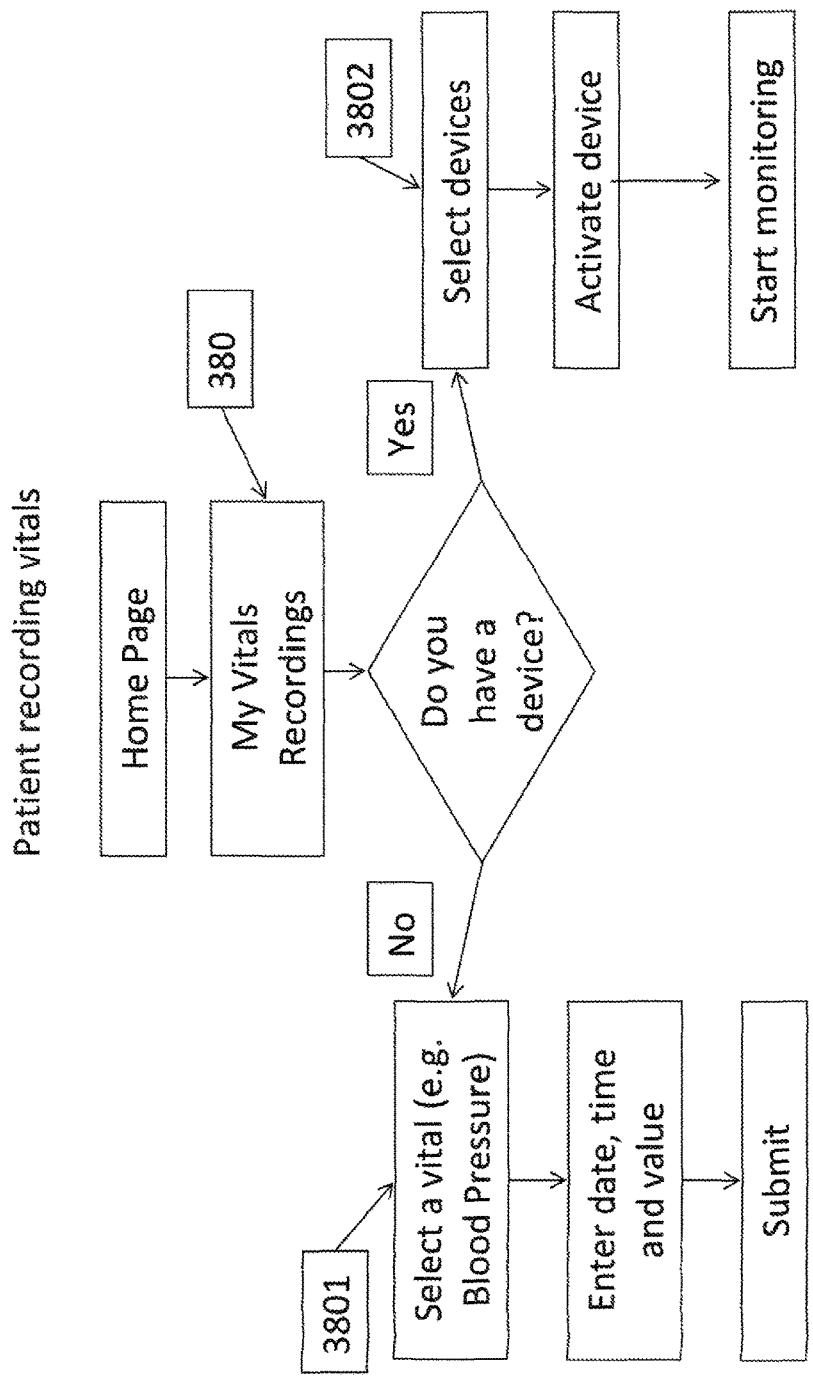
FIG. 12 shows patient recording of vitals manually or with a device.
Figure 28:
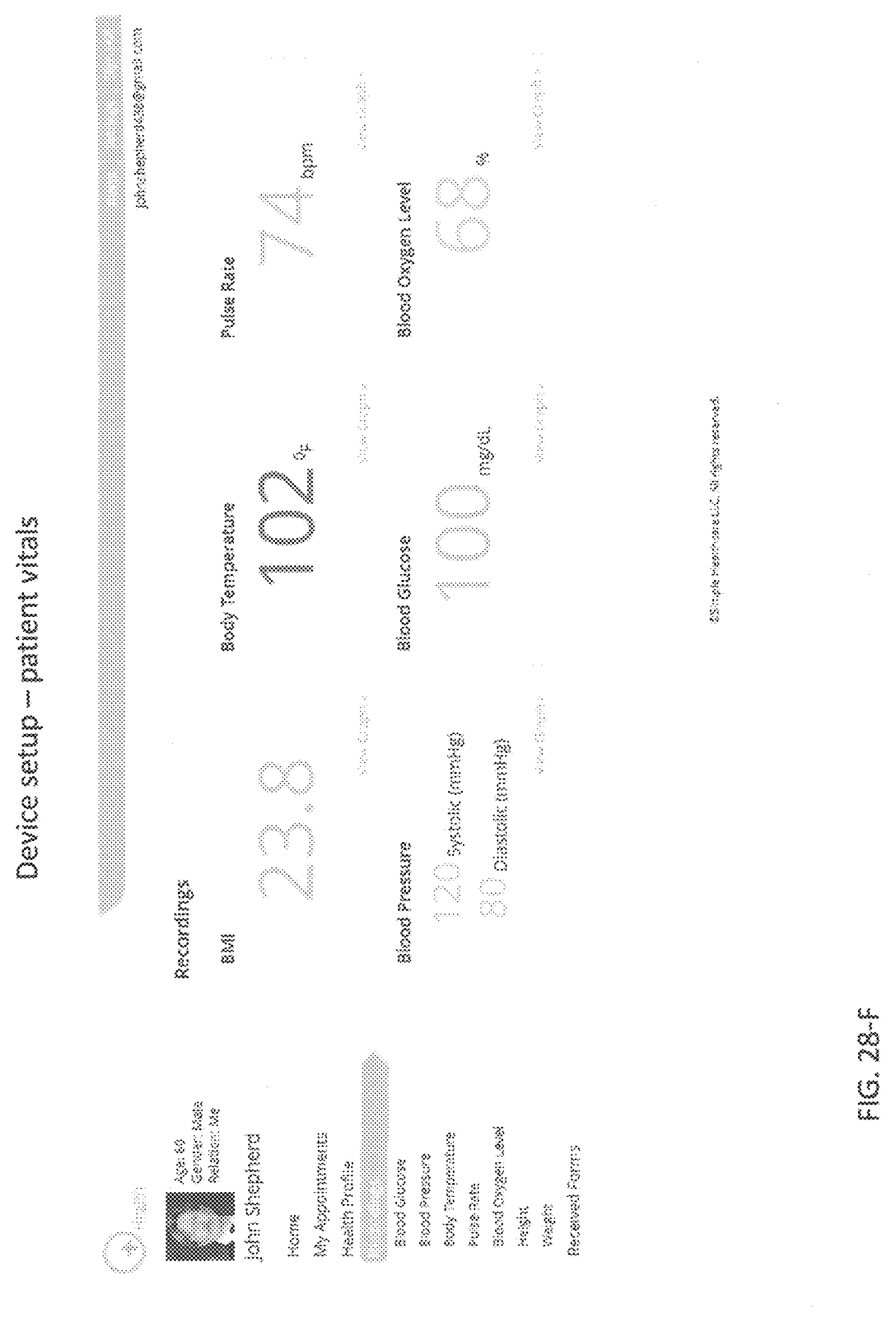
Figure 29:
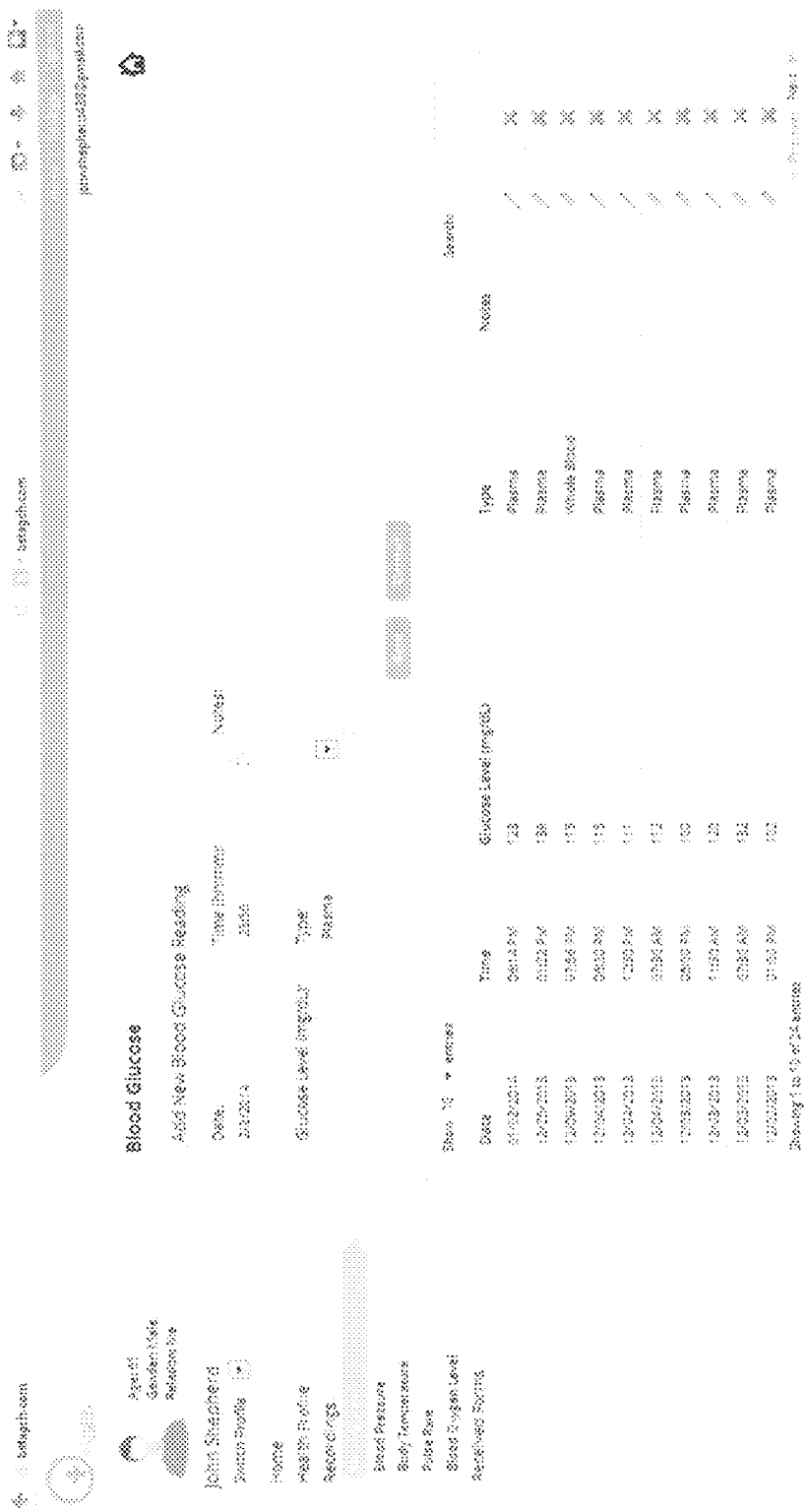
FIG. 29 shows user screen sample for blood glucose recording.
Figure 30:
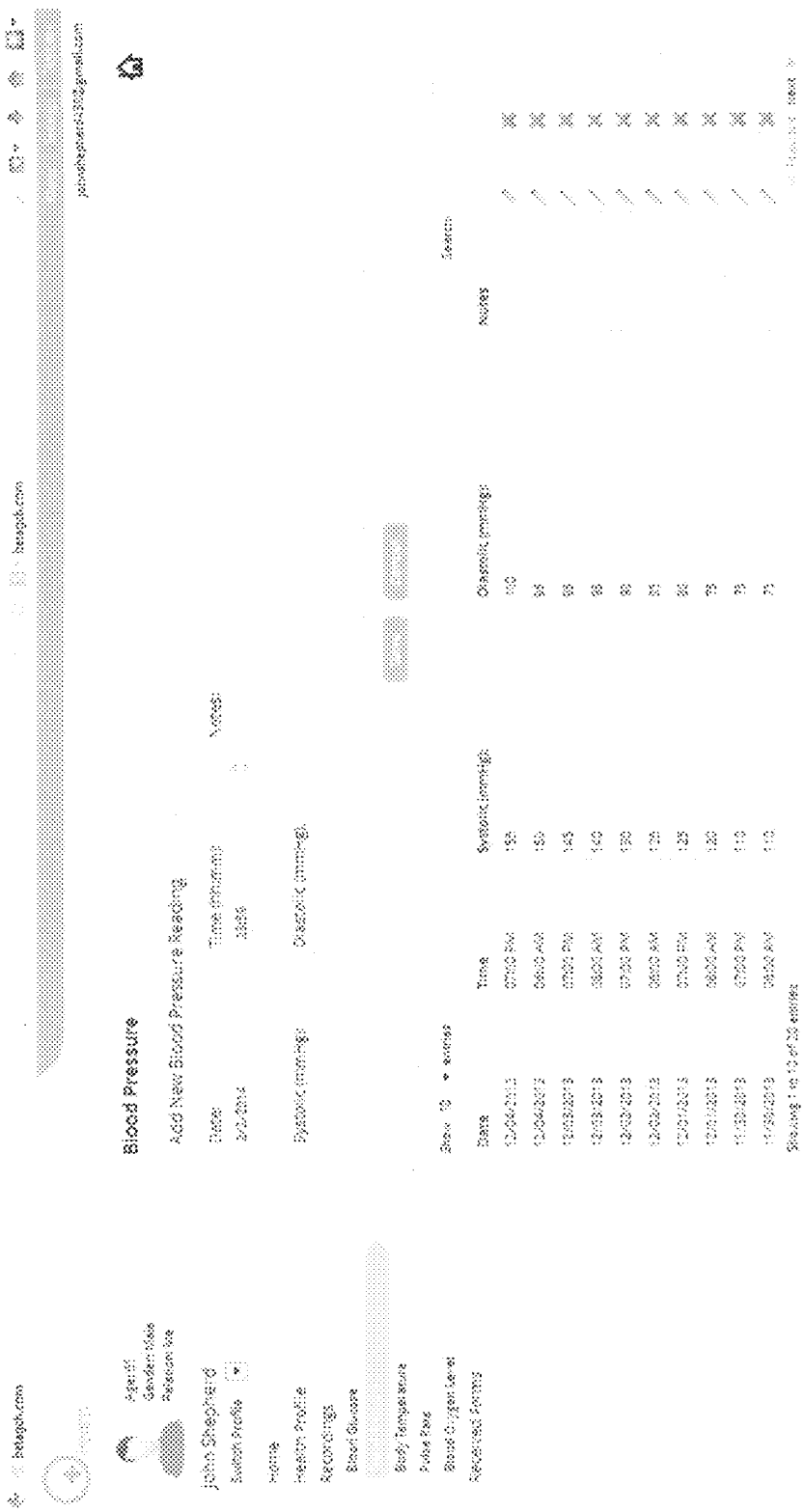
FIG. 30 shows user screen sample for blood pressure recording.
Figure 31:
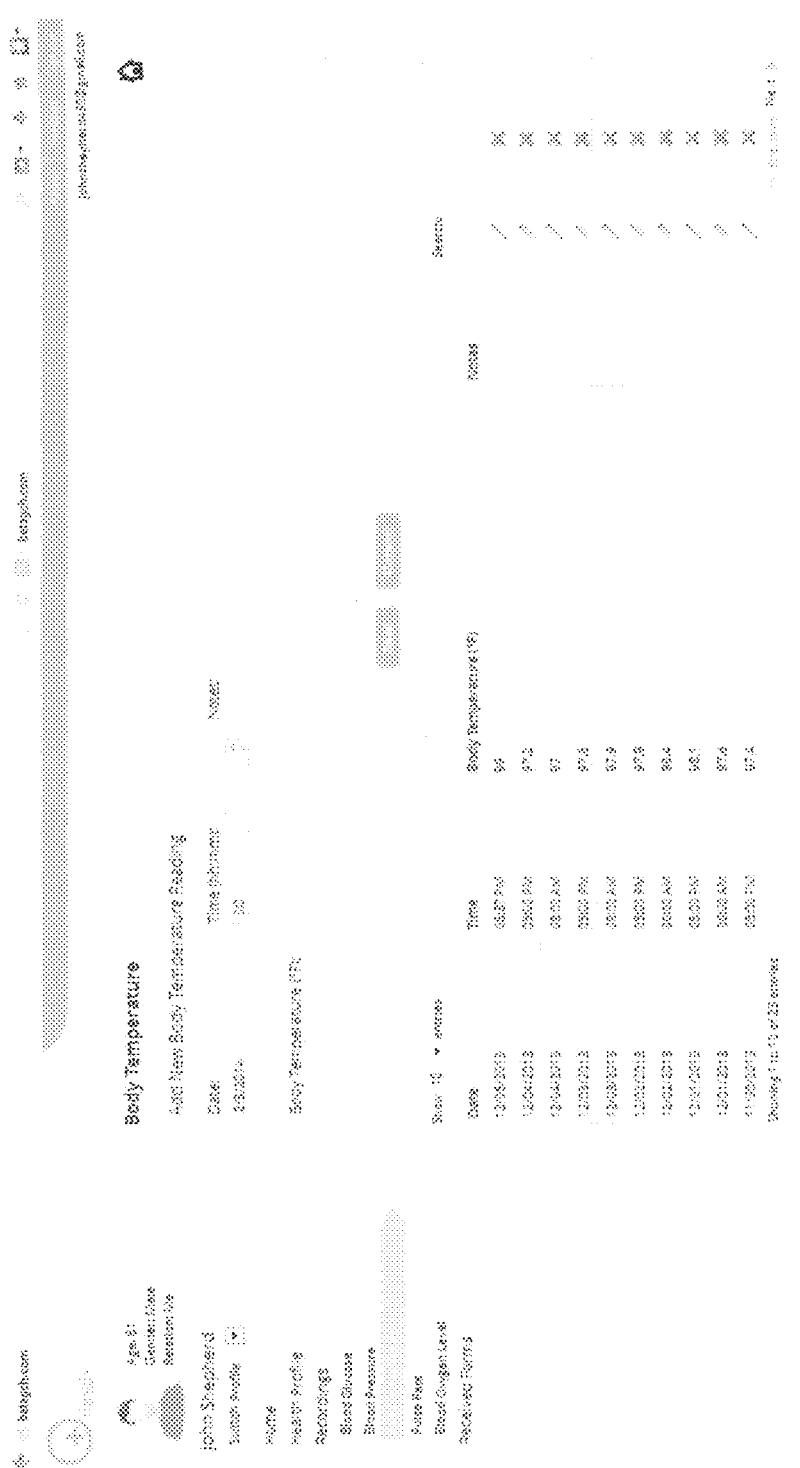
FIG. 31 shows user screen sample for body temperature recording.

So far the description has focused on the relatively static part of a patient's medical history that does not change frequently. An authorized user updates such data through an interview process and slider control as described above. However, with medical services, there are certain data elements that are considered vital signs of a patient which change frequently and could be useful to record and monitor for diagnostic and treatment reasons. To enable such recording of vital data for various physiological conditions, FIG. 12 shows how the present invention enables a patient to record such vitals. From the home page, the authorized patient selects My Vitals or Recordings (350). Here the patient has a choice to make: manual entry of various physiological data (351) or use of a monitoring device (352) to observe and record data automatically in the platform. When using a device to record the data, the workflow begins with registration and activation of such device. FIG. 12-A shows an authorized user registering devices (3591), setting up device parameters and activating devices (3592) or deactivating such devices. There are multiple scenarios where either the patient is using her own device or a healthcare provider supplies such a device preconfigured with a specific device profile to set recording parameters. In this later case, a device is configured to record specific types of data for a specific patient or multiple patients may use the same device in a group setting. It is also possible that multiple devices that record multiple parameters for the same or different patient can be registered with a network hub using a device to network with a hub connection, where for each device there is device detection, identification and registration and a connection is established (3594). Here an authorized user network hub is registered with the platform (3595) and such hub is activated to communicate with the platform (3596). In such setup, the device records a patient's data and uploads that data to the platform directly or via the network hub (3593). The platform requires proper identification to ensure that data recorded via a device is associated with appropriate authorized user patient. The platform also takes care of time stamping of each event. The data of interest, for example only, could be blood glucose level (381), blood pressure (382), blood oxygen level (383), pulse rate (384), body temperature (385) and any other measurements that may be required to be monitored for a given patient. Such data could be entered in the platform via manual entry in the system or automatically via an authorized authenticated device reporting the data. The platform allows the patient to print, or view the data in a table or a graph (357) format, share the data with others (356) and review history of sharing (346). The platform also allows the patient or healthcare provider to set up limits, goals, rules, filters and triggers (386) for each patient for each data stream and monitor them to see if a given reading is within a normal bend of values or how it compares to a set goal or how it matches alert criteria and to generate an alert or message (180) using an alert engine (387) and/or messaging service (388) when triggers are reached. There could be, for example, an alert sent because of a missed event such as a missed recording of data or taking of medication. The alerts engine may also handle escalation or distribution of different types of alerts to different people or destinations. Coordination, management and distribution of alerts at the central monitoring facility of an authorized recipient for such patient generated real time or near real-time data opens up a new frontier in medical care at home as well as for hospital facilities that no longer have to wait for periodic visits by the staff to a patient to take readings and to trigger manual intervention. FIG. 28-A to FIG. 28-F show sample user interaction screens for device setup that includes device manufacturer setup, adding a device, creating a monitoring profile, assigning a device to a patient with specific monitoring profile, a healthcare provider receiving alerts from a set of patients under observation and a patient view of vitals from manual or recording devices. FIG. 29 shows patient recordings for blood glucose levels, FIG. 30 shows patient recordings for blood pressure and FIG. 31 shows patient recordings for body temperature. Other recordings can be done in similar fashion for patient height, weight, BMI, pulse count, urine output, and oxygen level and so on. These data may be entered manually or using an integrated device that may be setup by the patient or a physician as shown earlier in FIG. 28-A to FIG. 28-D. These recordings may be linked to an alert engine where, based on alert criteria selected by an authorized user, they will generate various alerts as described earlier.

Figure 13:
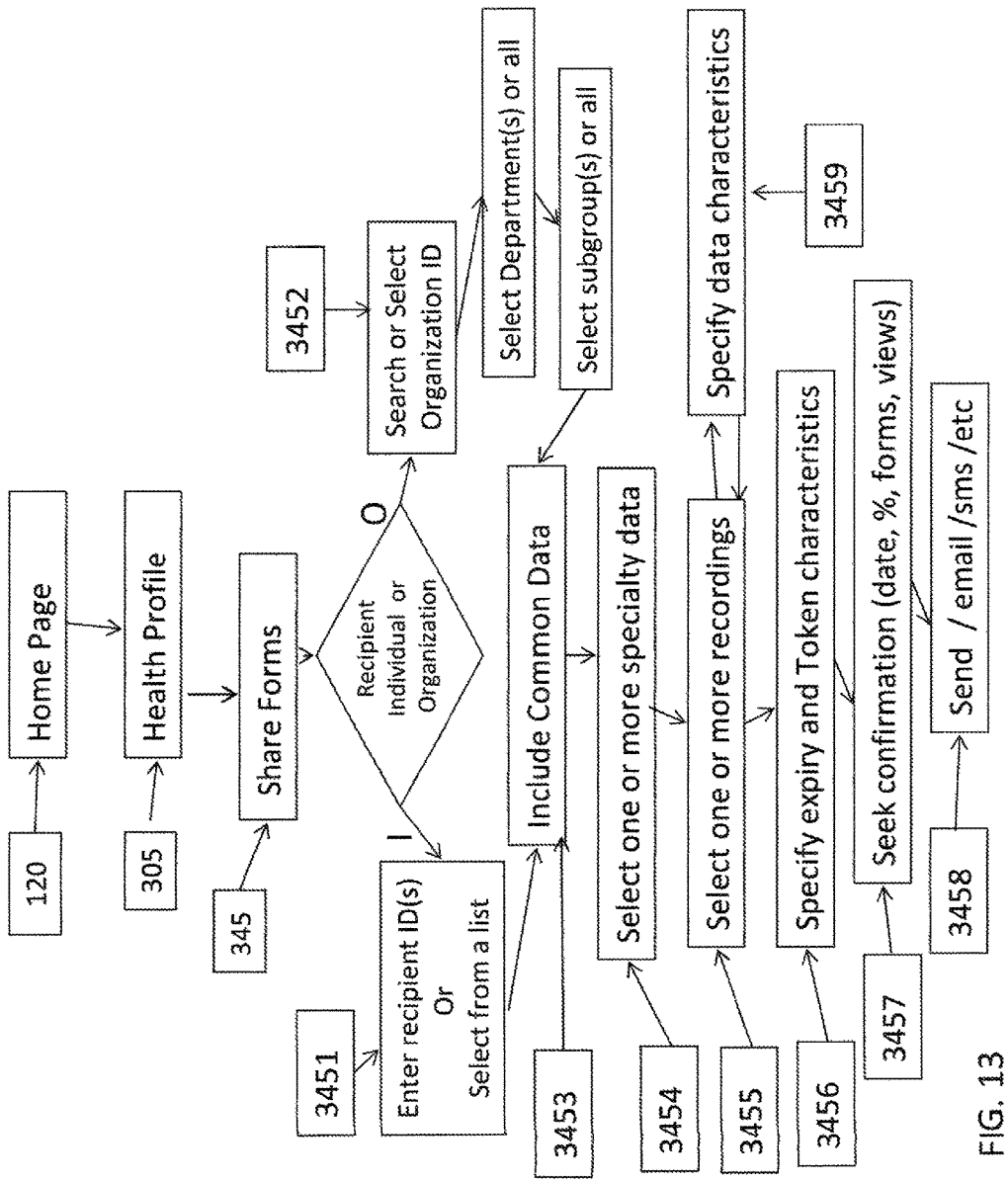
FIG. 13 shows sharing of forms with individuals or organization.

One important aspect of the present invention is the change in workflow such that the patient owns and controls creation and delivery of medical data to healthcare provider. Here follows a description of one such implementation of how an authorized user patient selects the information that is entered or collected by a patient as explained above and then decides to share selected data with one or more authorized recipient people or organizations. FIG. 13 shows a patient sharing data forms with an authorized recipient service provider organization (3452) or an authorized recipient individual (3451). From the health profile, the authorized user patient selects to share selected information (345). Upon selecting to share the data with an individual, the user selects a recipient from a list of past recipients, for example, that is organized in chronological order, typically the last used address appearing at the top of the list. The user may enter the id or email address of the person receiving the information. The user can select more than one individual at the same time to send same information. Upon selecting an authorized recipient organization, the authorized user may search for a participating organization, and once an organization is selected, the authorized user may further select a department or group, sub group or individual within that organization. The authorized user may select multiple organizations to receive the same information.

Once the authorized user has selected one or more authorized recipients, the user selects or by default includes common data such as personal profile, or primary care profile, to share with an authorized recipient (3453), the user further selects one or more specialty forms data to include (3454), for example, and the user may select any recorded vitals (3455) and if so desired specify characteristics of such data to be shared (3459). The user specifies if a token will be used and so will it be used each time the shared data is accessed or just once (3456) when the first time such data is accessed by an authorized recipient. The user is prompted if the data being shared is incomplete and if the user wishes to complete it or make any changes before sharing; what is the date when the data was last updated; and if the user wishes to view how the authorized recipient will see the data being shared (3457). The user may be asked to sign the form being shared using a touch pad or other device as shown in a sample screen in FIG. 35. The user confirms all the information and shares the selected information with the authorized recipient. The authorized recipient may be notified of a user sharing selected data via email, SMS messaging or with an alert within this service platform (3458).

Figure 14:
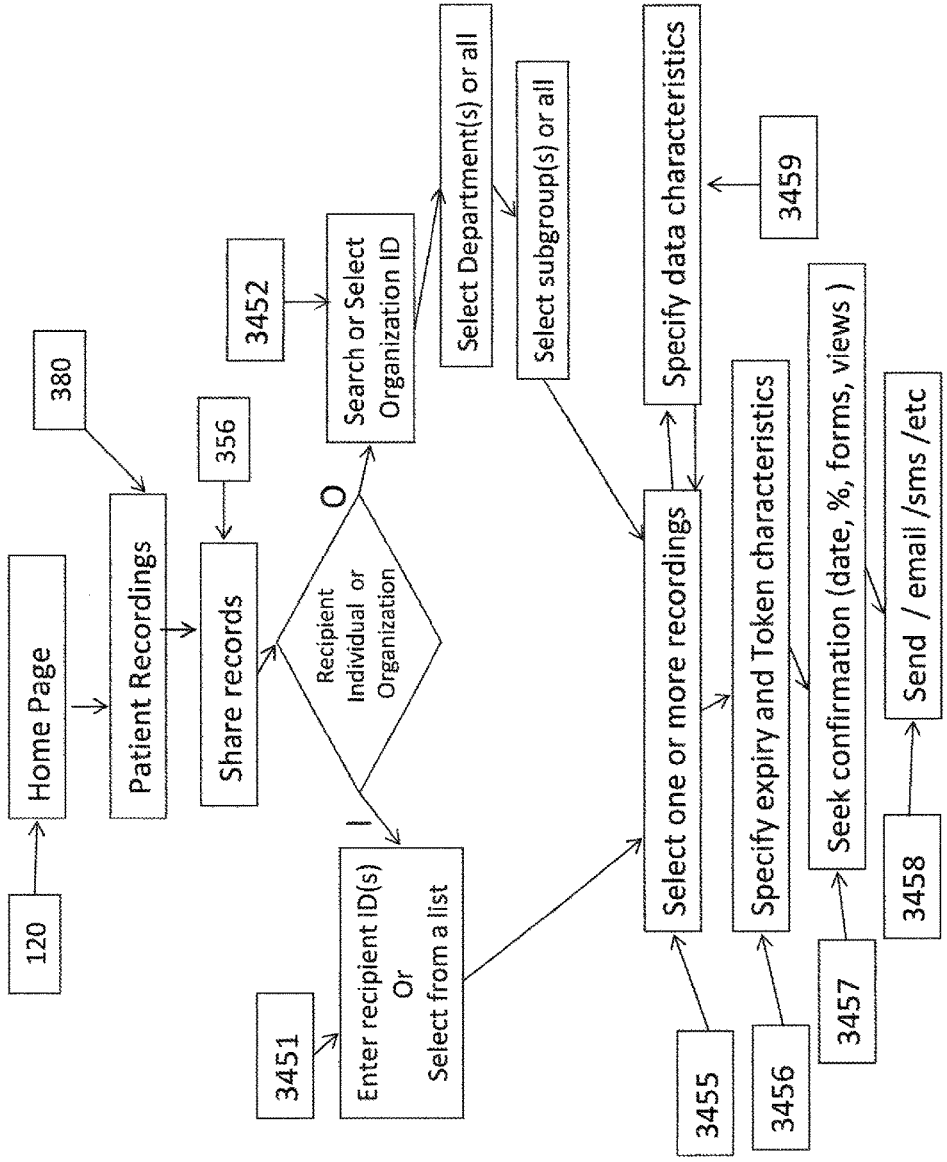
FIG. 14 shows sharing of recorded vitals with individuals or organization.
Figure 32:
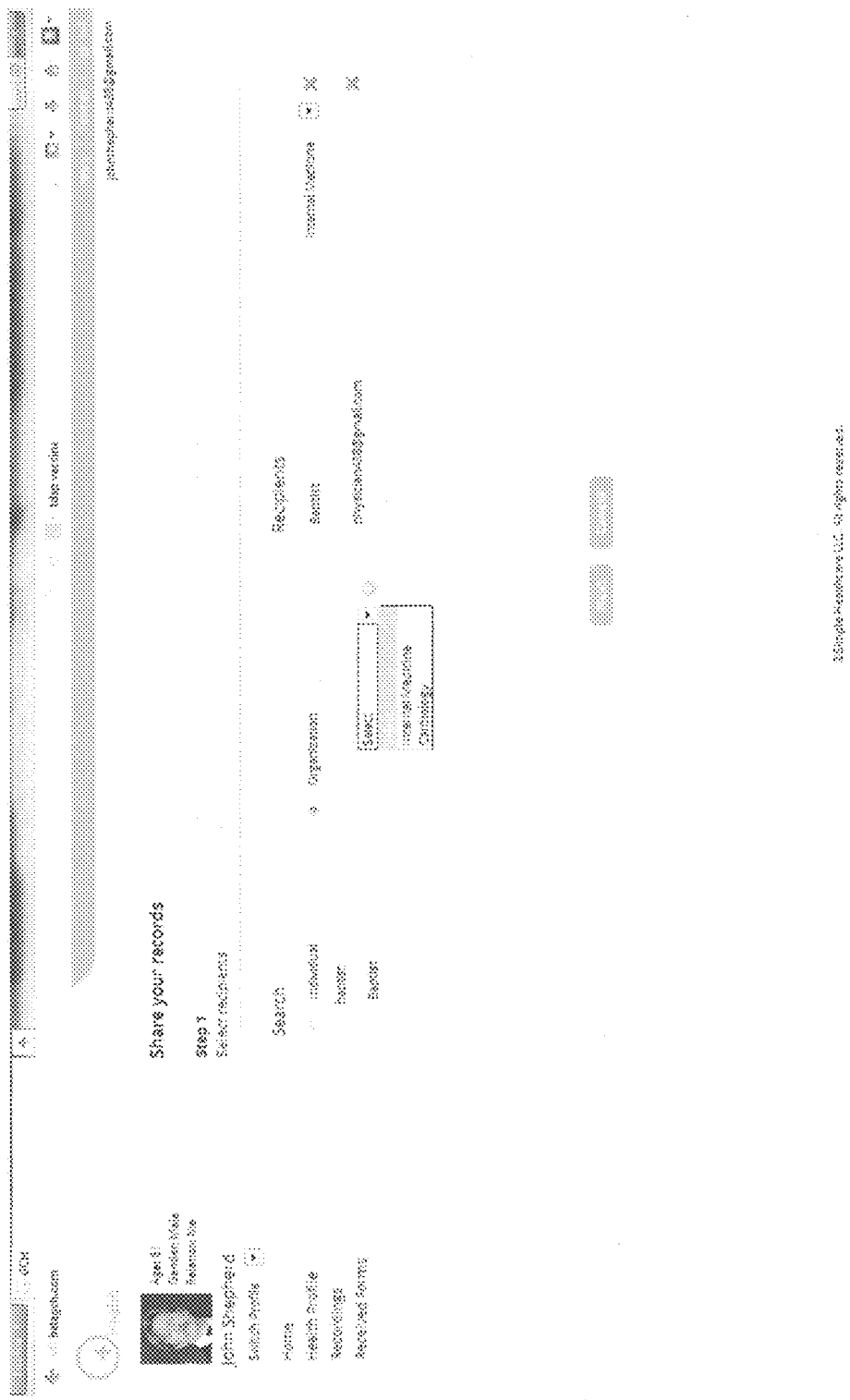
FIG. 32 shows user screen sample for sharing a patient record with an organization.
Figure 33:
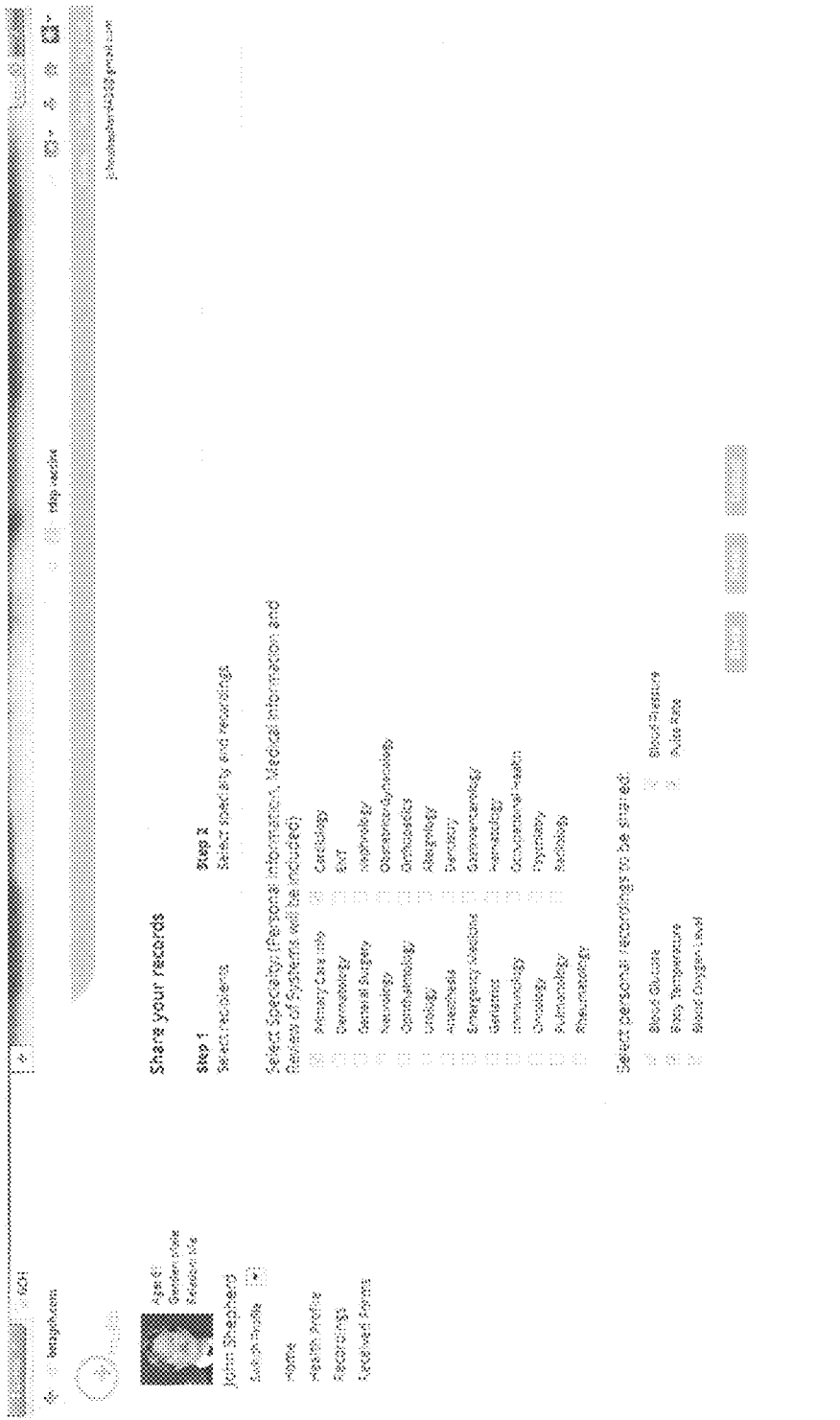
FIG. 33 shows user screen sample for selecting records and vitals to share.
Figure 34:
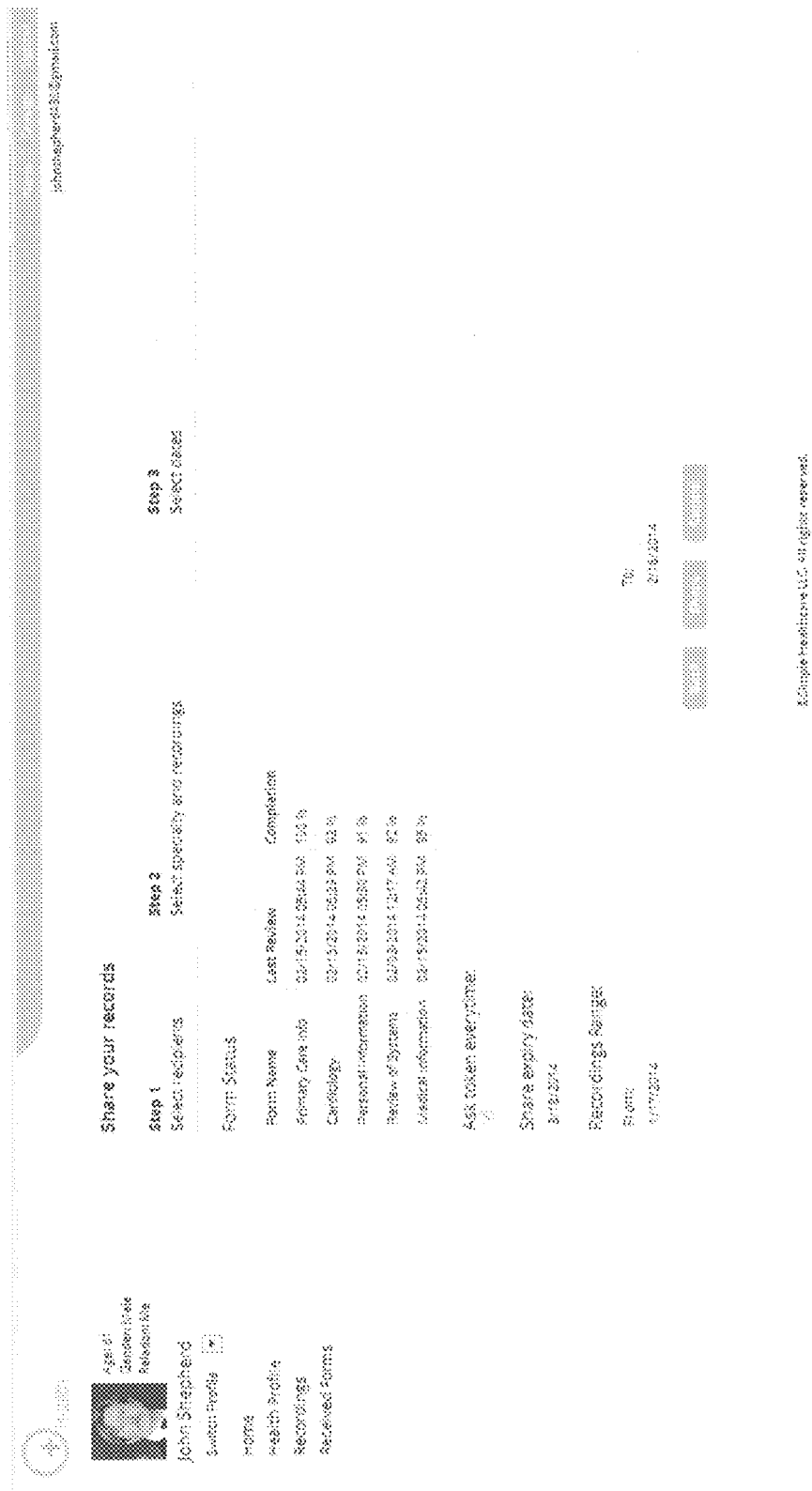
FIG. 34 shows user screen sample for confirming what is being shared and how.
Figure 36:
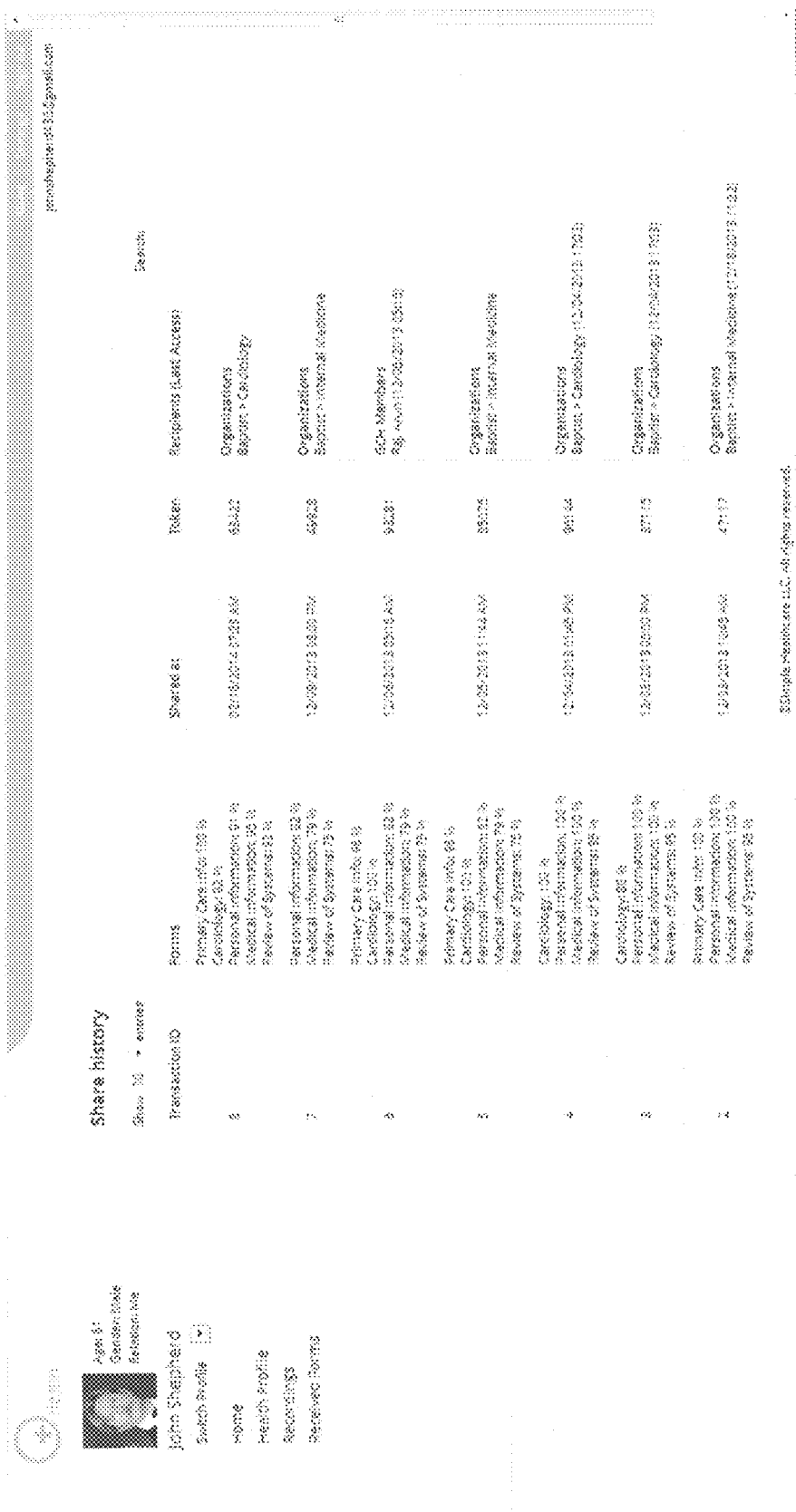
FIG. 36 shows user screen sample of sharing history report.

Just as sharing of personal and medical history is defined above, the system process for sharing of patient vitals or recorded data is shown in FIG. 14. From the home page, an authorized user patient selects recordings (380) and sharing of recordings (356). The user selects if she is sharing data with an individual (3451) or an organization (3452). The user further selects what recordings are to be selected (3455) and specifies data characteristics (3459) such as date range, data values, triggers for sharing data, frequency of recording and sharing of data, and so on. (3459). If a token will be used for sharing of records, token characteristics are defined (3456) and the user confirms the information (345) and shares the selected data (3458) with authorized recipients. It is possible either that data is shared only once or data may be updated by the patient or automatically by a device and recorded in the present platform and, with ongoing sharing, the authorized recipient gets the updated data as it happens. As explained before, alerts are provided to be generated based on trigger conditions on recorded data as is one aspect of this service platform of the present invention. FIG. 32 shows a patient sharing selected data by selecting individuals and/or organizations to be designated as authorized recipients, FIG. 33 shows a patient selecting what data forms and recordings to share, FIG. 34 shows a patient reviewing the status of all the data and adding a token, date range and other sharing parameters, and FIG. 35 shows signature page and confirmation of the action of delivery of user selected data with authorized recipients and FIG. 36 shows the history of sharing by the patient.

Healthcare Service Provider Interactions

Following next is a description of the workflows for authorized recipient healthcare service providers. This workflow does not replace the service provider's existing EHR or PMS or HMS platform driven workflow but augments that process with more accurate and at times near real-time data coming from the patient. Where the provider prefers to use its existing platform exclusively, a simple export or loading of data from the Applicants' platform brings more accurate information to the service provider's existing workflow. As explained before in user registration, there are various user types or profiles for authorized recipient healthcare workers which will determine what types of activities and actions such a user may perform while using the system of the present invention and what they may do with the patient data such as reading, editing, routing, monitoring, etc.

Figure 15:
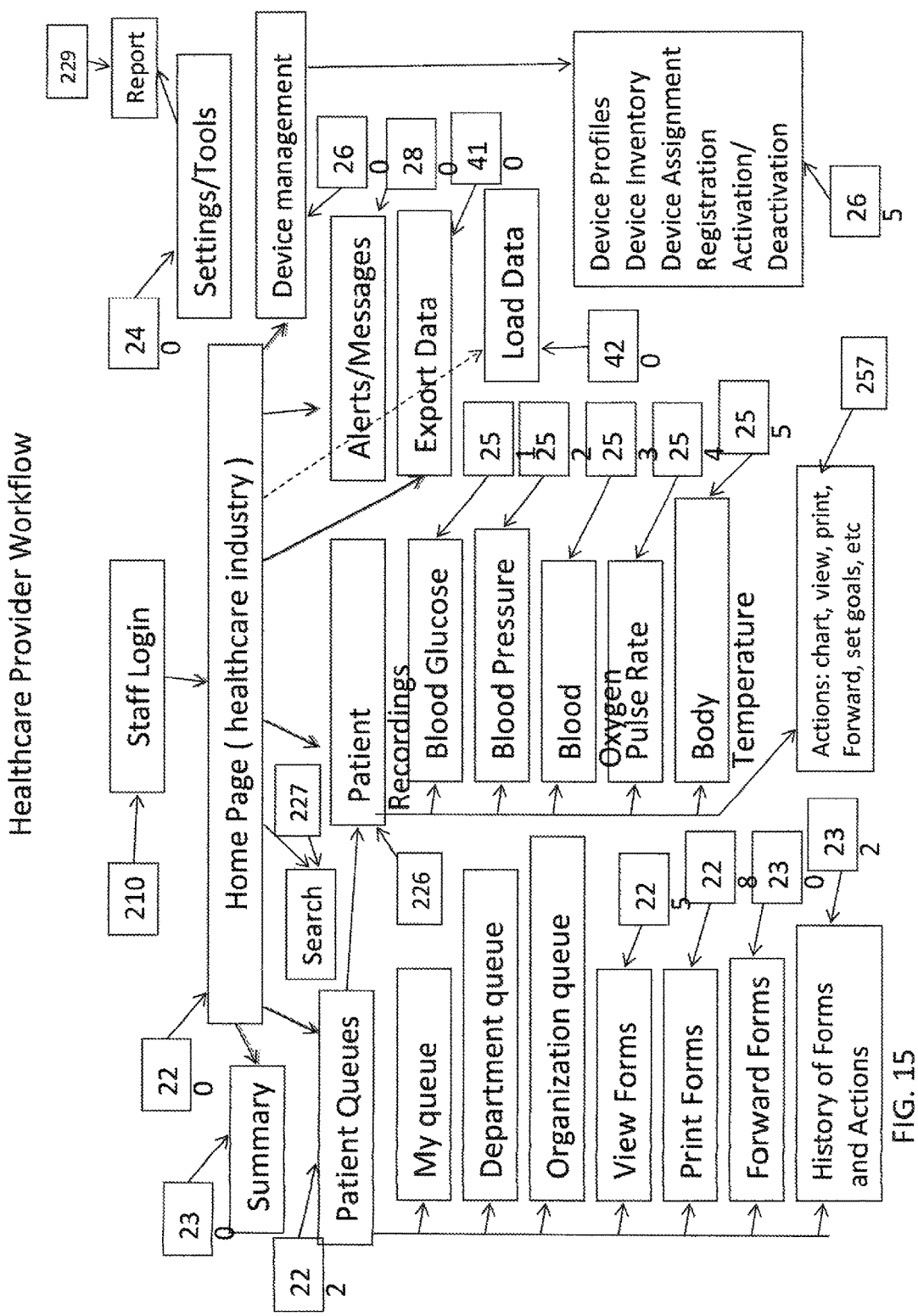
FIG. 15 shows a high level workflow for a healthcare provider to perform various functions.

FIG. 15 shows a workflow for a high level healthcare provider where an authorized recipient healthcare provider logs in to the system (210) and proceeds to home page (220). This home page is configured based on user profile and may contain information such as summary of the user activities (230), a link to adjust personal settings and use tools (240), a list or content of one or more patient queues (222), list or content of one or more patient recordings (226), and a dash board with monitored patients and related alerts and messages (280) is displayed. Once authorized to access the system of the present invention, a staff person can export the data (410) to one or more healthcare systems used by the facility or can load the data (420) manually into those systems.

This method offers full functionality of alert management so as to analyze data coming from many patients and to route alerts according to various criteria such as severity, values, time of day and so on. It allows the service provider user to acknowledge an alert and perform follow-up functions or route a message. Each item in the home page or dashboard may be presented as an active tile with information about latest updates or readings or queues or arranged per user preference and so on. Upon selecting a respective item or a link, additional features and functions are made visible by the present invention to the user. Also based on the particular role of healthcare provider, different sets of data or links are made available on the home page. So for example, a front desk person may see a queue of all patients who are checking in, while a nurse station may see a queue of only patients who have checked in and are coming to that particular department. When this user selects a patient queue, the user sees a patient waiting in her queue or her department and so on. She can also search (227) for a patient using various search criteria or run one of pre-set or custom reports (229). She can select a patient, redeem a token, and view (225) or print (228) or forward (230) a data set or form to someone else. She can see a history of forms, records and actions (232). Similarly healthcare providers can work on recordings (226) of data or readings for physiological conditions such as Blood Glucose (251), Blood Pressure (252), Blood Oxygen (253), Pulse Rate (254), Body Temperature (255) and others. Healthcare staff can take various actions (257) such as view, print, forward, chart by various criteria or set limits or goals for the patients or compare current data against history and so on. Based on their role, the authorized recipient healthcare provider may also manage various devices used to monitor patient vitals. This device management service (260) consists of establishing device data monitoring profiles (265) for various readings such as to trigger alerts when temperature goes above or below certain limits, or a device fails to report within certain time and so on. Device management includes all the functions as defined in self-service mode by the patient in FIG. 12-A blocks 3591 to 3596. It also includes device inventory management, assignment of a profile to a device or a measurement, setting up monitoring of a patient and monitoring of devices across a pool of patients for a practice or group.

Figure 16:
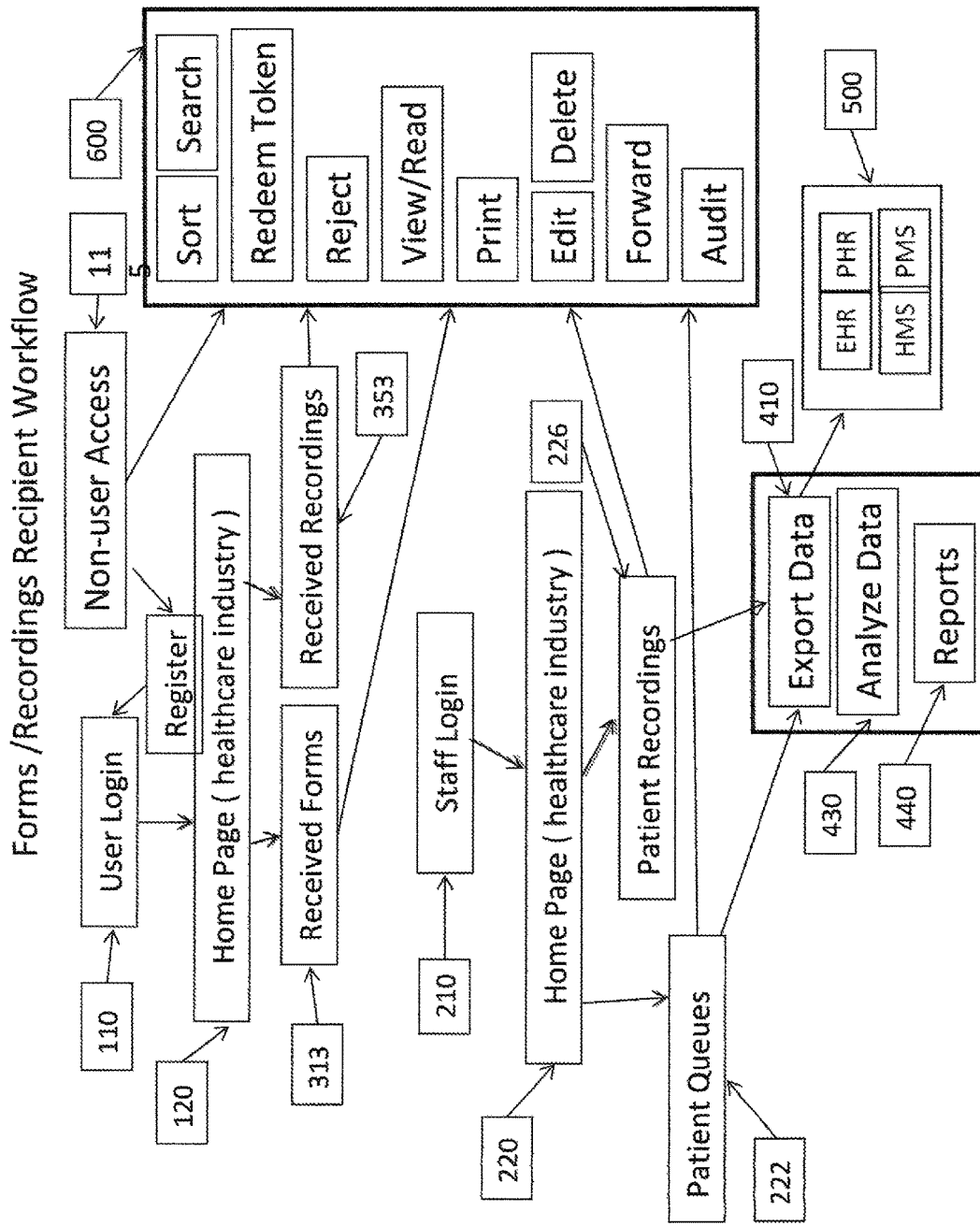
FIG. 16 shows forms/recorded data recipient work flow.

The process for an authorized user patient to authorize sharing of selected data with other users, non-users or organizations was discussed above. Now the method of handling that shared information on the authorized recipient side is described as shown in the FIG. 16. Here the user is the authorized recipient who logs in the account (110) and has access to forms sent by others (313) and recordings sent by others (353). Depending on system setup and sender's method of sending, the authorized recipient may have to submit a token to be able to access the data. Once they are permitted access to the data they can perform various actions as defined below (600). If the authorized recipient is not a user of the platform, the non-user gets information to access the data as a non-user (115), typically in an email linking them to the website powered by the platform, where they are authenticated and granted one time limited access to the platform to access the data that was sent to them. The non-user may register with the platform and become a user and have ongoing access or use one time limited access granted to them. For the authorized recipient healthcare staff, once they complete login (210) they have access to data based on their access rights defined by the patient/user in their service provider user profile within the platform. The healthcare user may export the data (410) to any integrated system such as EHR, PHR, HMS, PMS, etc. (500). The healthcare user may also analyze the data (430) received from many users for diagnostics or research purposes. The healthcare user may run various reports against the patients sending the data and its data usage (440). Once an authorized recipient healthcare user has access to the data, based on the access rights granted by the patient, the following types of functions are possible. (600): sort incoming data by sender, by time of day, by type of data, by recipient department, etc., search for specific sender or user or data, redeem token, reject—refuse to receive—the incoming data, view, review or read the data, print forms and data in various formats, edit the data, delete some or all the forms and data, forward the data to other users and audit the data for various purposes.

Figure 17:
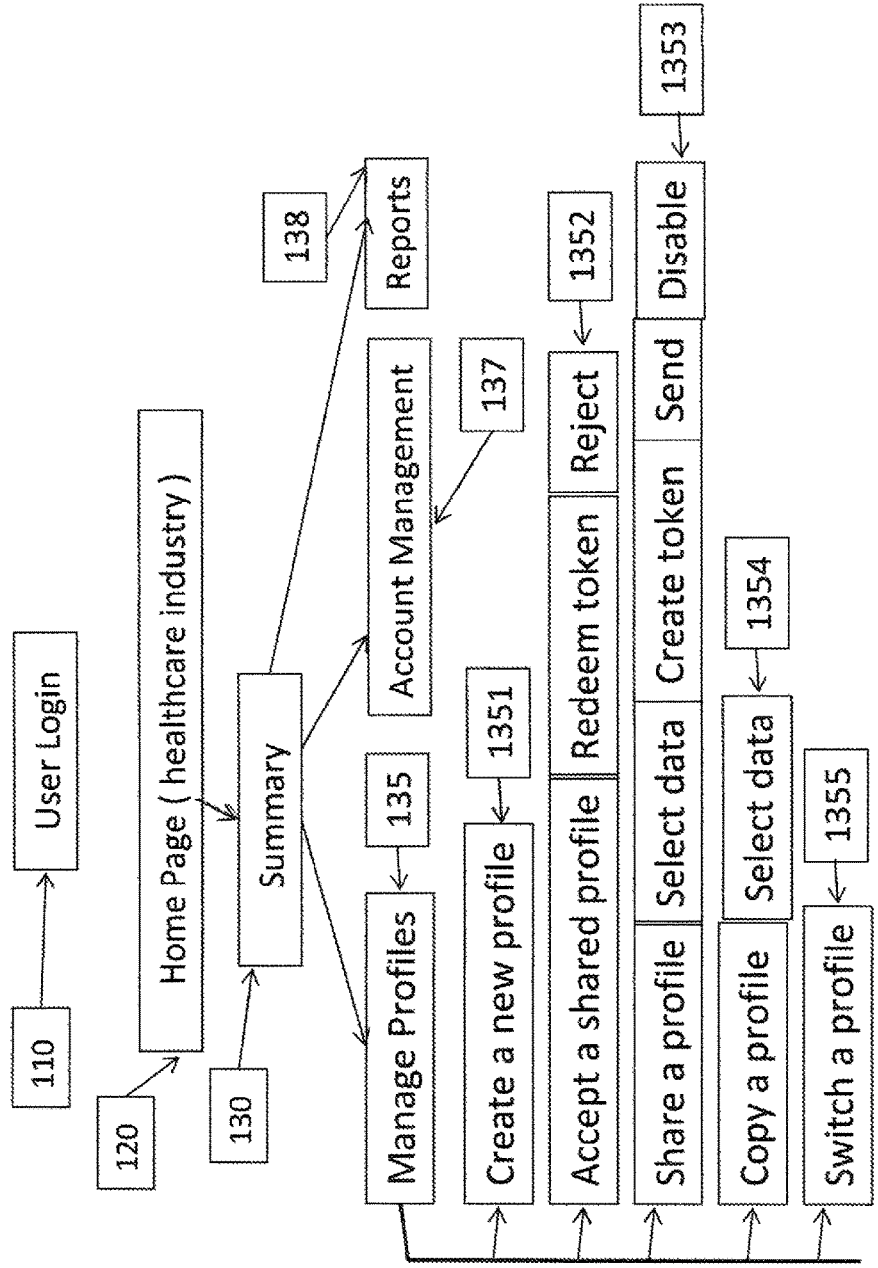
FIG. 17 shows workflow for sharing and activation of a profile.

One important part of this embodiment of the invention is to make it easy for a family member or a friend to take care of data entry and record keeping of information for a patient who may not be willing or able to do so. In this role the care taker becomes the authorized user of the platform and along with her own information, creates and manages profiles and records for other people. This activity could be permanent or for a duration of time, when the other person may no longer need the assistance or may want to co-manage the information. In FIG. 17, once the authorized user logs in to the platform, the authorized user proceeds to review a summary (130) of information or perform various administrative tasks like manage profile (135), manage account settings (137) and run reports (138). Here the authorized user can create a new profile for herself or a family member (1351). The user can receive a shared profile from another user and add that to her own profile set by redeeming a token or reject to receive such profile sharing (1352). The authorized user can select to share one or more of her own profiles with other users, select what part of her data may be shared with others, what the authorized recipient user may do with the shared profile data such as read or view it or edit and share with others and so on, create a token to protect unauthorized access, send an invitation to begin sharing or disable existing profile sharing arrangements (1353). The authorized user can copy various data elements from other profiles, for example copy insurance information from her profile to another family member profile or copy addresses or contact information or payment information and so on (1354). The authorized user has easy access to switch from one profile to another profile to do all the work that she is allowed to perform on a given profile. (1355). This method offers a unique option for parents to manage their children's medical information from birth and pass that lifelong medical history to them when they become an adult without any data re-entry by anyone. Similarly, when parents are no longer able to take care of their own medical history due to illness or injury, a son or daughter can easily be designated as the authorized user and assigned to manage their records for better coordination of treatment without searching for medical records in many places.

Following is a description of the methods of the present invention for loading data from the platform of the invention to existing platforms in the healthcare industry. As explained before, there may or may not be integration available to share the data and such sharing may be one direction—from the platform of the present invention to those authorized recipient healthcare platforms or in both directions. The methods in FIG. 18-A and FIG. 18-B show both—a manual process (420) and an automated process (410)—to load data from the present platform invention into various healthcare systems (500). In the manual process (420), the authorized recipient user logs in to the invention platform and finds the selected patient records, which may contain both data forms and vital recordings, that the patient authorized to be accessed and that need to be uploaded (421) and prints the information and logs off. Next the user logs into various platforms one by one—EHR system (422), HMS (423), PHR (424), (PMS) 425, etc. as may be used by that organization and manually enters the information in each system by logging in and out of respective platform, and repeats the process for each patient data set that needs to be uploaded.

In FIG. 18-B an automated process of uploading authorized selected data from this platform into various authorized recipient healthcare platforms (500) is described. This is a complex process as shown here involving multiple sub-processes (411), (412, (413) defined below. The system administrator logs in the platform and defines data export setup and rules (411). There are various rules for selecting forms and recordings that are system wide, and there are rules specific to a set of patients for a given organization, department or specialty. There are ways to activate and deactivate application of a specific rule to the data being exported. These rules may be applied on a set scheduled time or may be used on demand. Once the authorized recipient system administrator sets up such rules they are associated with various user profiles and a user assigned to a given profile authorizes and allows the system to initiate a one time or ongoing exporting of patient data from the invention platform to the healthcare platforms for a given organization or department.

Along with the system setup, there may be a need to perform various data translations or mapping so data from the platform of the invention can be accepted by various other platforms. These translators (4131) provide a "translation matrix" and are provided in the present platform to take data from the platform and convert the data into a format that the receiving system can accept. The data handling for patient personal or medical profiles may be very different than data handling for patient recordings and the receiving systems may have various restrictions on what data it may receive to register a patient versus what data it may accept as vital readings on a patient that is already registered in that system. To handle incoming data, these platforms may need adaptors or plug-ins (4132) that could be provided by the third party or the present platform invention can provide a matched pair of translator and adopter to facilitate the communication.

While description of the present invention heretofore has been on one way data transfer from the platform of the invention to third party systems, it is equally possible to take data from the third party system and bring that data in to the present invention platform. This will enable better user experience for returning patients, for example, by coordination of information such as scheduled appointment times. This two way communication also allows the authorized recipient healthcare provider platform to send additional data, like test results and visit outcome and prescription information and so on, for a patient to receive inside the patient controlled platform of the present invention, thus eliminating a need for the patient to manually upload and maintain such information for future use.

Thus far the application of the present invention has been directed to a discussion and explanation of its use, for example only, in healthcare industry where an authorized user patient maintains control of and shares only as much of his information as he selects with only authorized recipient healthcare providers and other authorized recipient users at the patient's sole discretion. It should be clear by now, that the same paradigm shift is envisioned for other industries. The goal is for the consumer to enter any data needed to complete any and all application or registration processes at a service provider one time and in one place and for the consumer to maintain control of that data and to use it as needed as many times and places with authorized recipients.

A person familiar with such technologies will be able to see that this model applies to many other normal interactions with industries like banking, insurance, education, utilities and government services. For example only, FIG. 19-A shows an abstraction of the system where various users (1010) of the system are defined as consumers, co-users, organization staff or managers or administrators of the facility or service. These users access the services provided by the platform of the invention using devices (20) like personal computers—a desktop or a laptop, mobile devices like smart phones and portable devices like tablets and transformers, independent of what manufacturer or operating systems they use. These devices connect to local Wi-Fi network (90) as well as Internet (80) to connect to services provided by applications connected with the invention. These applications could run on dedicated hardware/software platform in more traditional fashion but are as likely to run on cloud services (40). Such a platform will consist of hardware servers running various operating systems and creating virtual servers, that will provide data base servers, application servers, interface servers providing network services, security services, authentication services, load balancing, streaming, and client services which will drive the user experience and application logic. Personal services devices like smart watches, fitness bands, smart glasses, home or personal sensors or service robots or network of things (30) are used by the consumer to gather personal and environmental data and some of these devices may communicate with other devices over Wi-Fi network and/or Internet to connect to the service provided by the present invention to report routine or exception data. This data is analyzed by the client services in the cloud or dedicated servers (40). The application defined in this invention also communicates with third party interfaces (50) which allow integration with external systems to exchange relevant information such as identity information, readings for other platforms such as identity information, credit score or financial history or social score, etc., exchanges data with other information systems (60) so that a new customer can be registered in the existing systems or an existing customer of those organizations may be verified as such and information may be exchanged or updated as needed, as well as many third party platforms (70) such as may exist among many providers of many services. As smart devices evolve around home and person, the network of things evolves where tremendous amount of data is available for the user and the platform of the invention provides an exchange or clearing house to route such data to an appropriate party or system. Home alerts from home may be routed to maintenance person or fire department or a security company and so on. With these external interactions important data may be sent to those systems as well as existing information may be imported in to the platform of the invention to provide additional services which may include but are not limited to rules based analysis, or decision support, reminders, alerts, or follow up activities. All of these data inputs and outputs are controlled according to the invention by the user.

While not as an extensive set of diagrams and description as set forth above for the healthcare example, the following figures and discussion explain how the present system may be used in each specific industry by a consumer and by respective service providers but give an overview that, in light of the discussion above, is clear to one ordinarily skilled in such technologies.

FIG. 19-B gives an overview of the service model. In this model, as with the one above, there are two main entities: I) (1000) the consumer who accesses the system via a computer, tablet or a phone type device as explained above, and ii) (2000) users from various industries who may access the system via a computer, tablet or phone. Here the consumer is using personal information and other data to complete registration or application by filling forms for industry specific data requests. In this model, the "patient" is replaced with a consumer (1000) who accesses the system via a computer, tablet or a phone and, once identified as an authorized user, wishes to share necessary selected personal data and records from other sources with various organizations (2000) like banks, insurance company, schools, colleges, or utilities like phone or gas service providers or state and federal governments. Those organization staffs and administrators access the system through computer, tablet or phone (3000). The information of interest, in this environment, is different from healthcare information, and includes, for example only and not by way of limitation, information such as credit history, past relationships with other similar entities, co-borrowers information, scores from various testing service or transcript of past records and so on. Again, as above, the key is that the consumer retains control of all the data and shares selected data with any one she desires to share it with but only upon her authorization. When this authorized user consumer goes from one service provider to another provider she is able to sign-up, switch or check in with any service provider she wants without having to re-enter any data. The authorized recipient organization also does not have to handle a set of forms and data entry tasks. From the platform of the invention that is optimized for her, the authorized user consumer selects the data she wishes to share with a given authorized recipient provider and sends that particular data to that facility thus avoiding data entry errors or dependency on anyone else. As above, this consumer is also able to keep data for other family members in the system so that if she is responsible for anyone else in the family, she can manage that data just as effectively as she handles her own data. The power of this individual centric data management process model becomes obvious as more and more data is generated by smart devices at the consumer level in person or at home or at remote locations that is routed through the platform of the present invention without the consumer having download apps or interface for each such device or additional services.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. An individual and group centric bidirectional data management method for a user to aggregate personal information, medical history and health and wellness data manually or through secure interfaces on an encrypted cloud based software platform designated computer system that said user can use to exchange said data with any authorized third party or recipient healthcare providers or with any recipient or authorized third party family members, care givers and others in a bidirectional controlled way via a one time secure token using a personal computer, tablet or smart phone, the method comprising the steps of:

a) receiving a user's authorized account creation request at said designated computer system and said designated computer system completing authorized account setup and authorization process upon first login attempt, and completing verification and multifactor authentication on all login attempts and performing ID verification and authentication for validation and fraud prevention using user entered information or third party services;

b) said designated computer system encrypting all the personal and medical information using encryption with personal and public key;

c) said designated computer system presenting to said user a list of general and specialty medical history profiles and status of each profile completion including percentages, readings and alerts upon logging in;

d) said designated computer system receiving user input to complete personal information consisting of demographics, emergency contacts, insurance, payments, medical directives and medical information;

e) said designated computer system uploading or importing said user documents and images including lab reports, medical photos, identification card, insurance cards, directives and consents discharge summary and clinical reports;

f) said designated computer system receiving said user input to complete adult or child primary care information including purpose of visit, history of prior illnesses, previous surgical procedures, prior, hospitalization, and tests performed;

g) said designated computer system recording vitals and biometrics data including blood pressure, blood glucose level, blood oxygen level, weight, body temperature, and pulse rate manually entered by the user or automatically recorded from connected devices or transferred from a third party system;

h) said designated computer system presenting to said user or authorized third party the forms, documents, charts and readings aggregated from all sources;

i) said designated computer system user sharing aggregated records with authorized third parties using the same system;

j) said designated computer system user selecting one or more recipients of user information where said recipient may be an organization or a person with or without an authorized account on the system;

k) said designated computer system user selecting one or more medical data forms, documents and aggregated vital data readings and charts to be sent to the selected one or more recipients;

l) said designated computer system creating an optional out of band security token with optional finite validation time interval and single or multiple use for transmission to a recipient for validation of said recipient access to said system;

m) said designated computer system encrypting and decrypting the data using a public and private key that is filtered to match recipient organizational preferences and secured with sender's security token;

n) said recipient redeeming the security token so as to be able to receive the data;

o) said recipient viewing, printing, editing, forwarding or exporting the data to internal systems of the recipient;

p) said designated computer system receiving input from a recipient identifying incomplete parts of a data set sent by a user and prompting a user to complete the incomplete part of forms and readings and re-sending the data to said recipient; and q) said designated computer system taking data from external systems of an authorized third party, the one or more recipients and the user via various interfaces and updating the user information with the latest information from the external systems such that said updated latest user information is available to the user, the authorized third party and the one or more recipients in a secure bidirectional manner that ensures maintenance of complete up to date user information; and r) use of said up to date user information to treat said user.

2. The method of claim 1 wherein all the services provided by said designated computer system are independent of devices used by all users.

3. The method of claim 1 wherein step (c) further comprises:
(a) said designated computer system providing a prompt to said user directing said user to incomplete parts of data in any data set being worked by the user;
(b) said designated computer system providing a prompt to said user directing said user to completed parts of data in any data set being worked by the user; and
(c) said designated computer system providing prompts to said user in the form of alerts.

4. The method of claim 1 wherein step (d) further comprises:
(a) said designated computer system ensuring that personal information is common across various industries including healthcare, financial services, and education.

5. The method of claim 1 wherein step (e) further comprises:
(a) said designated computer system enabling use of a camera function of a phone, tablet or PC for uploading of an image of a person or document.

6. The method of claim 1 further comprising:
(a) said designated computer system including an identification process such that if identification of the user cannot be completed, said designated computer system enabling an alternate method to perform identification or ending the session.

7. The method of claim 1 further comprising the steps of:
(a) using age of user to determine if adult or child, and said designated computer system presenting age specific primary care medical information prompts to said user;
(b) said designated computer system only presents age specific information to a given user; and
(c) when the user ages from child to adult said designated computer system automatically moving data from one profile to another.

8. The method of claim 1 step (i) further comprising the step of:
(a) said designated computer system tagging content of a document for management and reporting on those documents.

9. The method of claim 1 step (k) further comprising the steps of:
(a) said designated computer system automatically moving some of the data from general profiles, primary care profiles, and other specialty into another given specialty; and
(b) said designated computer system ensuring that any specialty profile data entry is independent of other profile data entry in both order and sequence.

10. The method of claim 1 step (l) further comprising the steps of:
(a) said designated computer system receiving user input manually and collecting recordings including blood pressure, blood glucose level, blood oxygen level, weight, body temperature, and pulse rate; and
(b) said designated computer system receiving external device inputs automatically and collecting recordings including blood pressure, blood glucose level, blood oxygen level, weight, both temperature, and pulse rate.

11. The method of claim 1 wherein step (m) further comprises:
(a) said designated computer system enabling formatting of selected data to match forms or display layout of a given recipient;
(b) said designated computer system enabling formatting of selected medical data to filter the data against various criteria including changes in information or missing information or critical information; and
(c) said designated computer system enabling a recipient to chart or graph readings with various criteria including time or date range, and measurement range.

12. The method of claim 1 wherein step (o) farther comprises:
(a) said designated computer system enabling printing and formatting of the selected data to match print or forms layout of a given recipient;
(b) said designated computer system enabling a recipient to print the selected data after filtering of the data against various criteria including changes in information or missing information or critical information; and (c) said designated computer system enabling a recipient to print the selected data after charting or graphing readings with various criteria as time or date range, measurement range, comparison against normal, and comparison against target goals.

13. The method of claim 1 wherein step (k) further comprises:
   (a) selecting a recipient individual using email address or id;
   (b) selecting a recipient institution with institution name or id;
   (c) selecting a recipient department or sub group within a recipient institution; and
   (d) selecting a recipient person or sub group of recipient people within a recipient department.

14. The method of claim 12 further comprising the steps of:
   (a) said designated computer system identifying if a recipient is a previous user of said system, and said designated computer system providing prompts to said recipient to help auto fill required information; and
   (b) said designated computer system identifying if said recipient is also a user or authorized third party of the designated computer system.

15. The method of claim 1 wherein step (n) further comprises:
   (a) said designated computer system providing a security token to a recipient that may only be redeemed once;
   (b) said designated computer system providing a security token that may be required each time the recipient wishes to read or print the forms; and
   (c) said designated computer system providing a security token that is generated by the system said security token consisting of a number or string of characters.

16. The method of claim 1 wherein step (p) further comprises:
   (a) said designated computer system providing a prompt showing latest date when the data was updated;
   (b) said designated computer system providing a prompt showing what percentage of information is incomplete;
   (c) said designated computer system providing a prompt showing data that is incomplete; and
   (d) said designated computer system providing a prompt showing what the recipient presentation of selected forms looks like.

17. The method of claim 1 wherein step (p) further comprises:
   (a) a filter is applied in the designated computer system for some or each and every data element of the a user's personal and medical records and said filter is used to review general data and specialty profiles;
   (b) said designated computer system provides as many filters per organization, per department or per user as selected by said user; and
   (c) and wherein said filters may be different for viewing and printing of forms.

18. The method of claim 1 further comprising:
   (a) said designated computer system enables sending a prompt to said user and recipient and said user or recipient receiving the prompt via email, text message and/or alert inside the designated computer system;
   (b) wherein said prompt gives the recipient information about the user and sharing of forms without disclosing any specific data;
   (c) wherein said prompt may provide a path to said designated computer system where the forms may be viewed where the recipient may or may not be a user or authorized third party of said designated computer system; and
   (d) wherein said prompt may be repeated by the user or designated computer system at certain intervals or till data is viewed by the recipient.

19. The method of claim 1 further comprising:
   (a) said designated computer system restricting a recipient to perform one or more of functions on said designated computer system based on recipient access rights as authorized by said user;
   (b) when exporting, said designated computer system ensuring that the interface between said designated computer system and a recipient system will support required communication, security, authentication and data translation protocols as specified by the recipient system;
   (c) when exporting said designated computer system ensuring that the interfaces supported are unique to each recipient system;
   (d) when exporting said designated computer system ensuring that the interfaces supported may be configured for unique implementations of each recipient system; and
   (e) when exporting data said designated computer system ensuring that selected data may be exported to multiple recipient systems based on organization requirements and configurations as authorized by said user.

20. The method of claim 1 further comprising the steps of:
   (a) a device connecting with said designated computer system and said designated computer system registering said device with said designated computer system;
   (b) said designated computer system enabling a user to set device parameters including recording frequency and unit measurements;
   (c) said designated computer system associating a data stream from the device to a particular user where the same device may be used by one or more users;
   (d) said device reporting the data to said designated computer system and the designated computer system recording the data;
   (e) said designated computer system enabling activating/deactivating of the device;
   (f) said designated computer system receiving and distributing the data received from one or more devices according to user selected parameters;
   (g) said designated computer system enabling a user to set ideal parameters and goals for any data stream;
   (h) said designated computer system enabling a user to set alert criteria for the data stream; and
   (i) said designated computer system generating and distributing alerts based on user selected parameters.

21. The method of claim 20 further comprising the steps of:
   (a) said designated computer system enabling use of a local network hub when necessary to manage multiple devices used by the same user so as to aggregate multiple data streams; and
   (b) said designated computer system enabling use a local network hub when necessary to manage multiple devices used by multiple users to aggregate multiple data streams.

22. The method of claim 21 further comprising the steps of:

(a) said designated computer system registering and managing a local network hub with said designated computer system;
(b) said designated computer system enabling activating/deactivating the local network hub; and
(c) said designated computer system enabling manual registration or automatic registration of devices with the local network hub.

23. The method of claim 20 wherein step (f) further comprises:
   (a) said designated computer system recording the data at a set interval or as becomes available for each user for each parameter;
   (b) said designated computer system analyzing the data and providing prompts for actions to be taken by said designated computer system; and
   (c) said designated computer system distributing the data to said user or others according to parameters set by said user.

24. The method of claim 20 wherein step (g) further comprises:
   (a) said designated computer system enabling a user to define an ideal value of each data stream being recorded;
   (b) said designated computer system enabling a user to define a range of values to be considered normal;
   (c) said designated computer system enabling a user to define a goal for the data stream to be compared against;
   (d) said designated computer system enabling a user to define values for each user and for each data stream; and
   (e) reporting defined and measured values on a single chart.

25. The method of claim 20 wherein step (i) further comprises:
   (a) said designated computer system providing alerts based on criteria defined by the user;
   (b) said designated computer system providing alerts based on criteria defined by the recipient;
   (c) said designated computer system providing alerts limited for set time of day or date range; and
   (d) said designated computer system providing alerts within said designated computer system or sent outside said designated computer system or submitted to a third party system via communication interfaces.

* * * * *